United States Patent
Lee et al.

(10) Patent No.: US 8,974,921 B2
(45) Date of Patent: Mar. 10, 2015

(54) CONDENSED-CYCLIC COMPOUND AND ORGANIC LIGHT-EMITTING DIODE COMPRISING THE SAME

(75) Inventors: Sun-Young Lee, Yongin (KR); Yoon-Hyun Kwak, Yongin (KR); Bum-Woo Park, Yongin (KR); Jong-Hyuk Lee, Yongin (KR); Bo-Ra Lee, Yongin (KR); Sang-Hyun Han, Yongin (KR); Hye-Jin Jung, Yongin (KR); Young-Kook Kim, Yongin (KR); Jin-O Lim, Yongin (KR); Seok-Hwan Hwang, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 418 days.

(21) Appl. No.: 13/296,465

(22) Filed: Nov. 15, 2011

(65) Prior Publication Data

US 2012/0319086 A1    Dec. 20, 2012

(30) Foreign Application Priority Data

Jun. 16, 2011   (KR) ........................ 10-2011-0058634

(51) Int. Cl.
| | | |
|---|---|---|
| *H01L 51/54* | (2006.01) | |
| *C07D 221/18* | (2006.01) | |
| *C07D 401/10* | (2006.01) | |
| *C07D 401/14* | (2006.01) | |
| *C07D 403/04* | (2006.01) | |
| *C07D 403/10* | (2006.01) | |
| *C07D 405/04* | (2006.01) | |
| *C07D 417/04* | (2006.01) | |
| *C07D 487/04* | (2006.01) | |

(52) U.S. Cl.
CPC ............ *C07D 401/10* (2013.01); *C07D 221/18* (2013.01); *C07D 401/14* (2013.01); *C07D 403/04* (2013.01); *C07D 403/10* (2013.01); *C07D 405/04* (2013.01); *C07D 417/04* (2013.01); *C07D 487/04* (2013.01)
USPC ............................... 428/690; 257/40; 546/58

(58) Field of Classification Search
None
See application file for complete search history.

(56) References Cited

U.S. PATENT DOCUMENTS

| | | | |
|---|---|---|---|
| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,074,801 | B1 | 7/2006 | Yoshida et al. |
| 2006/0144262 | A1 | 7/2006 | Koong |
| 2008/0012475 | A1 | 1/2008 | Oyamada et al. |
| 2008/0015399 | A1 | 1/2008 | Funahashi |

(Continued)

FOREIGN PATENT DOCUMENTS

| | | |
|---|---|---|
| EP | 1602648 | 12/2005 |
| JP | 08012600 | 1/1996 |

(Continued)

OTHER PUBLICATIONS

Li et al. Anal. Chim. Acta 2004, 526, p. 155.*

(Continued)

*Primary Examiner* — J. L. Yang
(74) *Attorney, Agent, or Firm* — Robert E. Bushnell, Esq.

(57) ABSTRACT

A condensed-cyclic compound and an organic light-emitting diode including the same.

21 Claims, 1 Drawing Sheet

(56) References Cited

U.S. PATENT DOCUMENTS

| | | |
|---|---|---|
| 2010/0038634 A1 | 2/2010 | Nagao et al. |
| 2010/0176377 A1 | 7/2010 | Fukushima et al. |
| 2010/0301319 A1* | 12/2010 | Kuma et al. .................... 257/40 |
| 2011/0031484 A1 | 2/2011 | Lee et al. |
| 2011/0084256 A1 | 4/2011 | Kim et al. |

FOREIGN PATENT DOCUMENTS

| | | |
|---|---|---|
| JP | 2000003782 | 1/2000 |
| KR | 1020060079625 | 7/2006 |
| KR | 1020070011460 | 1/2007 |
| KR | 1020070093401 | 9/2007 |
| KR | 10-2009-0128382 A | 12/2009 |
| KR | 1020100003624 A | 1/2010 |

OTHER PUBLICATIONS

Adachi et al., Confinement of charge carriers and molecular excitons within 5-nm-thick emitter layer in organic electroluminescent devices with a double heterostructure, Appl. Phys. Lett. (1990) 57, pp. 531-533.

Sakamoto et al., Synthesis, Characterization, and Electron-Transport Property of Perfluorinated Phenylene Dendrimers, J. Am. Chem. Soc. (2000) 122, pp. 1832-1833.

Tang et al., Organic electroluminescent diodes, Appl. Phys. Lett. (1987) 51, pp. 913-915.

Yamaguchi et al., Diphenylamino-Substituted 2,5-Diarylsiloles for Single-Layer Organic Electroluminescent Devices, Chem. Lett. (2001) pp. 98-99.

Chemical structure of 10-Azabenzo[a]pyrene from www.sigmaaldrich.com.

Li et al., Selective fluorescence quenching of nitrogen-containing polycyclic aromatic hydrocarbons by aliphatic amines, Anal Chim Acta 526 (2004) pp. 155-162. Cited in attached Extended European Search Report.

Buu-Hoi et al., Carcinogenic nitrogen compounds, J Chem Soc (1960) pp. 4500-4503. Cited in attached Extended European Search Report.

Saint-Ruf et al., L'acide polyphosphorique, agent commode de la synthese de Beyer-Combes: preparation et proprietes de quelques derives de la dimethyl-2,4 quinoleine, B Soc Chim Fr 7-8 (1973) pp. 2514-2517. Cited in attached Extended European Search Report. No English translation is available to Applicants; please see attached Extended European Search Report for explanation of relevance.

Extended European Search Report issued Jul. 13, 2012 in connection with European Patent Application Serial No. 12161814.4, which also claims Korean Patent Application Serial No. 10-2011-0058634 as its priority document.

Korean Office Action issued by Korean Patent Office on Sep. 25, 2014 in connection with Korean Patent Application No. 10-2011-0058634 and Request for Entry attached herewith.

* cited by examiner

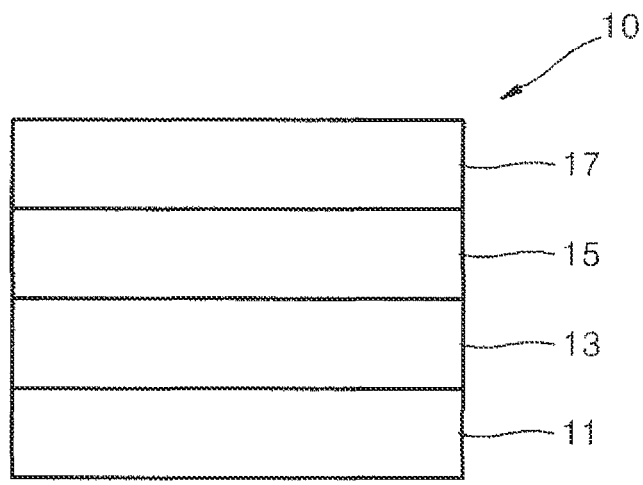

CONDENSED-CYCLIC COMPOUND AND ORGANIC LIGHT-EMITTING DIODE COMPRISING THE SAME

CLAIM OF PRIORITY

This application makes reference to, incorporates the same herein, and claims all benefits accruing under 35 U.S.C. §119 from an application for CONDENSED-CYCLIC COMPOUND AND ORGANIC LIGHT-EMITTING DIODE COMPRISING THE SAME earlier filed in the Korean Intellectual Property Office on 16 Jun. 2011 and there duly assigned Serial No. 10-2011-0058634.

BACKGROUND OF THE INVENTION

1. Field of the Invention

The present invention relates to a condensed-cyclic compound and an organic light-emitting diode including at least one of the condensed-cyclic compounds.

2. Description of the Related Art

Organic light-emitting diodes (OLEDs), which are self-emitting devices, have advantages such as a wide viewing angle, an excellent contrast, a quick response, high brightness, excellent driving voltage characteristics, and can provide multicolored images.

A general organic light-emitting diode has a structure including a substrate, an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of a general organic light-emitting diode having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a condensed-cyclic compound and an organic light-emitting diode including the condensed-cyclic compound. The present invention provides a condensed-cyclic compound capable of providing an organic light-emitting diode having low driving voltage, high brightness, high quantum efficiency, and long lifespan.

According to an aspect of the present invention, there is provided a condensed-cyclic compound represented by Formula 1 below:

Formula 1

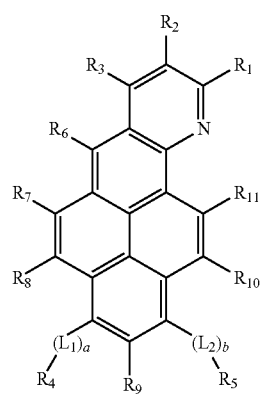

wherein $R_1$ to $R_{11}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, —N($R_{21}$)($R_{22}$), or —Si($R_{23}$)($R_{24}$)($R_{25}$); $L_1$ to $L_2$ are each independently a substituted or unsubstituted $C_5$-$C_{60}$ arylene group or a substituted or unsubstituted $C_2$-$C_{60}$ heteroarylene group; a and b are each independently an integer from 0 to 5; and $R_{21}$ to $R_{25}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group.

According to another aspect of the present invention, there is provided an organic light-emitting diode including: a first electrode; a second electrode disposed opposite to the first electrode; a first layer interposed between the first electrode and the second electrode, wherein the first layer comprise at least one of the condensed-cyclic compounds:

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components wherein:

FIG. 1 is a schematic cross-sectional view of an organic light-emitting diode according to an embodiment of the present invention.

DETAILED DESCRIPTION OF THE INVENTION

Hereinafter, the present invention will now be described more fully with reference to the accompanying drawings, in which exemplary embodiments of the present invention are shown.

A condensed-cyclic compound according to an embodiment of the present invention is represented by Formula 1 below.

Formula 1

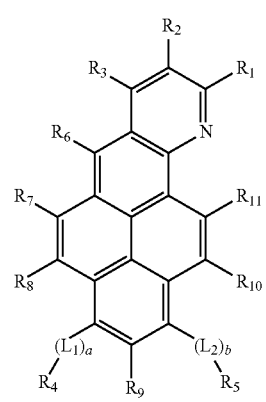

In Formula 1, $R_1$ to $R_{11}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, —$N(R_{21})(R_{22})$, or —$Si(R_{23})(R_{24})(R_{25})$.

For example, $R_1$ to $R_{11}$ may be each independently a hydrogen atom, a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, a pentoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, or —$N(R_{21})(R_{22})$, but are not limited thereto.

For example, in Formula 1, $R_1$ to $R_{11}$ may be each independently a hydrogen atom, a heavy hydrogen atom, a halogen atom, a hydroxyl group, a cyano group, a nitro group, a carboxyl group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, or one of Formulae 2A to 2Q below, but are not limited thereto.

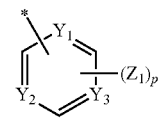

Formula 2A

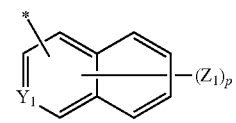

Formula 2B

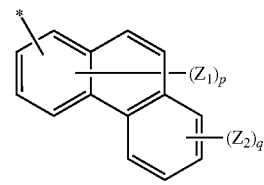

Formula 2C

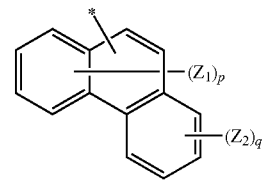

Formula 2D

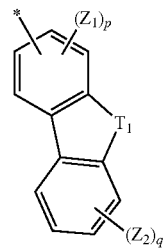

Formula 2E

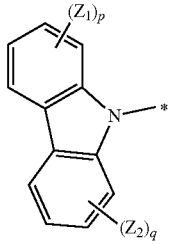

Formula 2F

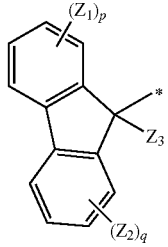

Formula 2G

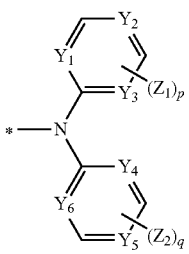

Formula 2H

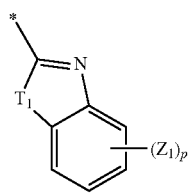

Formula 2I

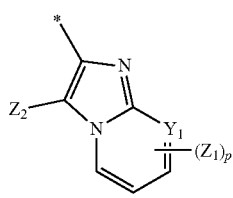

Formula 2J

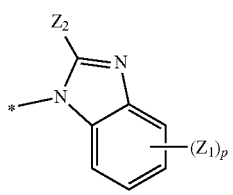

Formula 2K

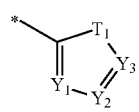

Formula 2L

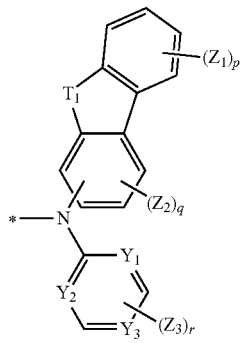

Formula 2M

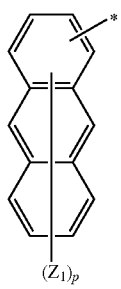

Formula 2N

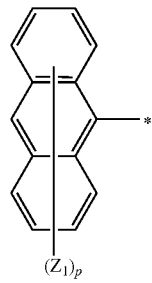

Formula 2O

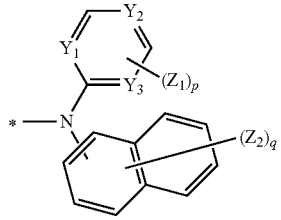

Formula 2P

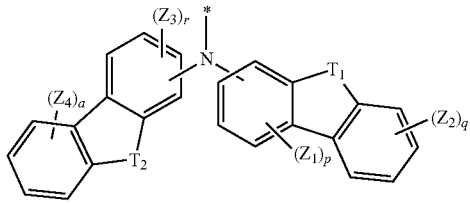

Formula 2Q

In Formulae 2A to 2Q, $Y_1$ to $Y_6$ may be each independently =N— or =C($Z_{11}$)—, and $T_1$ and $T_2$ may be each independently —S—, —O—, —N($Z_{12}$)— or —C($Z_{13}$)($Z_{14}$)—.

Meanwhile, in Formulae 2A to 2Q, $Z_1$ to $Z_4$ and $Z_{11}$ to $Z_{14}$ are each independently a hydrogen atom; a heavy hydrogen atom; a halogen atom; a hydroxyl group; a cyano group; a nitro group; a carboxyl group; a $C_1$-$C_{60}$ alkyl group; a $C_1$-$C_{60}$ alkyl group substituted with at least one of a heavy hydrogen atom, a halogen atom, a hydroxyl group, a cyano group, a nitro group, and a carboxyl group; a $C_2$-$C_{60}$ alkenyl group; a $C_2$-$C_{60}$ alkenyl group substituted with at least one of a heavy hydrogen atom, a halogen atom, a hydroxyl group, a cyano group, a nitro group, and a carboxyl group; a $C_2$-$C_{60}$ alkynyl group; a $C_2$-$C_{60}$ alkynyl group substituted with at least one of a heavy hydrogen atom, a halogen atom, a hydroxyl group, a cyano group, a nitro group, and a carboxyl group; a $C_1$-$C_{60}$ alkoxy group; a $C_1$-$C_{60}$ alkoxy group substituted with at least one of a heavy hydrogen atom, a halogen atom, a hydroxyl group, a cyano group, a nitro group, and a carboxyl group; a $C_3$-$C_{60}$ cycloalkyl group; a $C_3$-$C_{60}$ cycloalkyl group substituted with at least one of a heavy hydrogen atom, a halogen atom, a hydroxyl group, a cyano group, a nitro group, and a carboxyl group; a $C_5$-$C_{60}$ aryl group; a $C_5$-$C_{60}$ aryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_5$-$C_{60}$ aryloxy group; a $C_5$-$C_{60}$ aryloxy group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group, a $C_5$-$C_{60}$ arylthio group, and a $C_5$-$C_{60}$ arylthio group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_2$-$C_{60}$ heteroaryl group; or a $C_2$-$C_{60}$ heteroaryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group.

For example, $Z_1$ to $Z_4$ and $Z_{11}$ to $Z_{14}$ may be each independently a hydrogen atom; a heavy hydrogen atom; a halogen atom; a hydroxyl group; a cyano group; a methyl group; an ethyl group; a propyl group; a butyl group; a pentyl group; an ethenyl group; a propenyl group; a butenyl group; a pentenyl group; an acetyl group; a methoxy group; an ethoxy group; a propoxy group; a butoxy group; a pentoxy group; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group or a chrysenyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; or a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group, but are not limited thereto.

In Formulae 2A to 2Q, p may be an integer from 1 to 9; q may be an integer from 1 to 7; r may be an integer from 1 to 3; and s may be an integer from 1 to 4, but they are not limited thereto.

If p is 2 or greater, $Z_1$s may be the same or different from each other. If q is 2 or greater, $Z_2$s may be the same or different from each other. If r is 2 or greater, $Z_3$s may be the same or different from each other. If s is 2 or greater, $Z_4$s may be the same or different from each other.

For example, $R_1$ to $R_{11}$ may be each independently a hydrogen atom, a heavy hydrogen atom, a halogen atom, a hydroxyl group, a cyano group, a nitro group, a carboxyl group, a $C_1$-$C_{10}$ alkyl group; a $C_1$-$C_{10}$ alkoxy group, or one of Formulae 3A to 3T below, but are not limited thereto.

Formula 3A

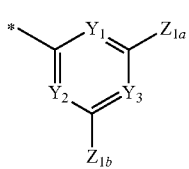

Formula 3B

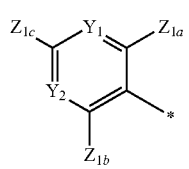

Formula 3C

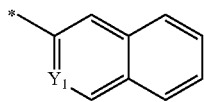

Formula 3D

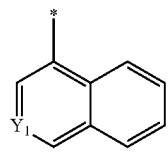

Formula 3E

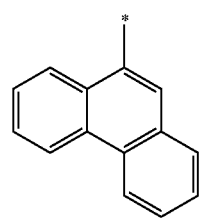

Formula 3F

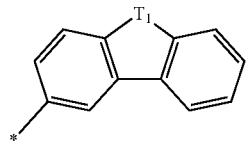

Formula 3G

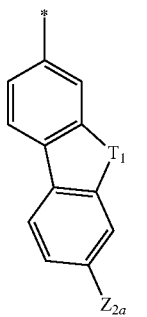

Formula 3H

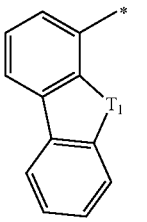

Formula 3I

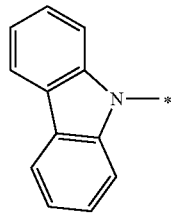

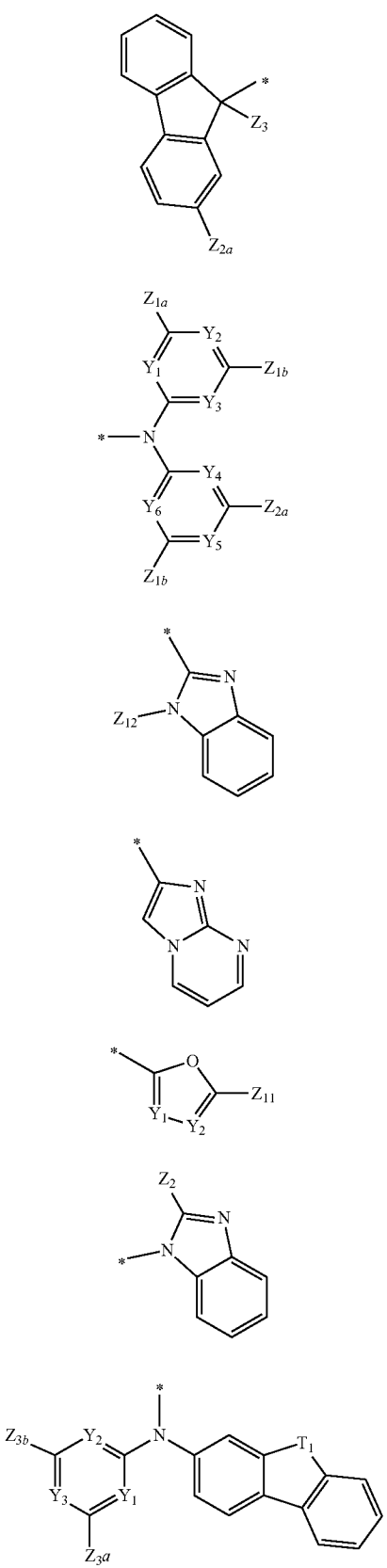

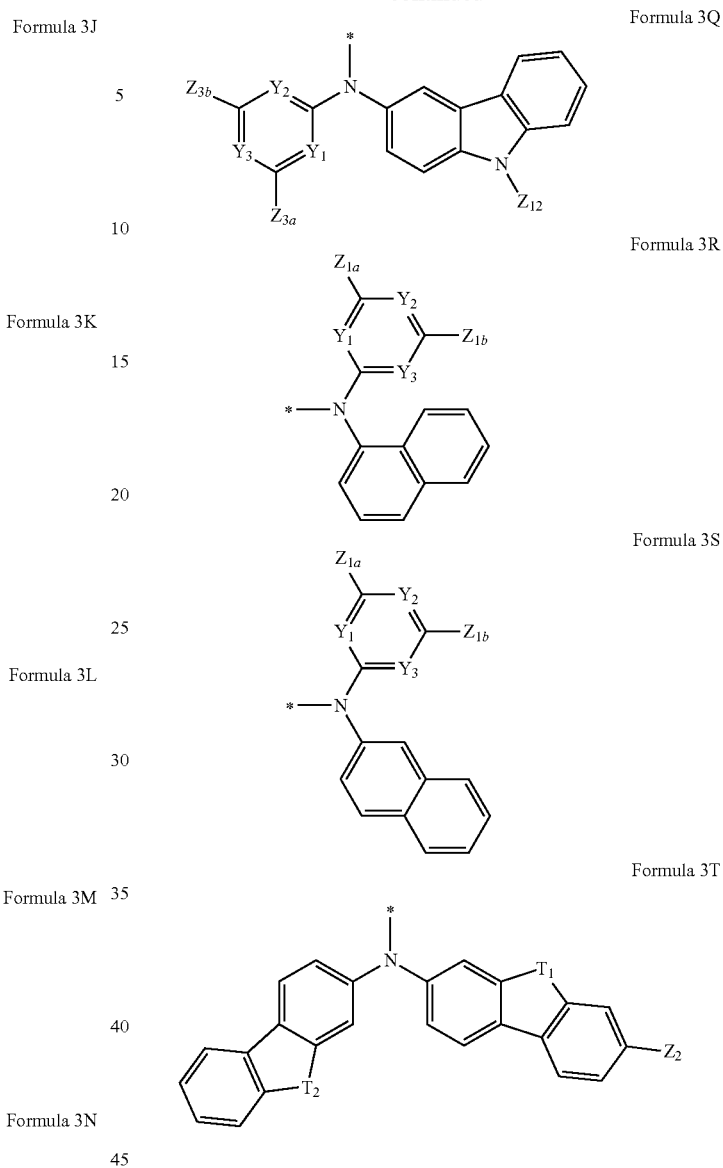

In Formulae 3A to 3T, $Y_1$ to $Y_6$, $T_1$ and $T_2$ are defined as described above. In Formulae 3A to 3T, $Z_{1a}$, $Z_{1b}$, $Z_{1c}$, $Z_2$, $Z_{2a}$, $Z_{2b}$, $Z_3$, $Z_{3a}$, $Z_{3b}$, $Z_{11}$, $Z_{12}$, $Z_{13}$ and $Z_{14}$ are defined as described above with reference to $Z_1$.

In Formula 1, $L_1$ and $L_2$ may be each independently a substituted or unsubstituted $C_5$-$C_{60}$ arylene group or a substituted or unsubstituted $C_2$-$C_{60}$ heteroarylene group.

For example, $L_1$ and $L_2$ may be each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentacenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group; a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanyl group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group, but are not limited thereto.

For example, $L_1$ and $L_2$ may be each independently represented by one of the Formulae 4A to 4O below.

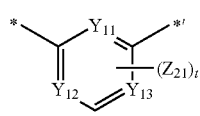

Formula 4A

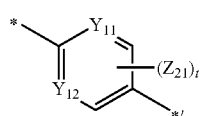

Formula 4B

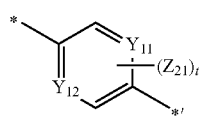

Formula 4C

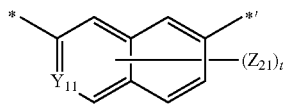

Formula 4D

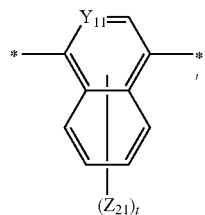

Formula 4E

Formula 4F

Formula 4G

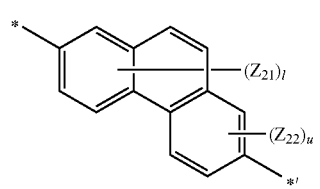

Formula 4H

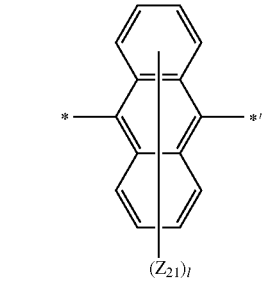

Formula 4I

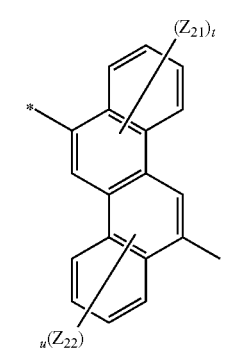

Formula 4J

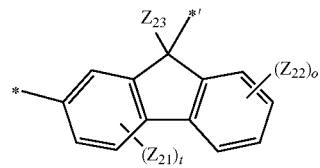

Formula 4K

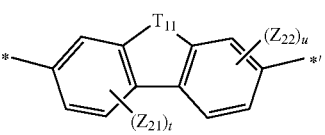

-continued

Formula 4L

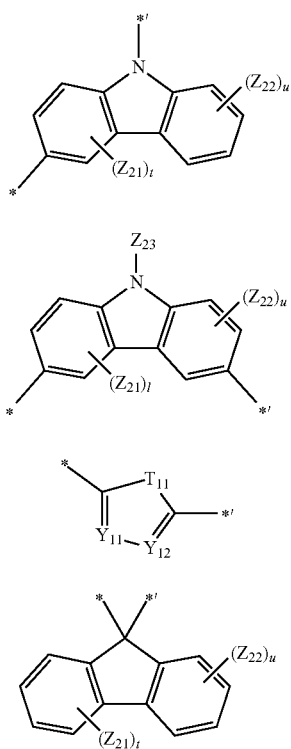

Formula 4M

Formula 4N

Formula 4O

In Formulae 4A to 4O, $Y_{11}$ to $Y_{13}$ may be each independently =N— or =C($Z_{31}$)—, and $T_{11}$ may be —S—, —O—, —N($Z_{32}$)—, or —C($Z_{33}$)($Z_{34}$)—. $Z_{21}$ to $Z_{23}$ and $Z_{31}$ to $Z_{34}$ are defined as described above with reference to $Z_1$. Here, t may be an integer from 1 to 8; and u may be an integer from 1 to 5. If t is 2 or greater, $Z_{21}$s may be the same or different from each other. If u is 2 or greater, $Z_{22}$s may be the same or different from each other.

In Formula 1, a and b are an integer from 0 to 5, respectively. For example, a and b may be 0, 1, or 2, respectively.

If a or b is 0, $R_4$ or $R_5$ is directly connected to a carbon atom of pyrene. If a is 2 or greater, $L_1$s may be the same or different from each other. If b is 2 or greater, $L_2$s may be the same or different from each other.

The condensed-cyclic compound of Formula 1 may be represented by Formula 1A or 1B below, but is not limited thereto:

Formula 1A

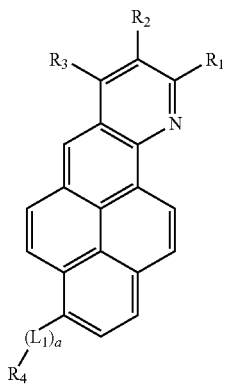

Formula 1B

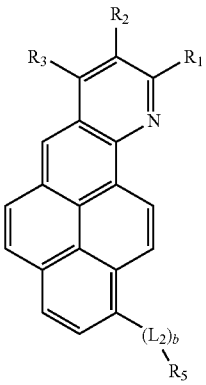

In Formulae 1A and 1B, $R_1$ to $R_5$, $L_1$, $L_2$, a, and b are defined as described above.

For example, in Formulae 1A and 1B, $R_1$ to $R_3$ may be each independently a hydrogen atom, a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, a pentoxy group, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrimidinyl group, a substituted or unsubstituted quinolinyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted dibenzothiophenyl group, a substituted or unsubstituted dibenzofuranyl group, a substituted or unsubstituted triazinyl group, or a substituted or unsubstituted oxadiazolyl group; $R_4$ and $R_5$ may be each independently represented by one of the Formulae 2A to 2Q (for example, Formulae 3A to 3T); $L_1$ and $L_2$ may be each independently represented by one of the Formulae 4A to 4O; and a and b are each independently 0, 1, or 2, but they are not limited thereto.

Since a pyrene and a pyridine are fused in the compound of Formula 1, a π-conjugation system is formed, resulting in reducing non-radiative decay. An organic light-emitting diode including the condensed-cyclic compound represented by Formula 1 has high quantum yield, and thus light-emitting efficiency of the organic light-emitting diode may be improved.

The condensed-cyclic compound represented by Formula 1 may be any one compound of Compounds 1 to 46 and Compounds 101 to 157 below, but is not limited thereto.

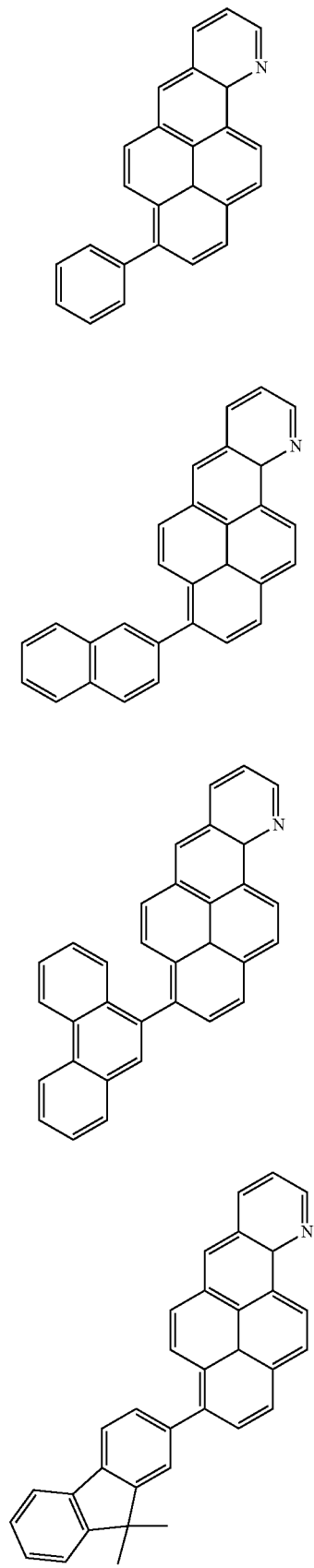
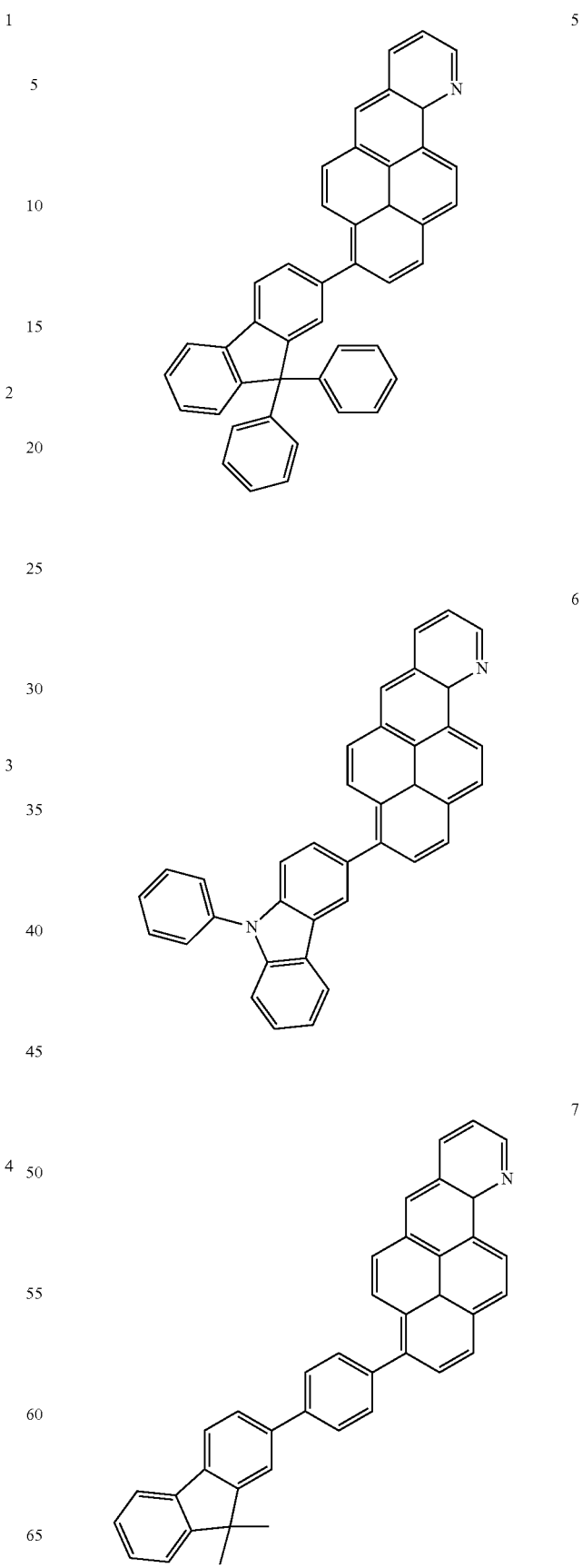

8
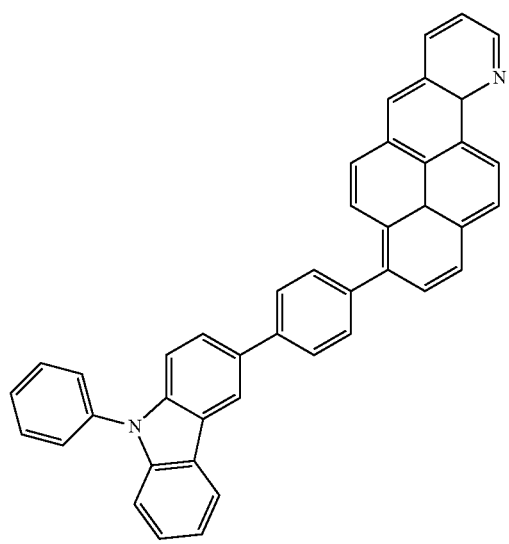
9
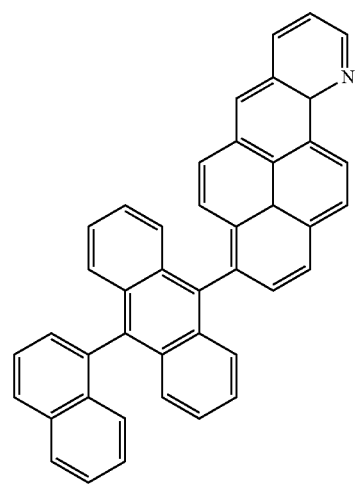
10
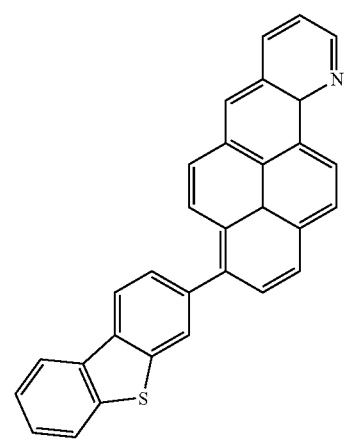
11
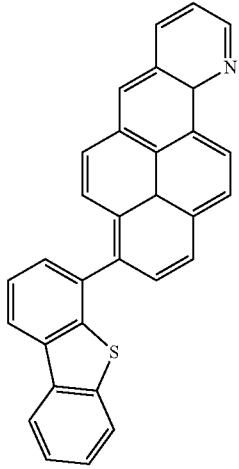
12
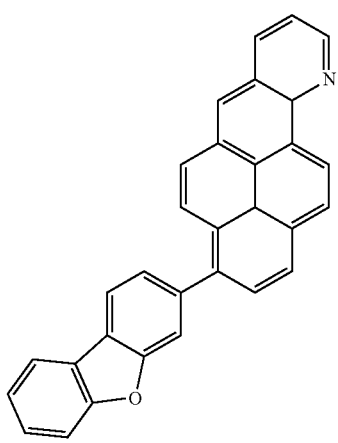
13
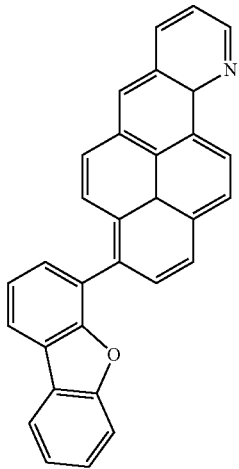

-continued
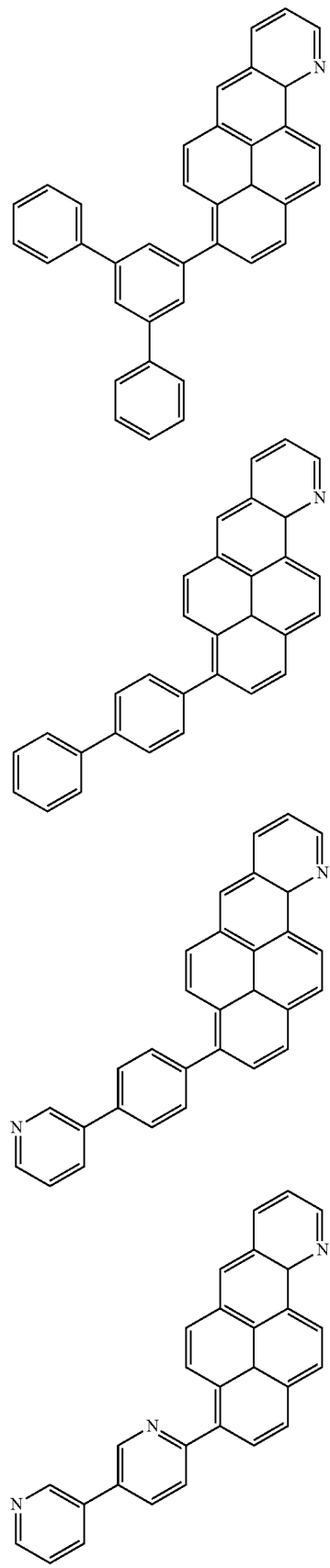
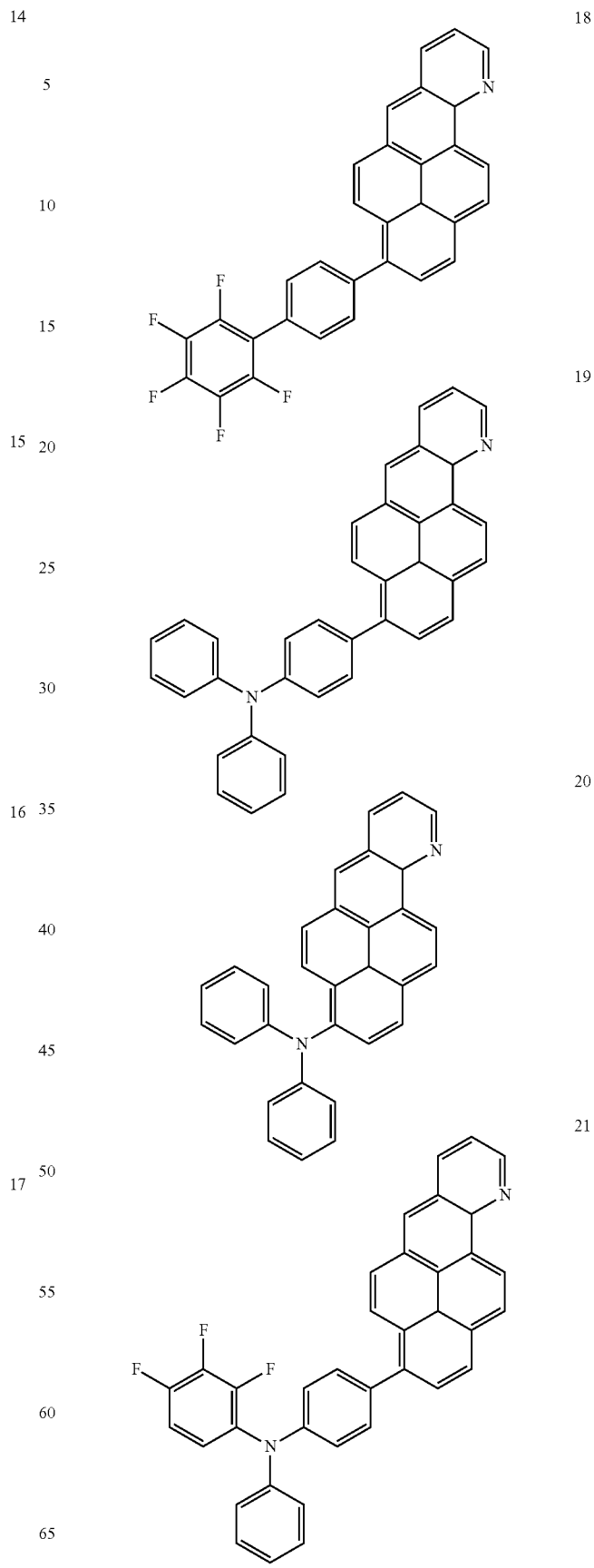

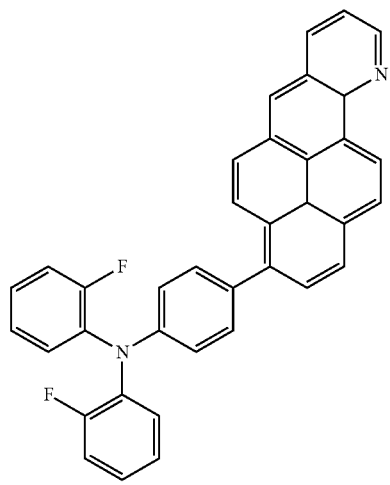
22
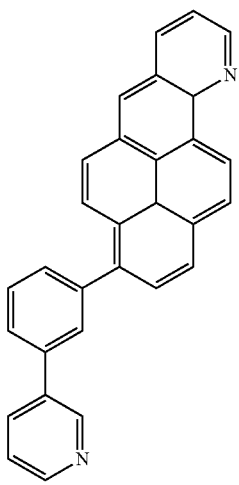
25
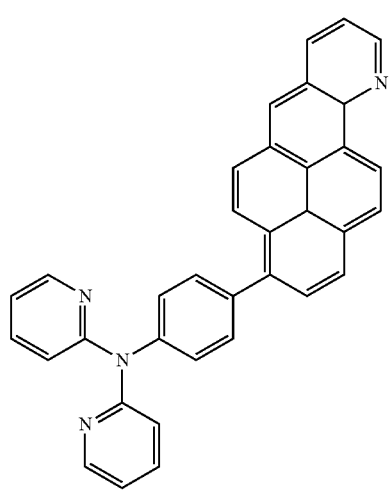
23
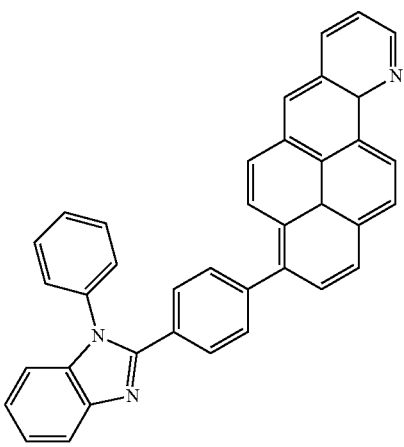
26
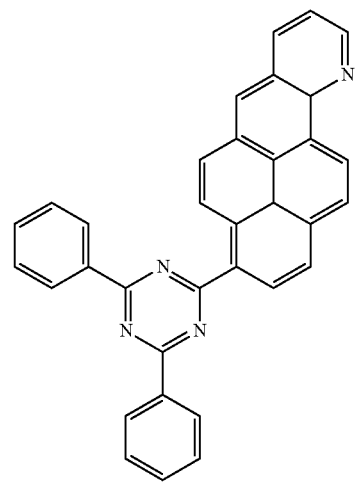
24
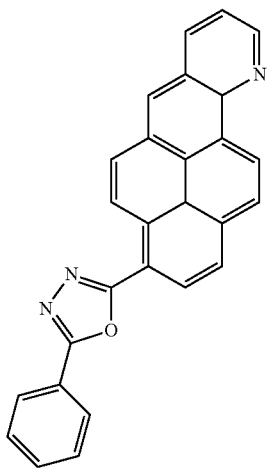
27

-continued
28
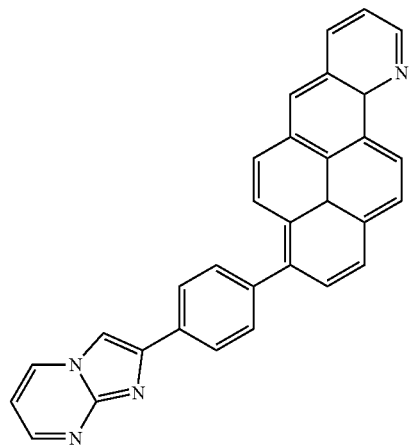
29
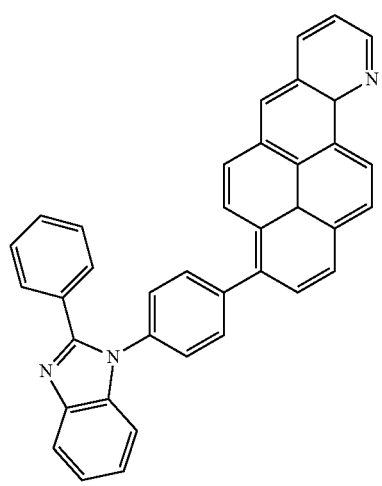
30
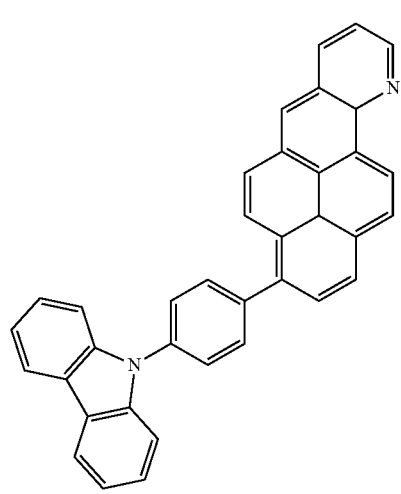
-continued
31
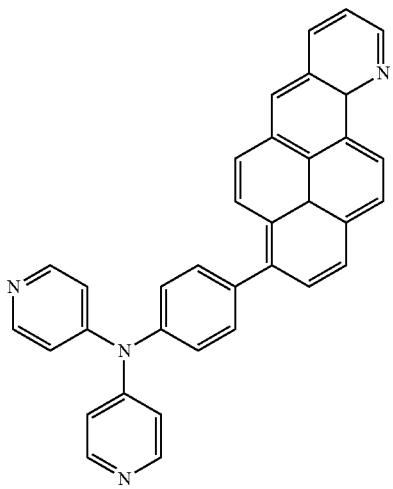
32
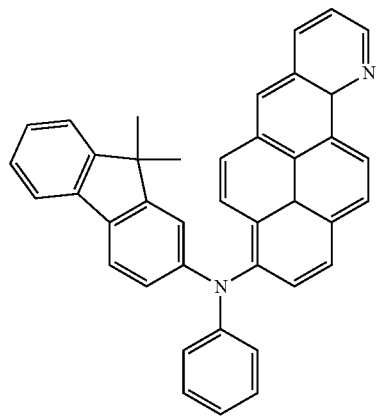
33
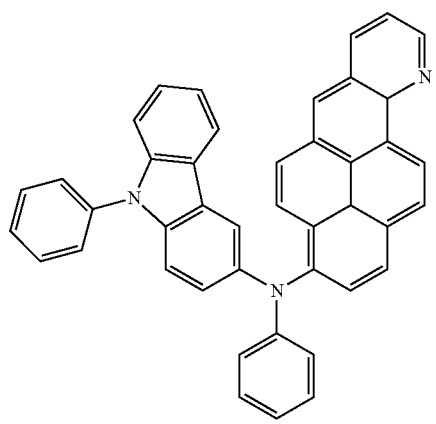

-continued
34
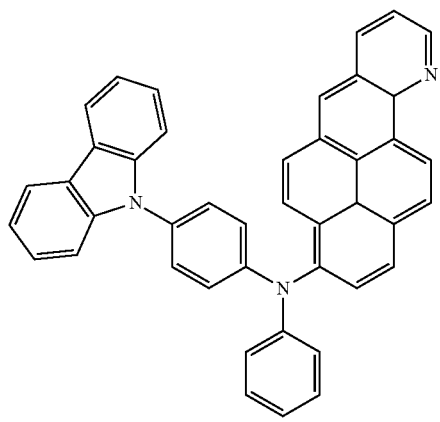
35
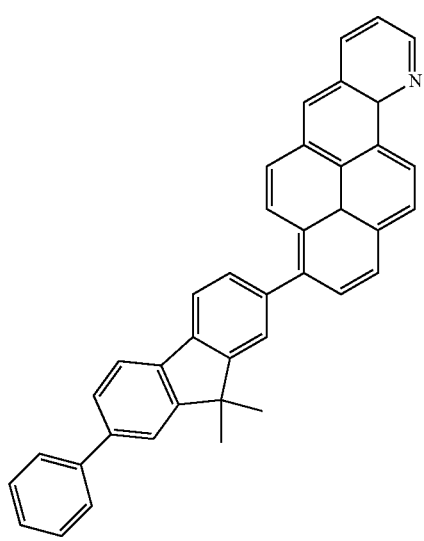
36
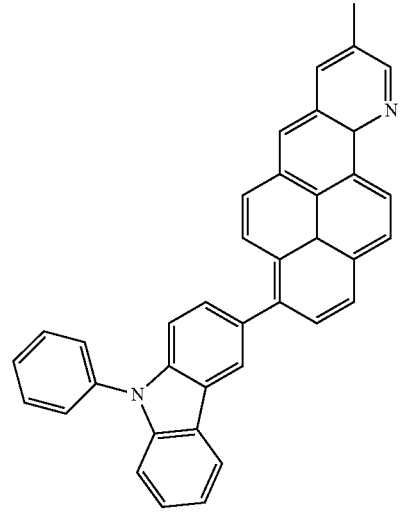
-continued
37
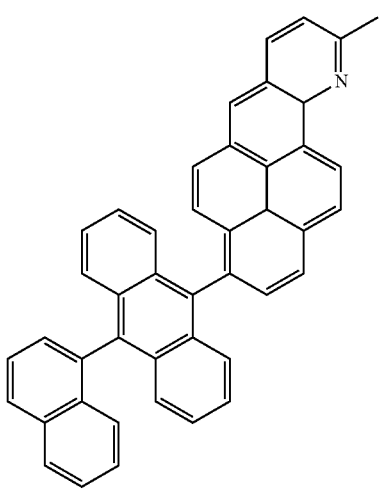
38
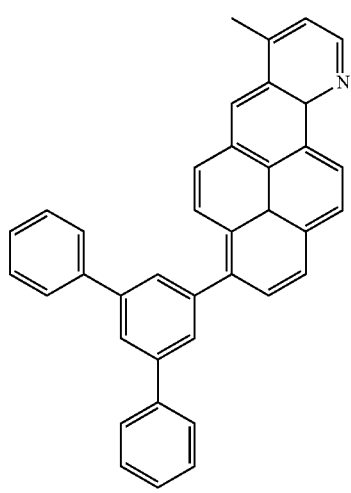
39
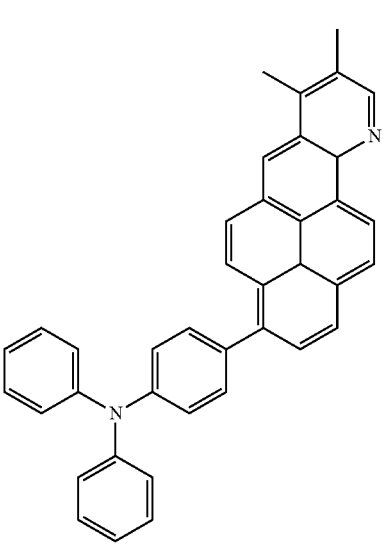

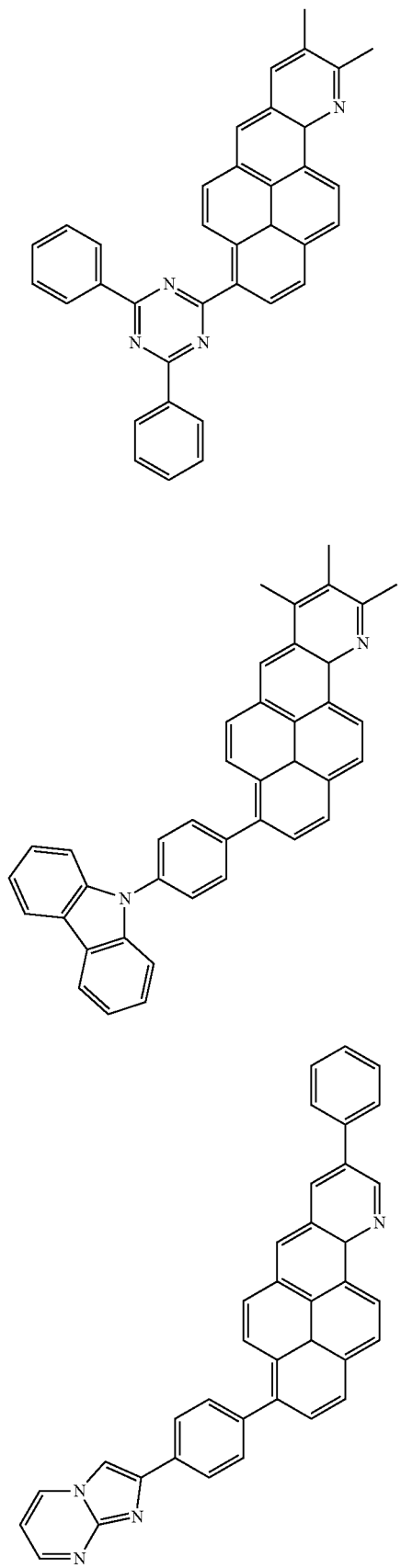
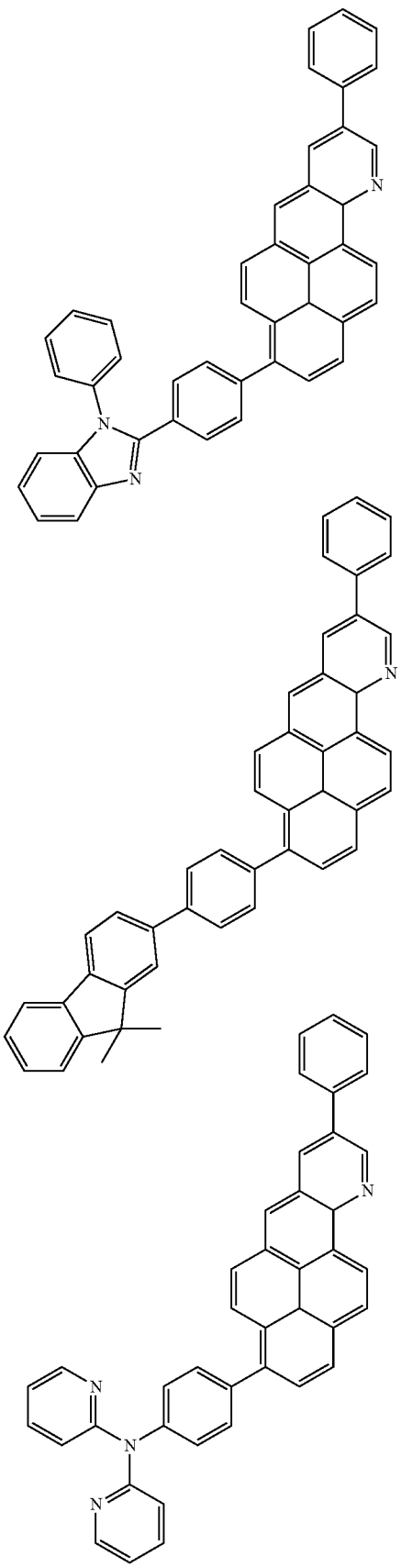

46
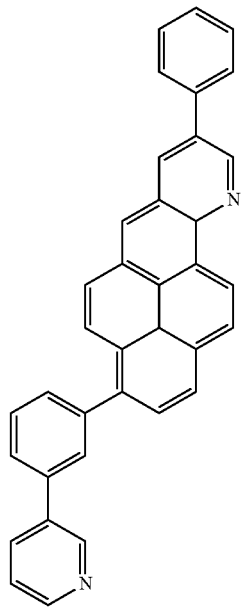
101
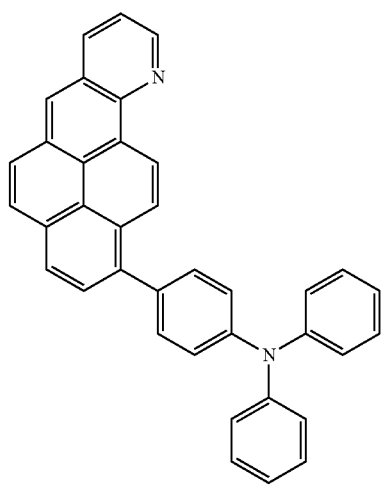
102
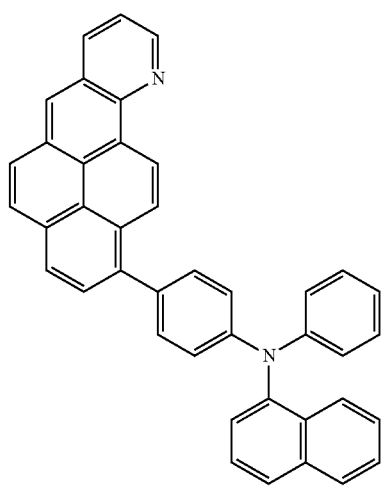
103
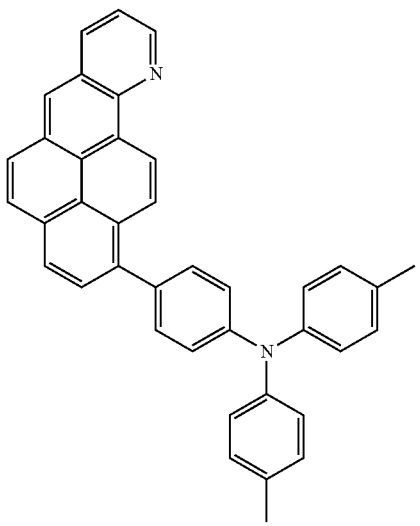
104
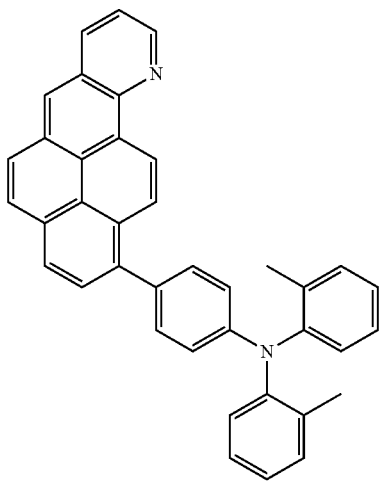
105
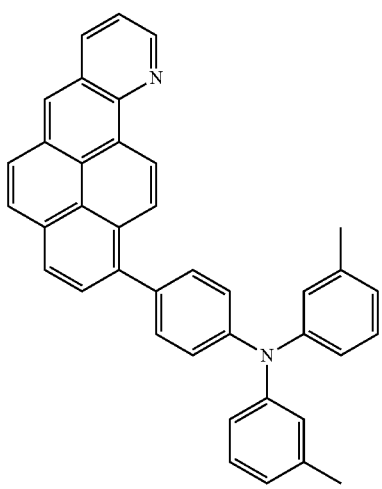

106
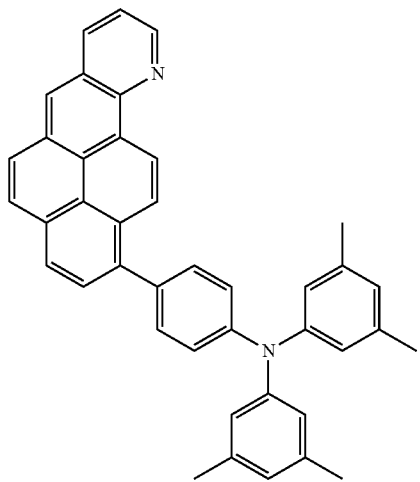
107
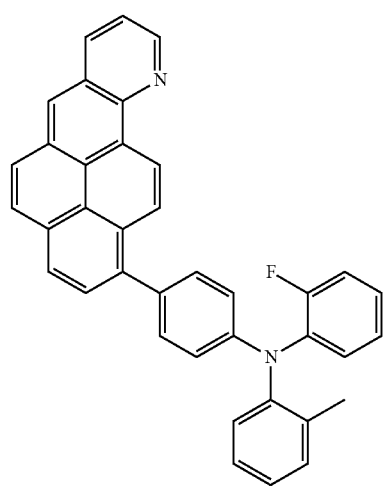
108
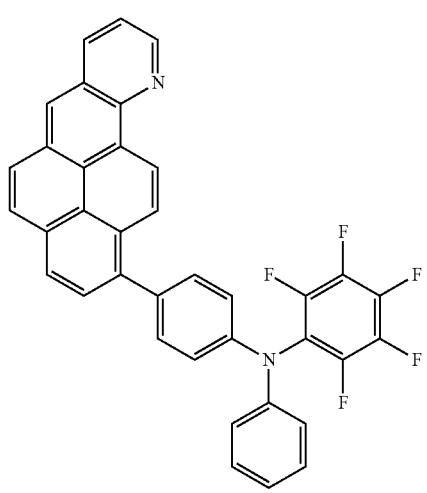
109
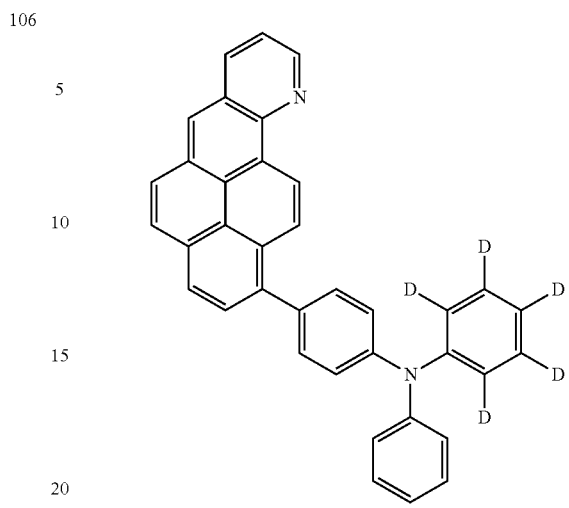
110
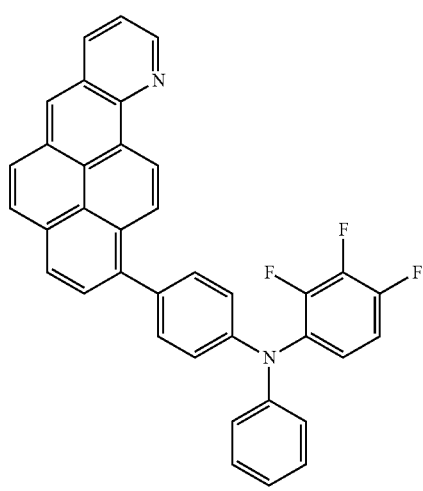
111
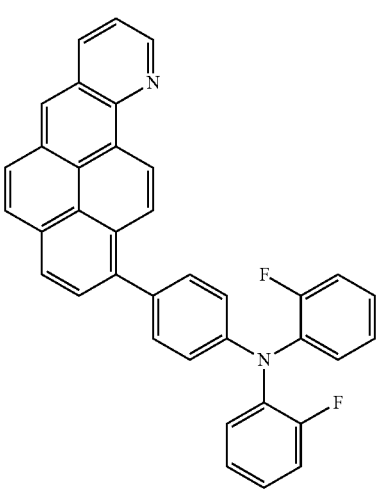

-continued
112
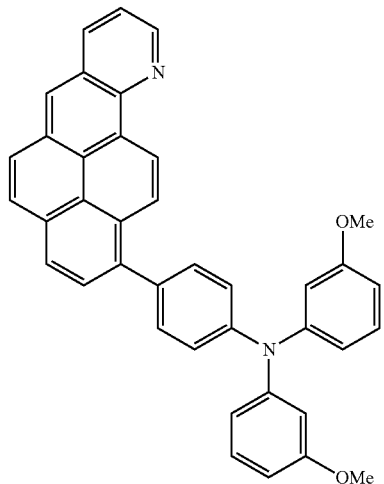
113
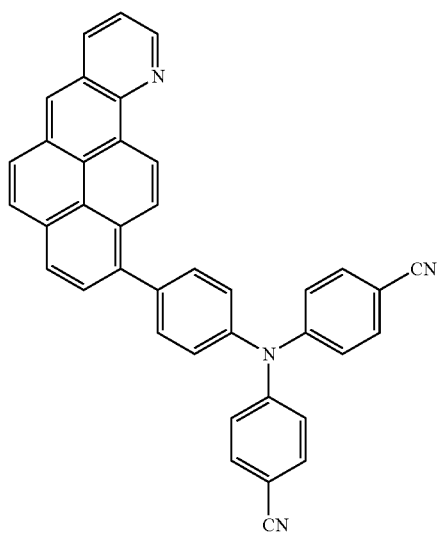
114
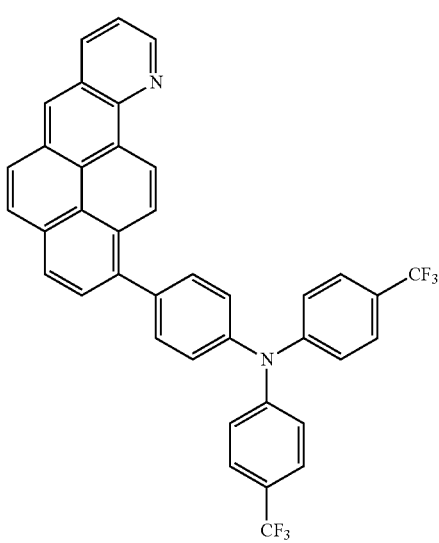
-continued
115
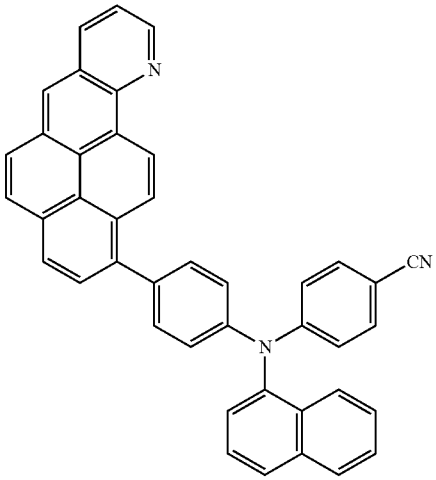
116
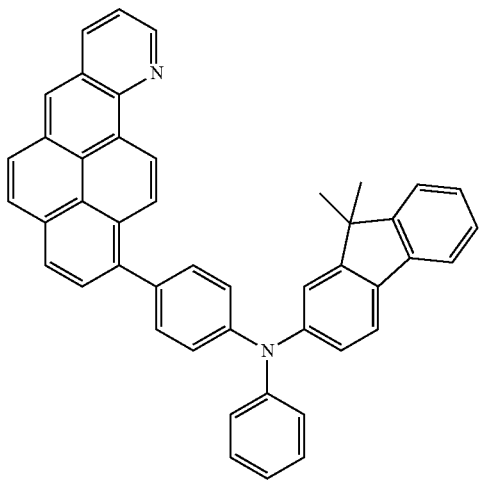
117
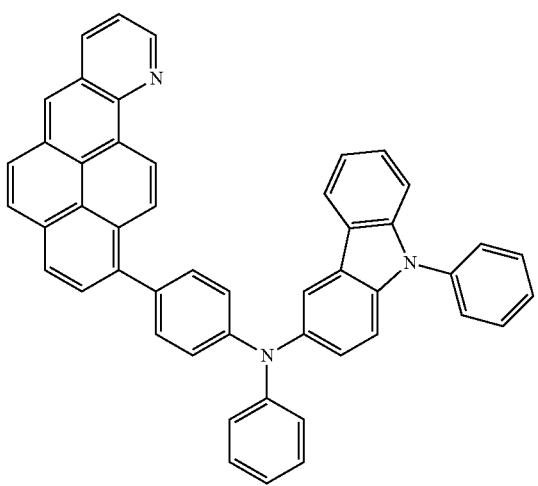

118
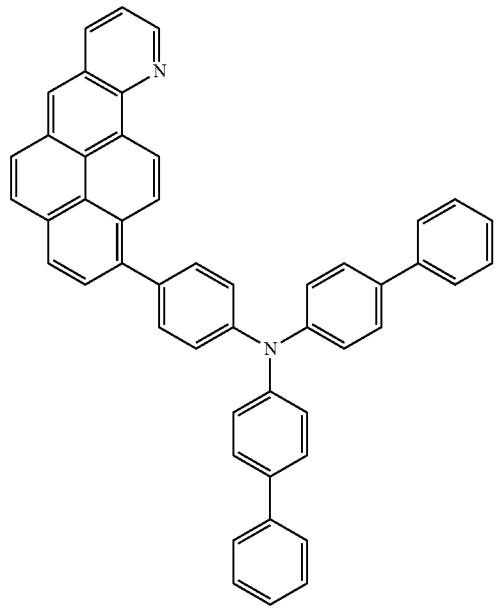
119
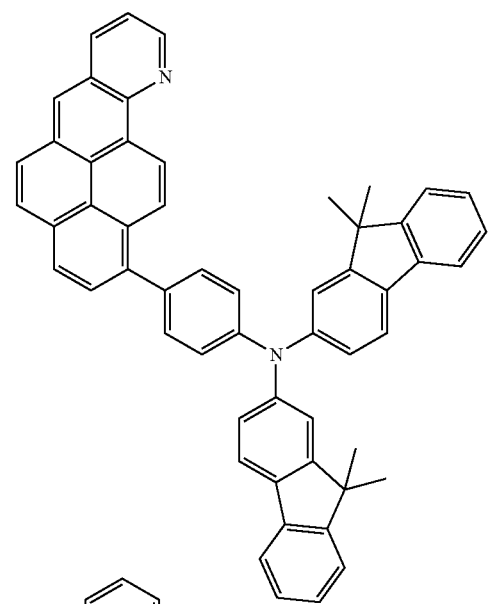
120
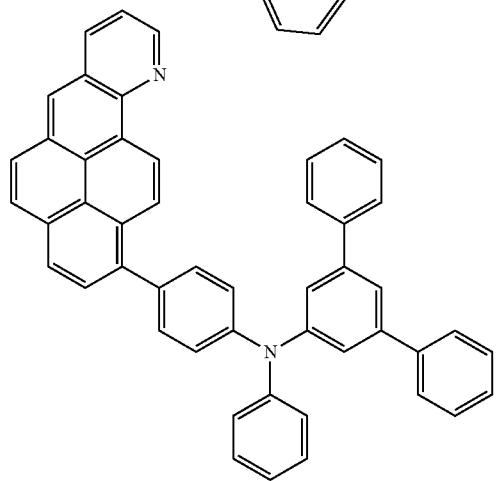
121
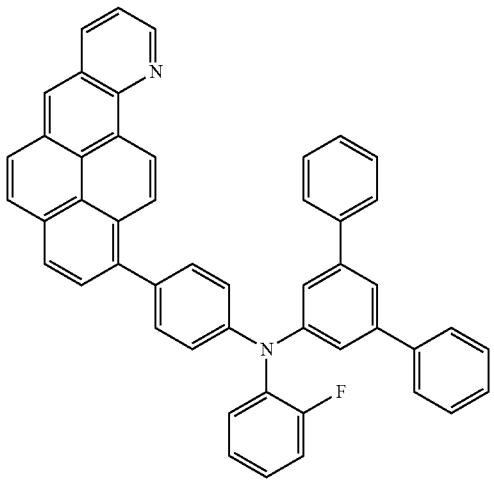
122
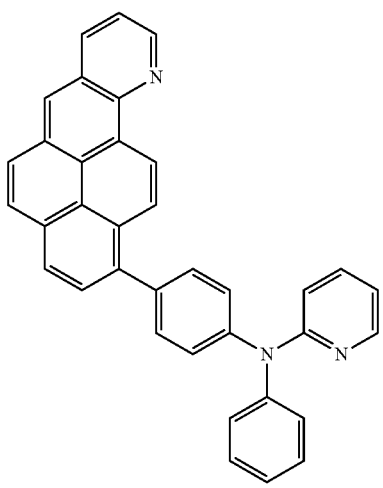
123
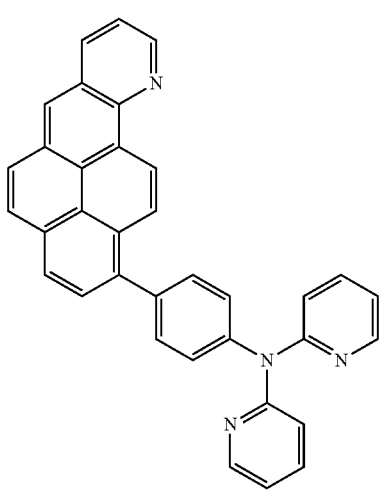

124
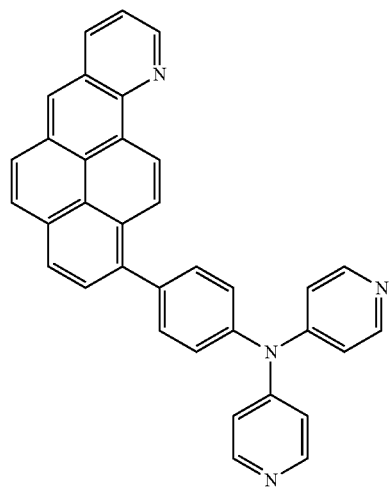
125
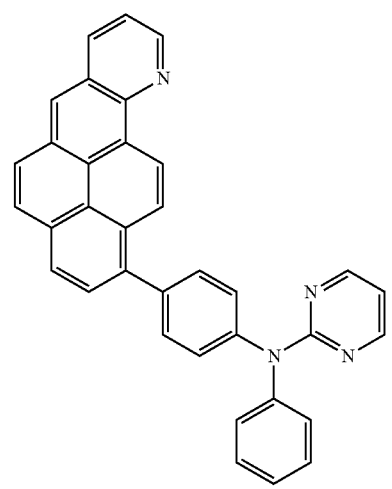
126
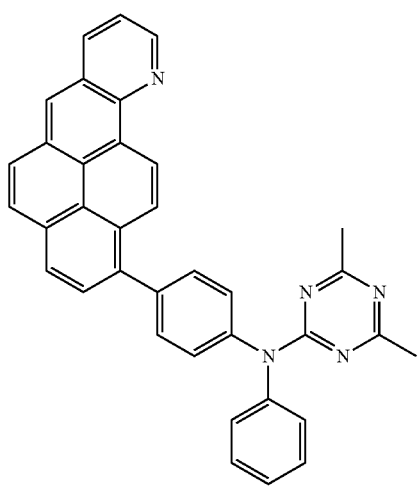
127
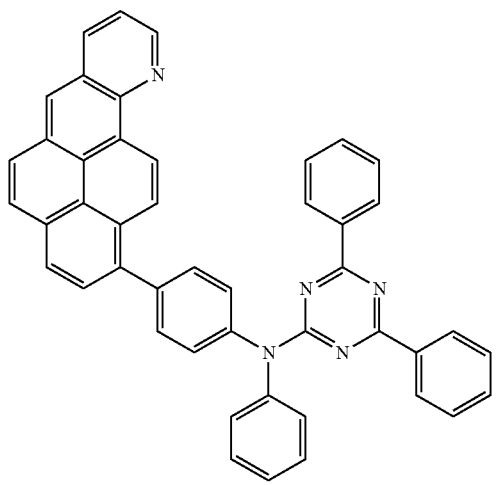
128
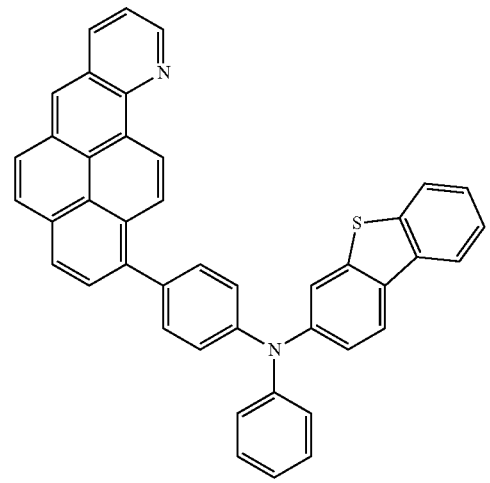
129
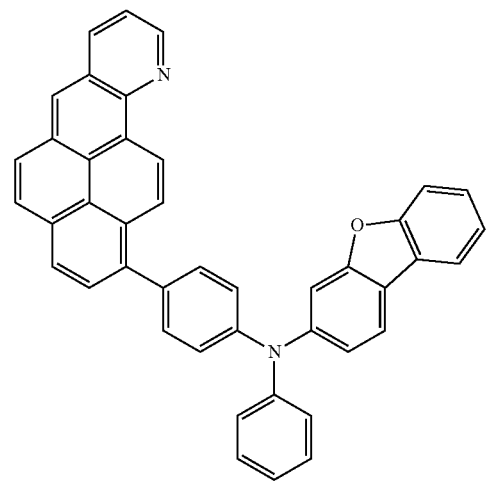

130
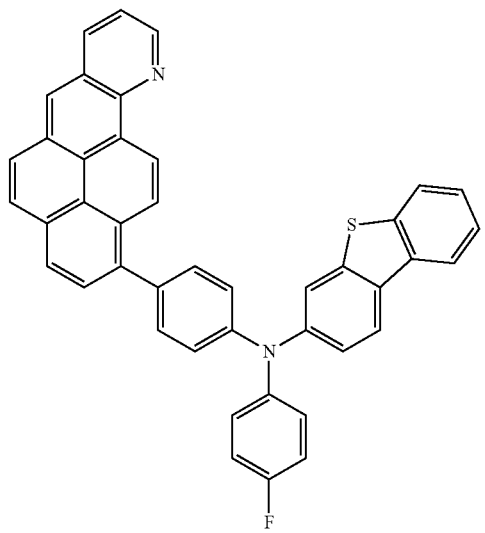
131
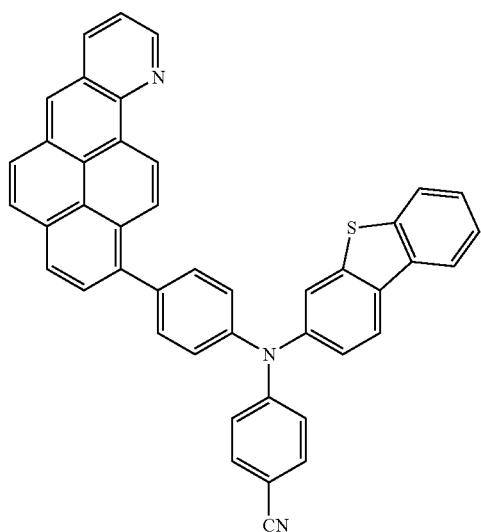
132
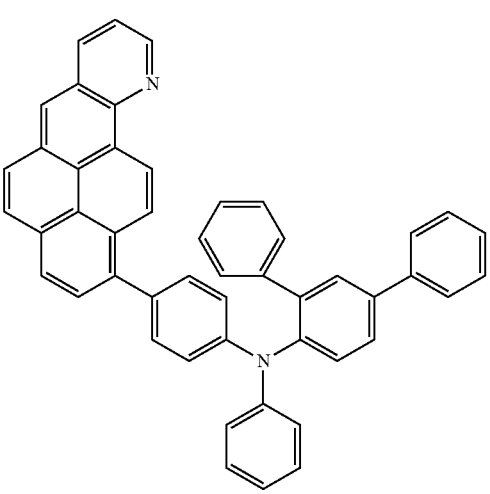
133
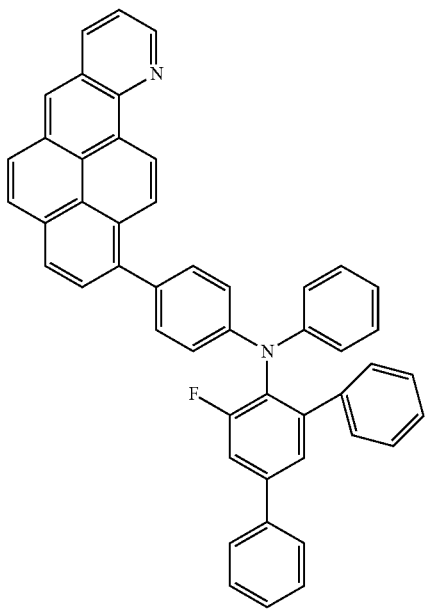
134
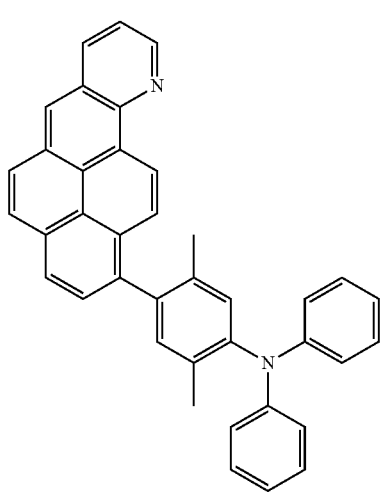
135

136
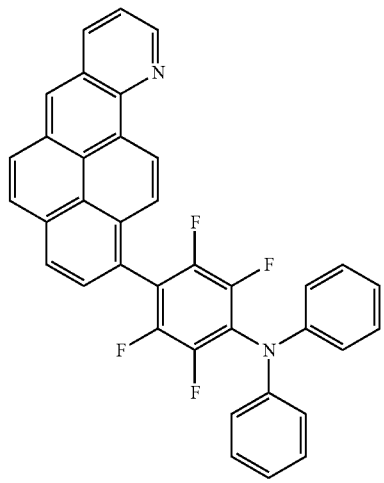
139
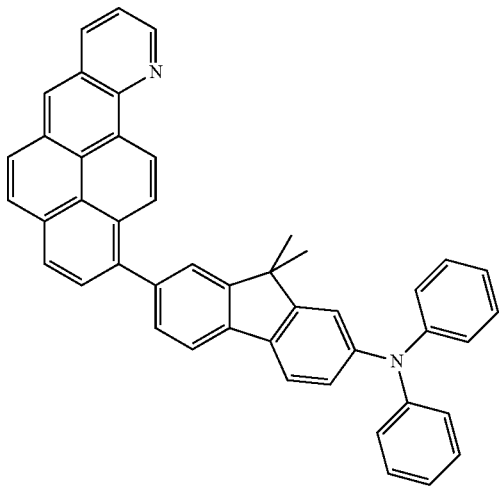
137
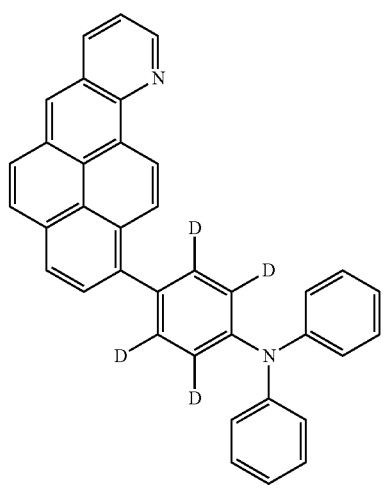
140
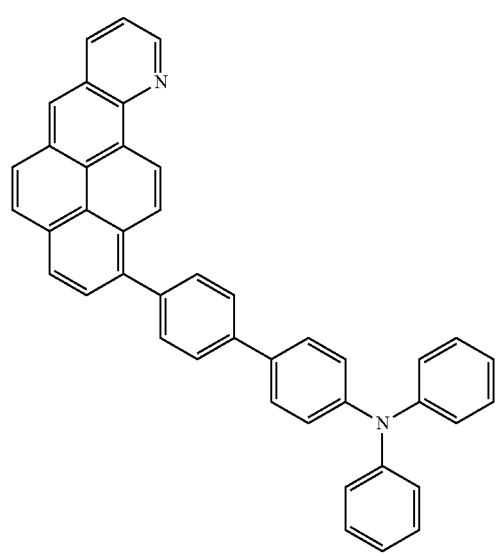
138
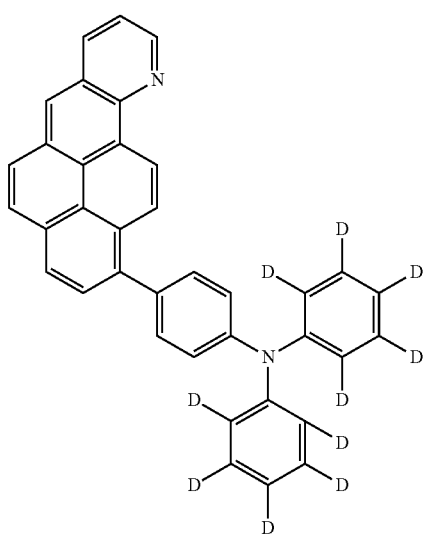
141
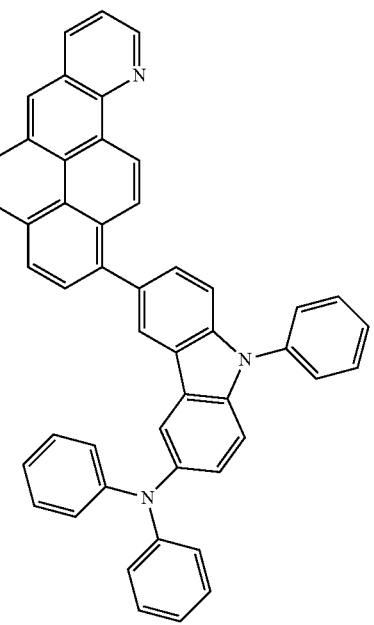

142
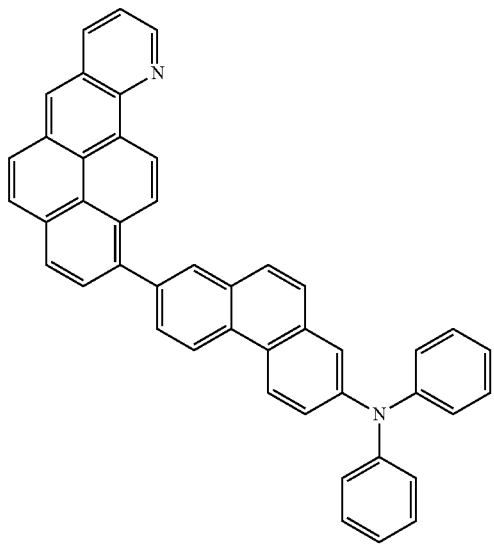
143
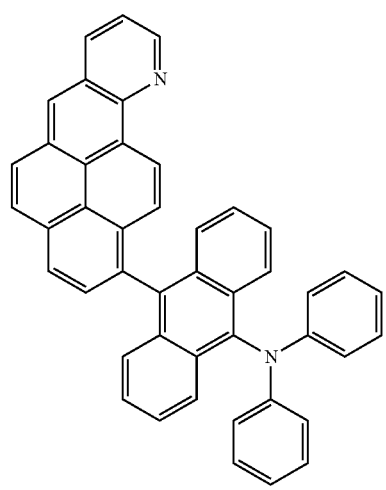
144
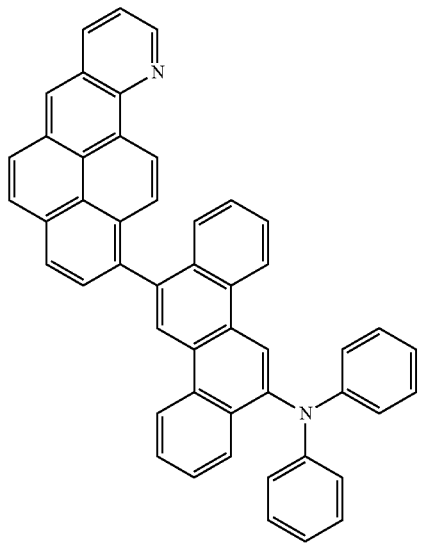
145
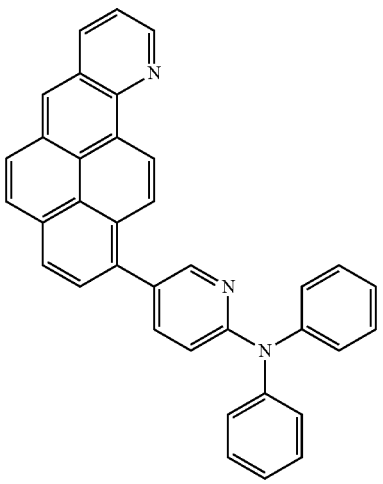
146
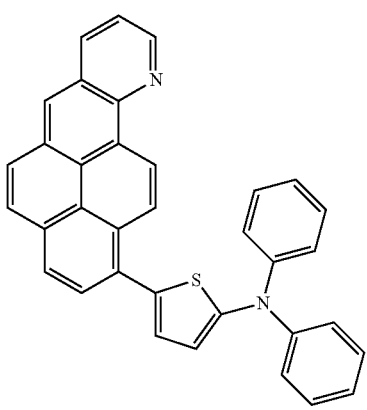
147
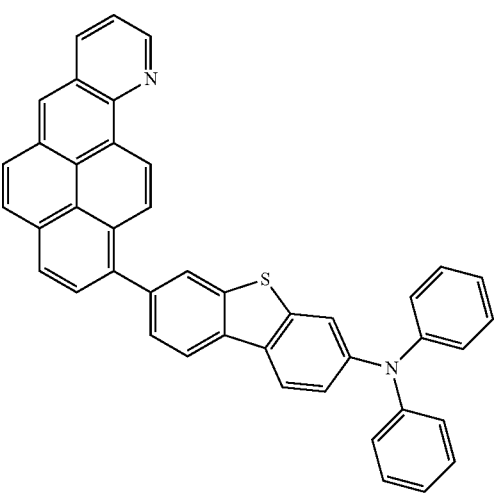

148
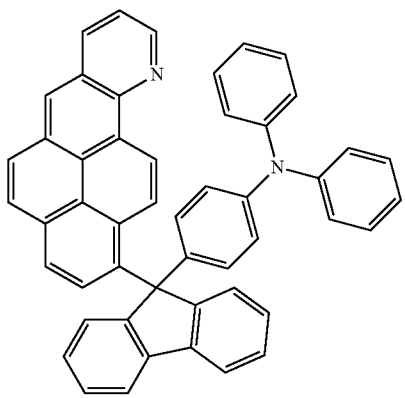
149
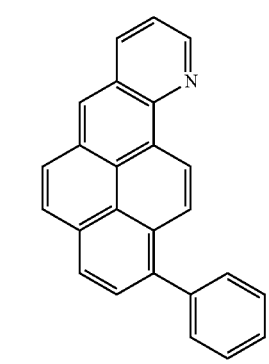
150
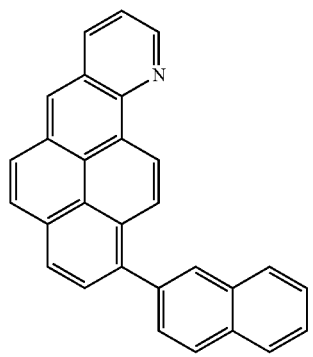
151
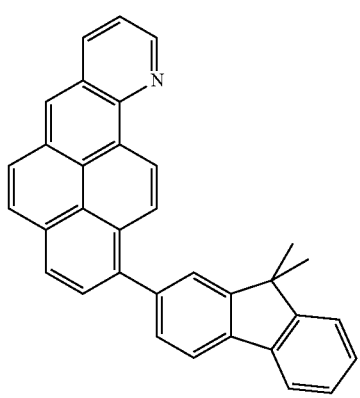
152
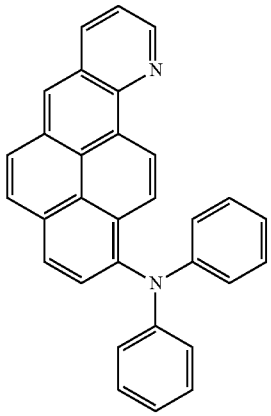
153
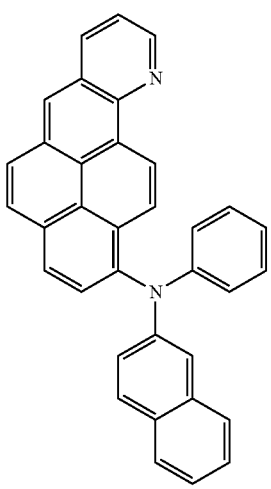
154
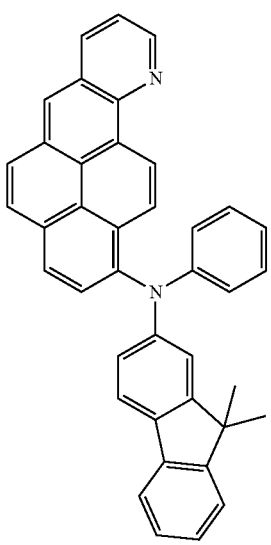

155
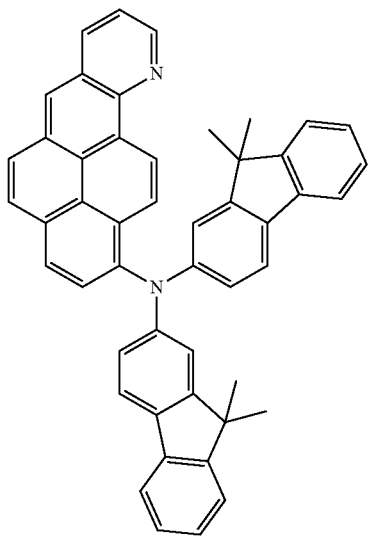

156
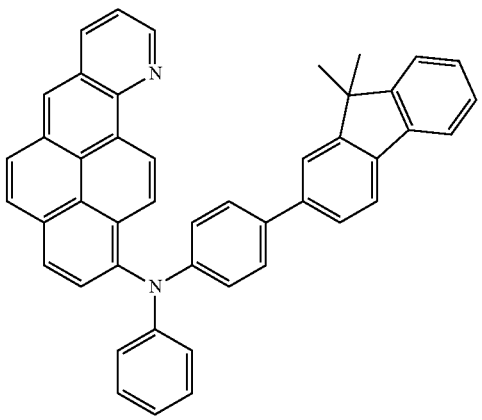

157
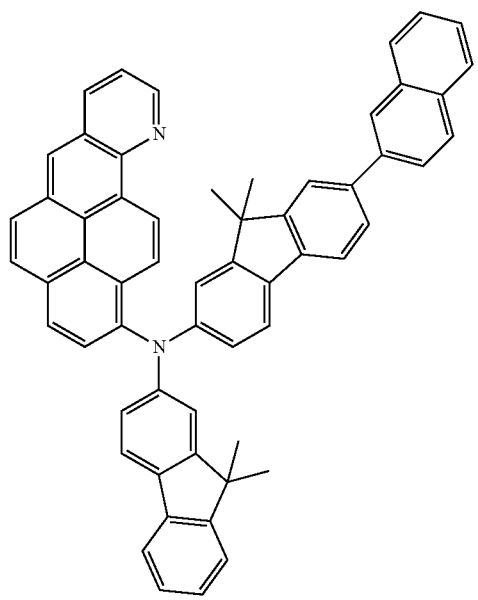

Examples of the unsubstituted $C_1$-$C_{60}$ alkyl group (or $C_1$-$C_{60}$ alkyl group) used herein include methyl, ethyl, propyl, isobutyl, sec-butyl, pentyl, iso-amyl, and hexyl. The substituted $C_1$-$C_{60}$ alkyl group is obtained by substituting at least one hydrogen atom of the unsubstituted $C_1$-$C_{60}$ alkyl group with a heavy hydrogen atom, a halogen atom, a hydroxyl group, a nitro group, a cyano group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_5$-$C_{60}$ aryl group, a $C_2$-$C_{60}$ heteroaryl group, —N($Q_1$)($Q_2$), or —Si($Q_3$)($Q_4$)($Q_5$), wherein $Q_1$ to $Q_5$ are each independently a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, or a $C_2$-$C_{60}$ heteroaryl group.

The unsubstituted $C_1$-$C_{60}$ alkoxy group (or $C_1$-$C_{60}$ alkoxy group) used herein may be represented by —OA, wherein A is an unsubstituted $C_1$-$C_{60}$ alkyl group. Examples of the $C_1$-$C_{60}$ alkoxy group include methoxy, ethoxy, or isopropyloxy, and at least one hydrogen atom of the $C_1$-$C_{60}$ alkoxy group may be substituted with the same substituent groups described above with reference to the substituted $C_1$-$C_{60}$ alkyl group.

The unsubstituted $C_2$-$C_{60}$ alkenyl group (or $C_2$-$C_{60}$ alkenyl group) used herein refers to a hydrocarbon chain having at least one carbon-carbon double bond within or at a terminal of the unsubstituted $C_2$-$C_{60}$ alkyl group. Examples of the $C_2$-$C_{60}$ alkenyl group include ethenyl, propenyl, and butenyl. At least one hydrogen atom in the unsubstituted $C_2$-$C_{60}$ alkenyl group may be substituted with the same substituent groups described above with reference to the substituted $C_1$-$C_{60}$ alkyl group.

The unsubstituted $C_2$-$C_{60}$ alkynyl group (or $C_2$-$C_{60}$ alkynyl group) used herein refers to a hydrocarbon chain having at least one carbon-carbon triple bond within or at a terminal of the unsubstituted $C_2$-$C_{60}$ alkyl group defined above. Examples of the $C_2$-$C_{60}$ alkynyl group include ethynyl and propynyl. At least one hydrogen atom in the unsubstituted $C_2$-$C_{60}$ alkynyl group may be substituted with the same substituent groups described above with reference to the substituted $C_1$-$C_{60}$ alkyl group.

The unsubstituted $C_5$-$C_{60}$ aryl group used herein refers to a monovalent group having a $C_5$-$C_{60}$ carbocyclic aromatic system including at least one aromatic ring. The unsubstituted $C_5$-$C_{60}$ arylene group used herein refers to a divalent group having a $C_5$-$C_{60}$ carbocyclic aromatic system including at least one aromatic ring. If the aryl group and arylene group include at least two rings, they may be fused each other. At least one hydrogen atom in the aryl group and arylene group may be substituted with the same substituent groups described above with reference to the substituted $C_1$-$C_{60}$ alkyl group.

Examples of the unsubstituted or substituted $C_5$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted or unsubstituted $C_5$-$C_{60}$ arylene group may be easily derived from examples of the substituted or unsubstituted $C_5$-$C_{60}$ aryl group.

The unsubstituted $C_2$-$C_{60}$ heteroaryl group is a monovalent group having at least one aromatic ring having at least one of the heteroatoms selected from the group consisting of N, O, P, and S. The unsubstituted $C_2$-$C_{60}$ heteroarylene group is a divalent group having at least one aromatic ring having at least one of the heteroatoms selected from the group consisting of N, O, P, and S. In this regard, when the heteroaryl group and the heteroarylene group have at least two rings, they may be fused each other. At least one hydrogen atom in the heteroaryl group and the heteroarylene group may be substituted with the same substituent groups described above with reference to the substituted $C_1$-$C_{60}$ alkyl group.

Examples of the unsubstituted $C_2$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily derived from examples of the substituted or unsubstituted $C_2$-$C_{60}$ arylene group.

The substituted or unsubstituted $C_5$-$C_{60}$ aryloxy group is —$OA_2$, wherein $A_2$ is a substituted or unsubstituted $C_5$-$C_{60}$ aryl group. The substituted or unsubstituted $C_5$-$C_{60}$ arylthio group is —$OA_3$, wherein $A_3$ is a substituted or unsubstituted $C_5$-$C_{60}$ aryl group.

The condensed-cyclic compound represented by Formula 1 may be synthesized using known organic synthesis methods. The method of synthesizing the condensed-cyclic compound will be obvious to one of ordinary skill in the art with reference examples that will be described later.

The condensed-cyclic compound of Formula 1 may be used in an organic light-emitting diode. Accordingly, an organic light-emitting diode according to an embodiment of present invention includes a first electrode, a second electrode disposed opposite to the first electrode, and a first layer interposed between the first electrode and the second electrode, wherein the first layer includes the condensed-cyclic compound represented by Formula 1.

The condensed-cyclic compound may be contained in the first layer as a single material or a mixture of different materials. That is, the first layer may include at least one of the condensed-cyclic compounds. For example, an organic light-emitting diode prepared in Example 1, which will be described later, includes Compound 14, which is a condensed-cyclic compound and functions as a fluorescent host in an emission layer (EML), alone as the condensed-cyclic compound. Meanwhile, an organic light-emitting diode prepared in Example 7, which will be described later, includes a mixture of Compound 14, which is a condensed-cyclic compound and functions as a fluorescent host in an EML, and Compound 20, which is a condensed-cyclic compound and functions as a fluorescent dopant in the EML, as the condensed-cyclic compounds. The expression "the first layer includes the condensed-cyclic compound as a single material or a mixture of different materials (or the first layer includes at least one of the condensed cyclic compounds)" used herein will be obvious with reference to the descriptions above.

The first layer may include at least one layer selected from the group consisting of a hole injection layer (HIL), a hole transport layer (HTL), a functional layer having both hole injecting and hole transporting capabilities, an electron blocking layer (EBL), an EML, a hole blocking layer (HBL), an electron transport layer (ETL), an electron injection layer (EIL) and a functional layer having both electron transporting and electron injecting capabilities.

The "first layer" used herein refers to a single layer of a plurality of layers interposed between the first electrode and the second electrode of the organic light-emitting diode.

For example, the first layer may include the EML, and the EML may include the condensed-cyclic compound. The condensed-cyclic compound included in the EML may function as a host (a phosphorescent host or a fluorescent host) or as a dopant (a phosphorescent dopant or a fluorescent dopant). For example, the condensed-cyclic compound included in the EML may function as a fluorescent host (refer to Example 1 which will be described later) or as a fluorescent dopant (refer to Example 3 which will be described later).

The EML may comprise two of the condensed-cyclic compounds which are different from each other, one of the two of the condensed-cyclic compounds functions as a host (a phosphorescent host or a fluorescent host) and the other of the two of the condensed-cyclic compounds functions as a dopant (a phosphorescent dopant or a fluorescent dopant). For example, the EML may included two of the condensed-cyclic compounds which are different from each other, one of the two of the condensed-cyclic compounds functions as a fluorescent host and the other of the two of the condensed-cyclic compounds functions as a fluorescent dopant (refer to Example 7 which will be described later).

The first layer may further include the ETL, in addition to the EML. The ETL may include the condensed-cyclic compound which is different from the condensed-cyclic compound included in the EML (refer to Example 8 which will be described later).

Meanwhile, the first layer may include the EML, and the EML may include at least one selected from the group consisting of an anthracene-based compound, a styryl-based compound, and an arylamino-based compound. The EML may be a red, green, or blue EML. For example, the EML may be a blue EML. In this regard, the condensed-cyclic compound may be used as a blue host or a blue dopant to provide an organic light-emitting diode having high efficiency, high brightness, high color purity, and long lifespan.

In addition, the first layer may include the ETL, and the ETL may include the condensed-cyclic compound (refer to Example 5 which will be described later). In this regard, the ETL may further include a metal-containing compound in addition to the condensed-cyclic compound.

The first layer may further include at least one selected from the group consisting of the HIL, the HTL and the functional layer having both hole injecting and hole transporting capabilities, and at least one of the NIL, the HTL and the functional layer having both hole injecting and hole transporting capabilities may further include a charge-generating material in addition to known hole injecting materials, hole transporting materials, and a material having both hole injecting and hole transporting capabilities.

FIG. 1 is a schematic cross-sectional view of an organic light-emitting diode 10 according to an embodiment of the present invention. Hereinafter, the organic light-emitting diode 10 and a method of fabricating the organic light-emitting diode 10 will be described with reference to FIG. 1.

The organic light-emitting diode 10 includes a substrate 11, a first electrode 13, a first layer 15, and a second electrode 17, which are sequentially stacked in this order.

The substrate 11, which may be any substrate that is used in conventional organic light emitting devices, may be a glass substrate or a transparent plastic substrate with excellent mechanical strength, thermal stability, transparency, surface smoothness, ease of handling, and waterproofness.

The first electrode 13 may be formed by depositing or sputtering a material that is used to form the first electrode 13 on the substrate 11. When the first electrode 13 constitutes an anode, the material used to form the first electrode 13 may be a high work-function material so as to facilitate hole injection. The first electrode 13 may be a reflective electrode or a transmission electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first layer 15 is disposed on the first electrode 13. The first layer 15 may include an HIL, an HTL, an EBL, an EML, an HBL, an ETL, and an EIL.

The HIL may be formed on the first electrode 13 by vacuum deposition, spin coating, casting, Langmuir-Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec, but are not limited thereto.

When the HIL is formed using spin coating, the coating conditions may vary according to a compound that is used to form the HIL, and structure and thermal properties of the HIL to be formed. For example, the coating conditions may include a coating speed of about 2000 rpm to about 5000 rpm, and a thermal treatment temperature of about 80° C. to about 200° C., wherein the thermal treatment is for removing a solvent after coating. However, the coating conditions are not limited thereto.

The HIL may be formed of the condensed-cyclic compound represented by Formula 1 and/or any material that is commonly used to form a HIL. Examples of known materials that may be used to form the HIL include, but are not limited to, N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and polyaniline/poly(4-styrene-sulfonate (PANI/PSS).

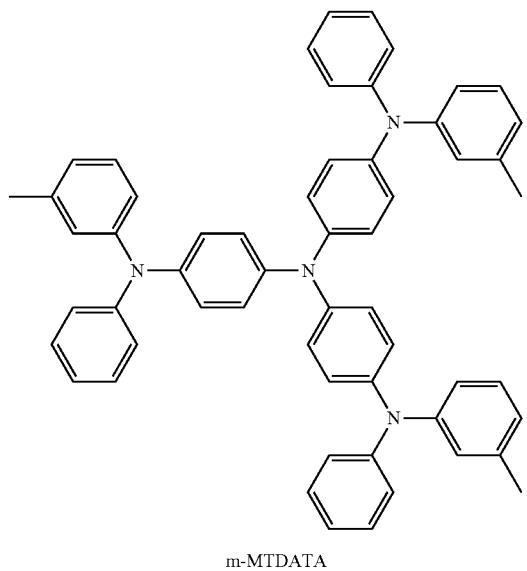

m-MTDATA

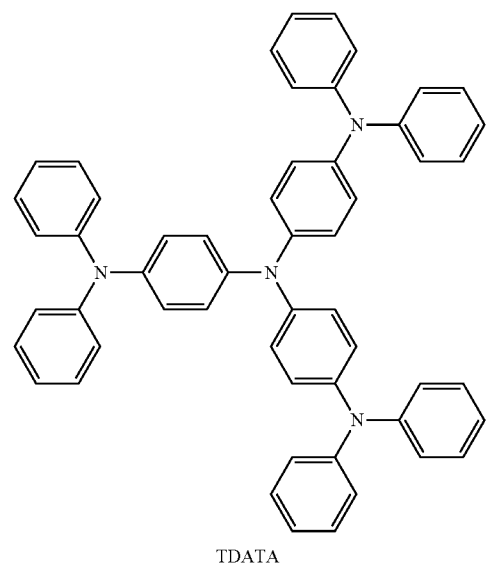

TDATA

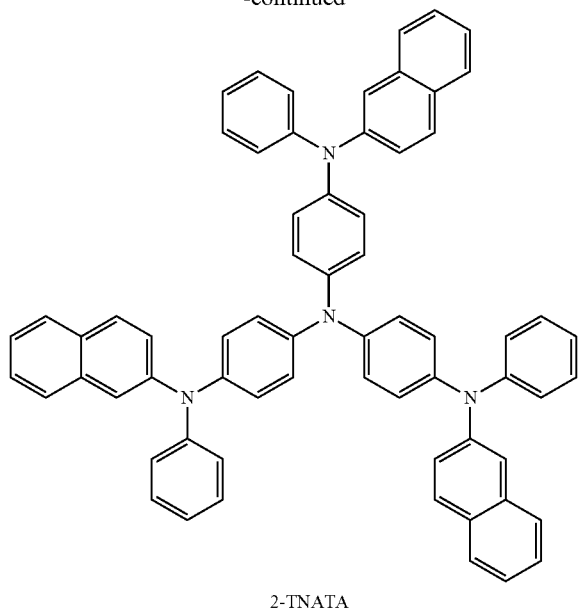

2-TNATA

The thickness of the HIL may be about 100 to about 10,000 Å, and for example, about 100 to about 1,000 Å. When the thickness of the HIL is within this range, the HIL may have excellent hole injecting ability without a substantial increase in driving voltage.

Then, the HTL may be formed on the HIL by using vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used to form the HTL.

The HTL may be formed of the condensed-cyclic compound represented by Formula 1 and/or any known hole transporting material. Examples of the known hole transporting material include a carbazole derivative such as N-phenylcarbazole and polyvinyl carbazole, N,N'-bis(3-methylphenyl)-N,N'-diphenyl-[1,1-biphenyl]-4,4'-diamine (TPD), a triphenylamine-based material such as 4,4',4"-tris(N-carbazolyl)triphenylamine (TCTA), and N,N'-di(1-naphthyl)-N,N'-diphenylbenzidine (NPB), but are not limited thereto.

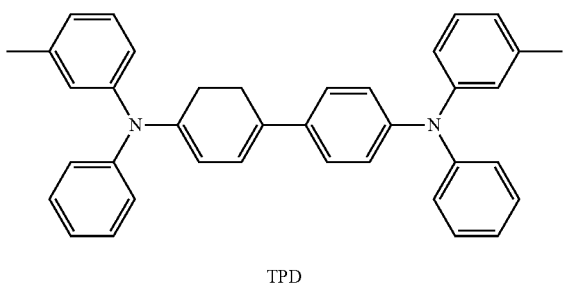

TPD

The thickness of the HTL may be in a range of about 50 to about 1,000 Å, for example, about 100 to about 800 Å. When the thickness of the HTL is within this range, the HTL may have excellent hole transporting ability without a substantial increase in driving voltage.

Alternatively, the functional layer having both hole injecting and hole transporting capabilities may be formed instead of the HIL and the HTL. The functional layer having both hole injecting and hole transporting capabilities may include any material that is commonly used in the art.

At least one of the HIL, the HTL and the functional layer having both hole injecting and hole transporting capabilities may further include a charge-generating material in addition to the condensed-cyclic compound represented by Formula 1, known hole injecting materials, known hole transporting materials, and/or materials having both hole injecting and hole transporting capabilities, in order to improve conductivity of the layers.

The charge-generating material may be a p-dopant. Examples of the p-dopant include a quinine derivative such as tetracyanoquinonedimethane (TCNQ) and 2,3,5,6-tetrafluorotetracyano-1,4-benzoquinonedimethane (F4TCNQ); a metal oxide such as tungsten oxide and molybdenum oxide; and a cyano group-containing compound such as Compound 200 below, but are not limited thereto.

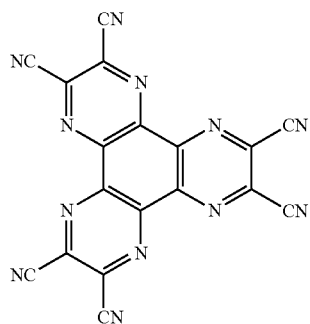

Compound 200

If the HIL, the HTL, or the functional layer having both hole injecting and hole transporting capabilities further includes the charge-generating material, the charge-generating material may be homogeneously or non-homogeneously dispersed in these layers.

The EML may be formed on the HTL or the functional layer having both hole injecting and hole transporting capabilities by vacuum deposition, spin coating, casting, LB deposition, or the like. When the EML is formed by using vacuum deposition or spin coating, the deposition and coating conditions may be similar to those used to form the HIL, although the deposition and coating conditions may vary according to a compound that is used to form the EML.

The material for forming the EML may include at least one of the condensed-cyclic compounds represented by the Formula 1 and/or known light-emitting materials including a host and a dopant.

Examples of known host include tris(8-quinolinolate)aluminum (Alq3), 4,4'-N,N'-dicarbazole-biphenyl (CBP), poly (n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

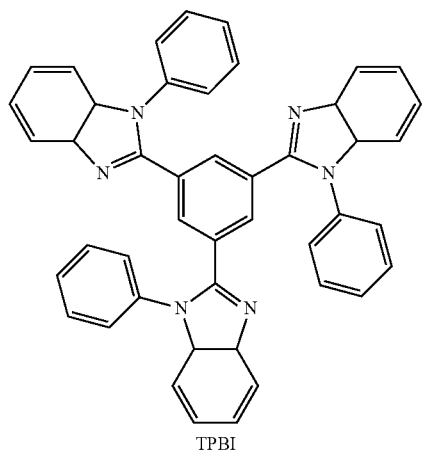
TPBI

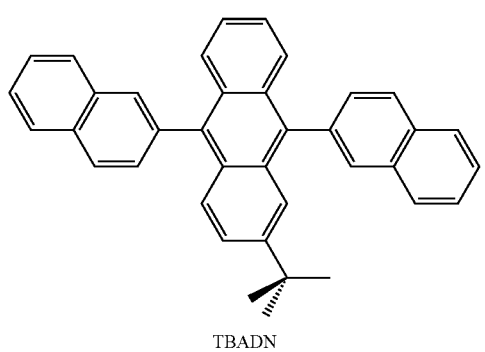
TBADN

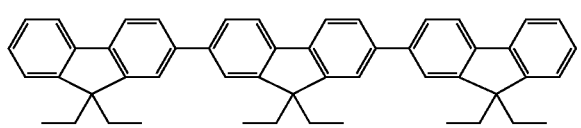
E3

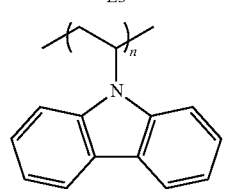
PVK

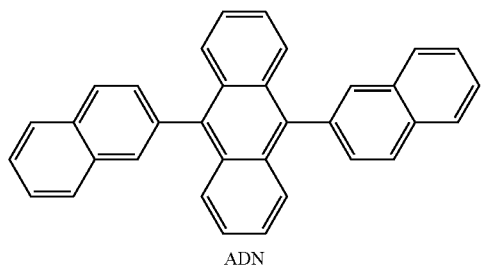
ADN

The dopant may include at least one of a fluorescent dopant and a phosphorescent dopant. The phosphorescent dopant may be an organic metal complex including Ir, Pt, Os, Re, Ti, Zr, Hf, or any combination of at least two thereof, but is not limited thereto.

Meanwhile, examples of known red dopants include PtOEP, Ir(piq)$_3$, and Btp$_2$Ir(acac), but are not limited thereto.

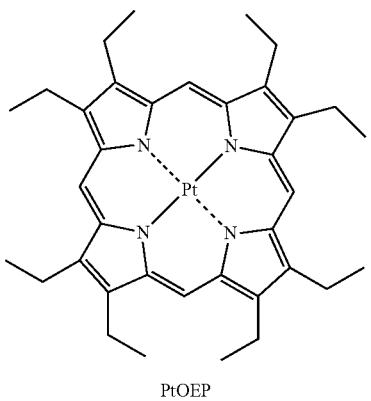
PtOEP

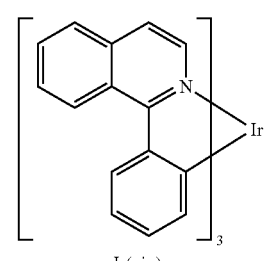
Ir(piq)$_3$

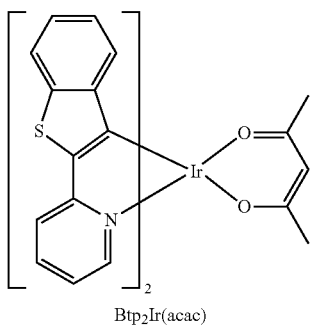
Btp$_2$Ir(acac)

Examples of known green dopants include Ir(ppy)$_3$ (where "ppy" denotes phenylpyridine), Ir(ppy)$_2$(acac), Ir(mpyp)$_3$, and C545T, but are not limited thereto.

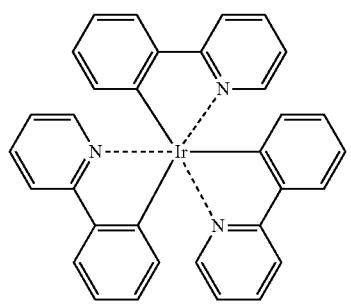
Ir(ppy)$_3$

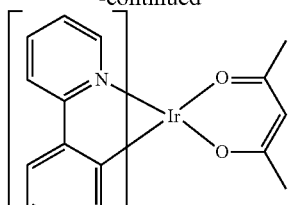
Ir(ppy)₂(acac)
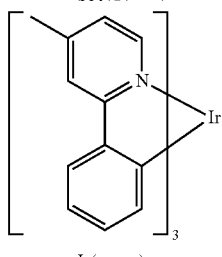
Ir(mpyp)₃
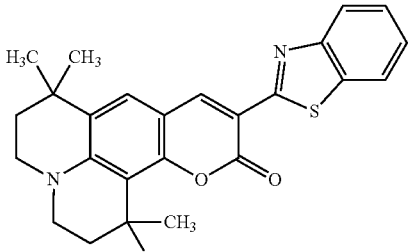
C545T
Examples of well-known blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), DPVBi, but are not limited thereto.
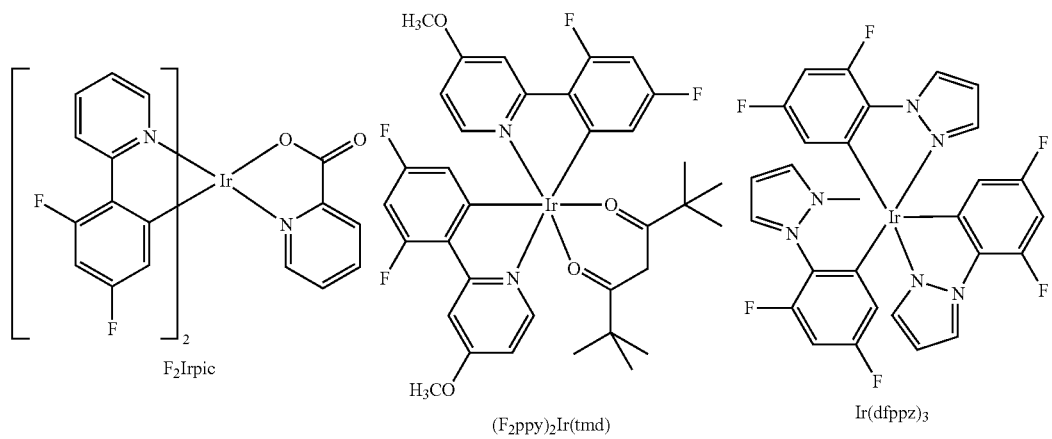
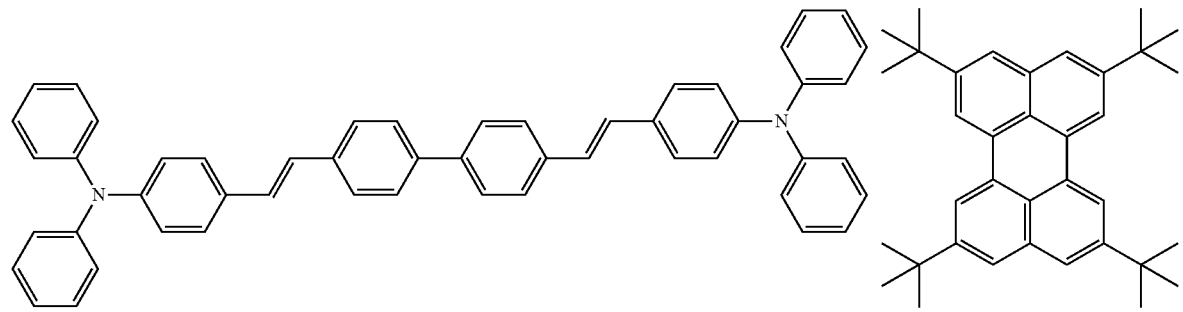
DPAVBi
TBPe
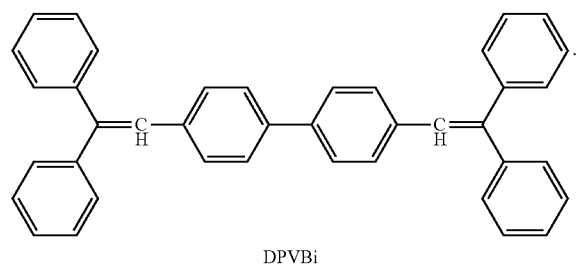
DPVBi If the EML include a host and a dopant, the amount of the dopant may be in the range of about 0.01 to about 15 parts by weight based on 100 parts by weight of the host, but is not limited thereto.

The thickness of the EML may be in the range of about 100 Å to about 1,000 Å, for example, about 200 Å to about 600 Å. When the thickness of the EML is within this range, the EML may have excellent light emitting ability without a substantial increase in driving voltage.

When a phosphorescent dopant is also used to form the EML, the HBL may be formed between the HTL and the EML by using vacuum deposition, spin coating, casting, LB deposition, or the like, in order to prevent diffusion of triplet excitons or holes into an ETL. When the HBL is formed using vacuum deposition or spin coating, the conditions for deposition and coating may be similar to those for the formation of the HIL, although the conditions for deposition and coating may vary according to a material that is used to form the HBL. Any material that is commonly used to form a HBL may be used. Examples of materials for forming the HBL include an oxadiazole derivative, a triazole derivative, and a phenanthroline derivative.

The thickness of the HBL may be in a range of about 50 to about 1,000 Å, for example, about 100 to about 300 Å. When the thickness of the HBL is within this range, the HBL may have excellent hole blocking ability without a substantial increase in driving voltage.

Next, the ETL may be formed on the HBL or EML using a method such as vacuum deposition, spin coating, or casting. When the ETL is formed using vacuum deposition or spin coating, the deposition and coating conditions may be similar to those for the formation of the HIL, although the deposition and coating conditions may vary according to a compound that is used to form the ETL. A material that is used to form the ETL may be the condensed-cyclic compound represented by Formula 1 or a material that can stably transport electrons injected from the electron injecting electrode (cathode), and any known material may be used. Examples of known ETL material include quinoline derivatives, such as Alq3(Tris(8-hydroxyquinolinato)aluminium), TAZ, and beryllium bis(benzoquinolin-10-olate) (Balq$_2$), but are not limited thereto.

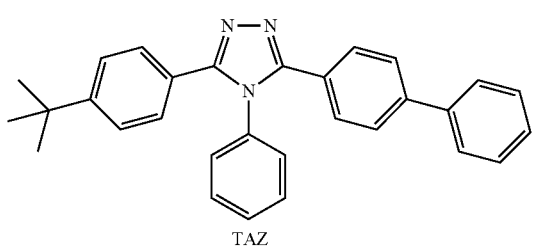

TAZ

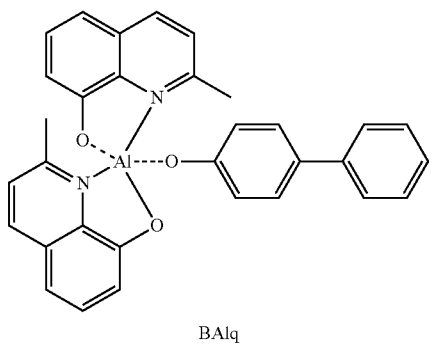

BAlq

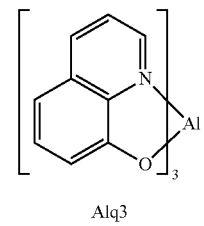

Alq3

The thickness of the ETL may be in the range of about 100 Å to about 1,000 Å, for example, about 150 Å to about 500 Å. When the thickness of the ETL is within the range described above, the ETL may have excellent electron transporting ability without a substantial increase in driving voltage.

The ETL may include an electron-transporting organic compound and a metal-containing material. Examples of the electron-transporting compound include AND, and anthracene-based compounds such as Compounds 201 and 202 below, but are not limited thereto.

Compound 201

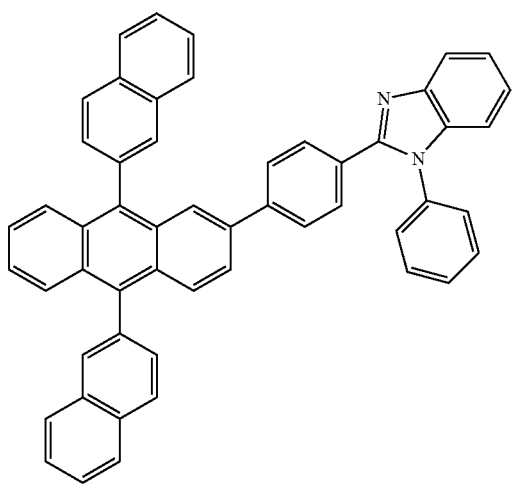

Compound 202

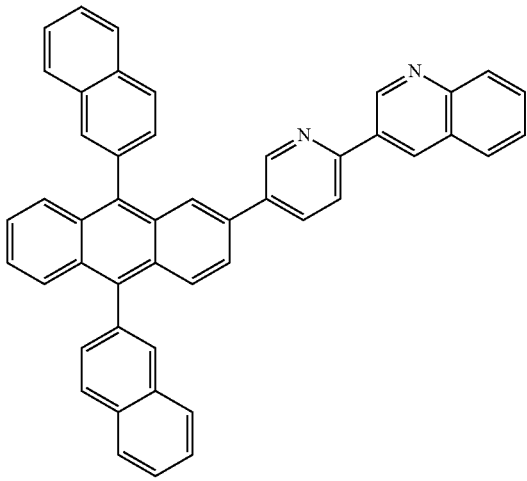

The metal-containing material may include a Li complex. Examples of the Li complex include lithium quinolate (LiQ) or Compound 203 below, but are not limited thereto.

Compound 203

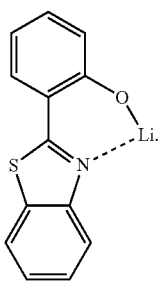

In addition, the EIL may be formed on the ETL using any material that allows electrons to be easily injected from the cathode.

Examples of materials for forming the EIL include LiF, NaCl, CsF, $Li_2O$, and BaO, which are known in the art. The conditions for deposition of the EIL are similar to those for the formation of the HIL, although the deposition conditions may vary according to a material that is used to form the EIL.

The thickness of the EIL may be in the range of about 1 to about 100 Å, for example, in the range of about 3 to about 90 Å. When the thickness of the EIL is within this range, the EIL may have excellent electron injecting ability without a substantial increase in driving voltage.

The second electrode 17 is disposed on the first layer 15. The second electrode 17 may be a cathode, which is an electron injecting electrode. A material for forming the second electrode 17 may be a metal, an alloy, an electrically conductive compound, which have a low-work function, or a mixture thereof. In this regard, the second electrode 17 may be a transmissive electrode formed of lithium (Li), magnesium (Mg), aluminum (Al), aluminum (Al)-lithium (Li), calcium (Ca), magnesium (Mg)-indium (In), magnesium (Mg)-silver (Ag), or the like. Meanwhile, in order to manufacture a top-emission type organic light-emitting diode, a transmissive electrode formed of ITO or IZO may be used.

Hereinafter, one or more embodiments will be described in detail with reference to the following examples. These examples are not intended to limit the purpose and scope of the one or more embodiments of the present invention.

EXAMPLES

Synthesis Example 1

Synthesis of Compound 14

Compound 14 was synthesized through Reaction Scheme 1 below:

Reaction Scheme 1

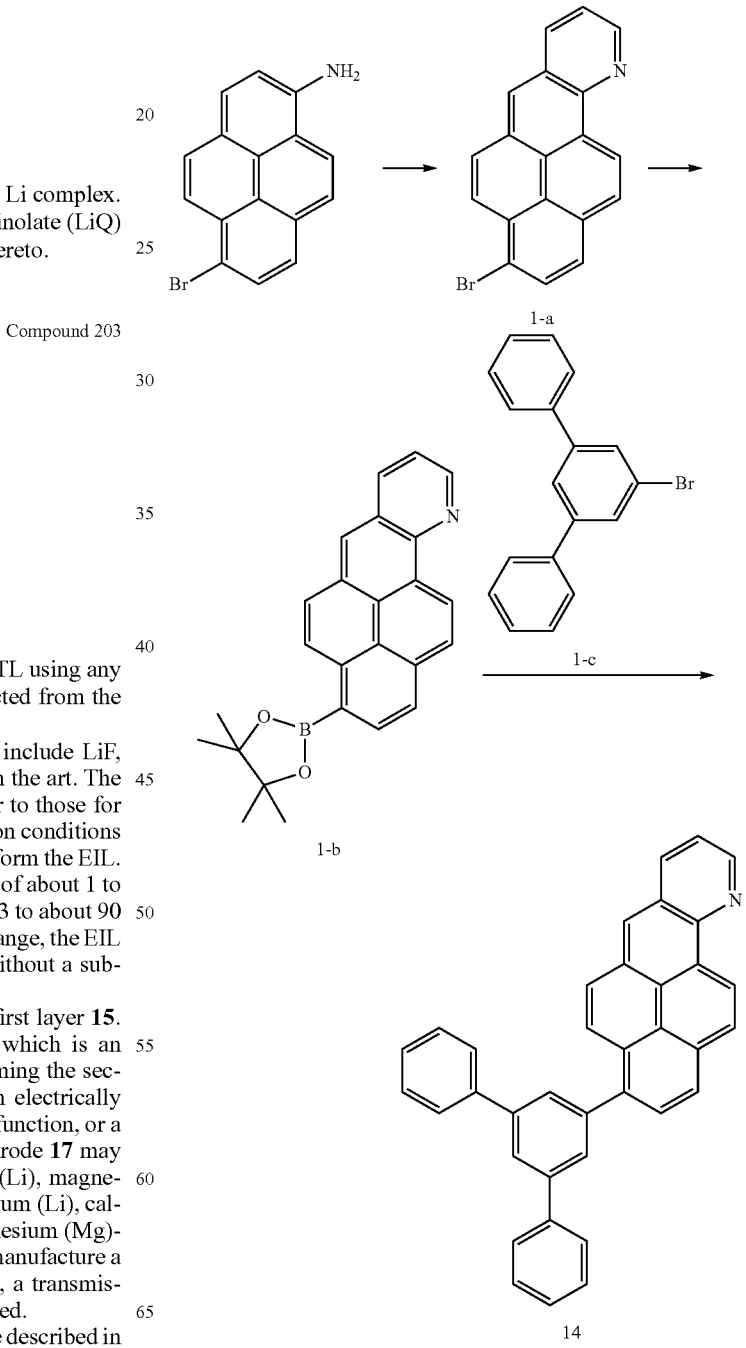

Synthesis of Intermediate 1-a 10 g (33.8 mmol) of 1-amino-6-bromopyrene, 10 g of a 70% sulfuric acid solution were added to 8 g of nitrobenzene. The mixture was heated to 110° C., and 10 g of glycerol, as an oxidant, was added thereto. Then, the mixture was stirred at 110° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 7.1 g of Intermediate 1-a (Yield: 71%). The produced compound was identified using LC-MS.

$C_{19}H_{10}Br_1N_1$: M+: 331.00

Synthesis of Intermediate 1-b 5 g (15 mmol) of Intermediate 1-a, 4.6 g (18 mmol) of bis(pinacolato)diboron, 4.42 g (45 mmol) of potassium acetate (KOAc), and 0.04 g (0.06 mmol) of 1,1'-bis(diphenylphosphino)ferrocene]dichloropalladium(II) (Pd(dppf)Cl$_2$) were mixed with 100 mL of degassed DMF. Then, the mixture was stirred for 10 hours. The mixture was subjected to extraction three times with 100 mL of water and 100 mL of dichloromethane. An organic layer was collected and dried using magnesium sulfate to evaporate the solvent. The residue was separately purified using silica gel column chromatography to obtain 5.18 g of Intermediate 1-b (Yield: 91%). The produced compound was identified using LC-MS.

$C_{25}H_{22}B_1N_1O_2$: M+379.17

Synthesis of Compound 14

2 g (5.2 mmol) of Intermediate 1-b, 1.9 g (6.2 mmol) of Intermediate 1-c, and 0.18 g (0.16 mmol) of tetrakis(triphenylphosphin)palladium (O) (Pd(PPh$_3$)$_4$) were mixed with 20 mL of a 2M NaOH solution and 20 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.8 g of Compound 14 (Yield: 73%). The produced compound was identified using LC-MS and NMR.

$C_{37}H_{23}N_1$: M+482.19

$^1$H NMR (CDCl$_3$, 400 MHz) δ (ppm) 9.07 (d, 1H) 8.90 (m, 1H) 8.36 (d, 1H) 8.29 (s, 1H) 8.26-8.23 (m, 1H) 8.20 (d, 1H) 8.14 (d, 1H) 8.01 (d, 11-1) 7.96 (d, 1H) 7.85 (m, 2H) 7.72-7.69 (m, 5H) 7.49-7.39 (m, 7H).

Synthesis Example 2

Synthesis of Compound 20

Compound 20 was synthesized through Reaction Scheme 2 below:

Reaction Scheme 2

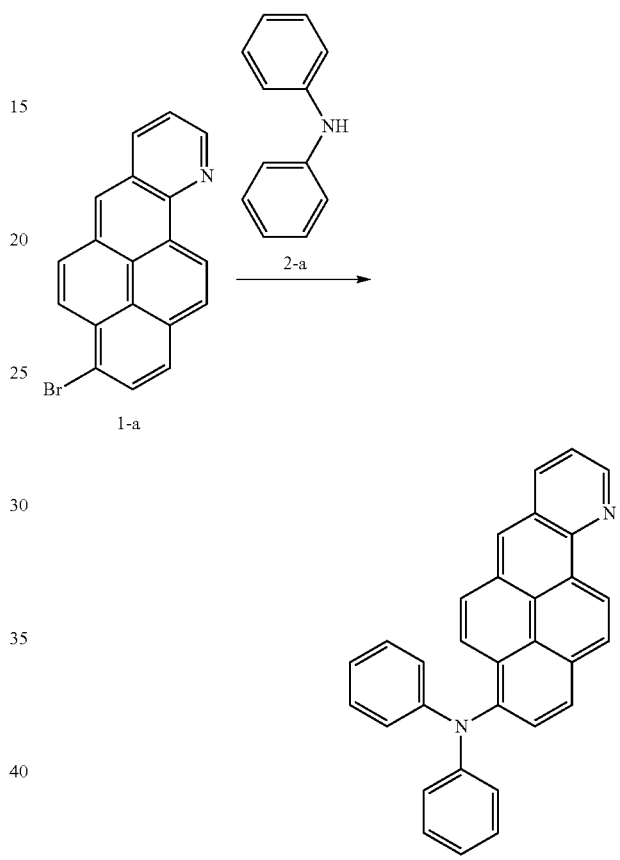

2 g (6.0 mmol) of Intermediate 1-a prepared according to Synthesis Example 1, 10.15 g (60.0 mmol) of Intermediate 2-a, 0.16 g (0.18 mmol) of tris(dibenzylidine acetone)dipalladium (O) (Pd$_2$(dba)$_3$), 0.05 g (0.18 mmol) of (2,4,6-tri-tert-butylphenyl)phosphine, and 0.7 g (7.2 mmol) of sodium t-butoxide were added to 100 mL of toluene. The mixture was refluxed at 100° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.19 g of Compound 20 (Yield: 47%). The produced compound was identified using LC-MS and NMR.

$C_{31}H_{20}N_2$: M+420.16

$^1$H NMR (CDCl$_3$, 400 MHz) δ (ppm) 8.91 (m, 1H) 8.69 (d, 1H) 8.27-8.24 (m, 2H) 8.08 (d, 1H) 8.03 (d, 1H) 7.91-7.02 (m, 14H).

Synthesis Example 3

Synthesis of Compound 22

Compound 22 was synthesized through Reaction Scheme 3 below:

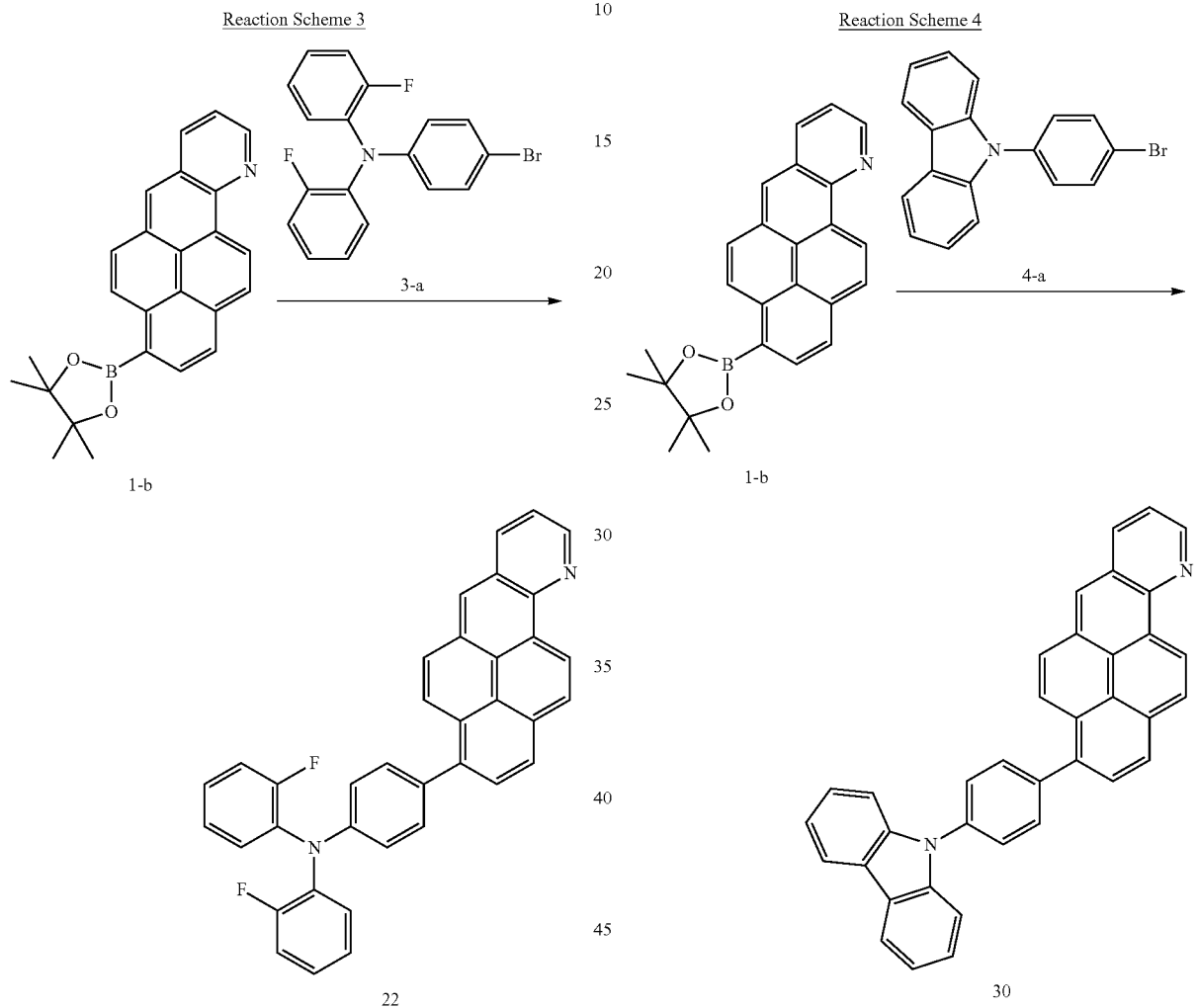

2 g (5.2 mmol) of Intermediate 1-b, 2.23 g (6.2 mmol) of Intermediate 3-a, and 0.18 g (0.16 mmol) of Pd(PPh$_3$)$_4$ were mixed with 20 mL of a 2M NaOH solution and 20 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.7 g of Compound 22 (Yield: 62%). The produced compound was identified using LC-MS and NMR.

$C_{33}H_{23}N_2$: M+532.18

$^1$H NMR (CDCl$_3$, 400 MHz) δ (ppm) 9.07 (d, 1H) 8.91 (m, 1H) 8.63 (d, 1H) 8.49 (s, 1H) 8.47-8.44 (m, 1H) 8.36 (d, 1H) 8.23 (d, 2H) 8.19 (d, 1H) 7.84-7.81 (m, 2H) 7.75-7.71 (m, 1H) 7.44-7.23 (m, 8H) 6.99 (m, 2H).

Synthesis Example 4

Synthesis of Compound 30

Compound 30 was synthesized through Reaction Scheme 4 below:

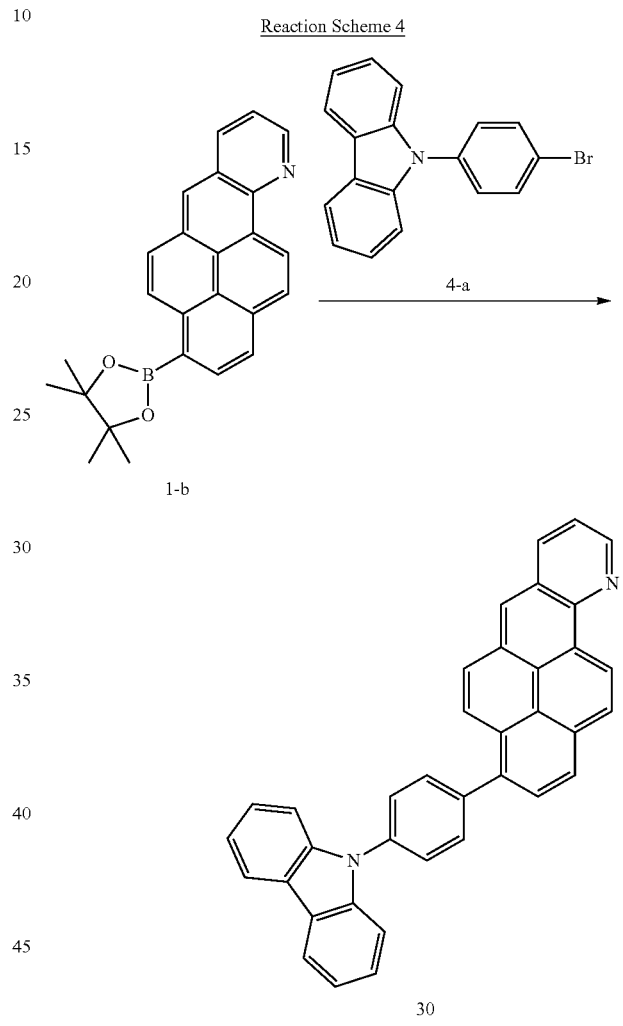

2 g (5.2 mmol) of Intermediate 1-b, 2.0 g (6.2 mmol) of Intermediate 4-a, and 0.18 g (0.16 mmol) of Pd(PPh$_3$)$_4$ were mixed with 20 mL of a 2M NaOH solution and 20 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.98 g of Compound 30 (Yield: 77%). The produced compound was identified using LC-MS and NMR.

$C_{37}H_{22}N_2$: M+494.18

$^1$H NMR (CDCl$_3$, 400 MHz) δ (ppm) 9.07 (d, 1H) 8.91-8.90 (m, 1H) 8.42 (d, 1H) 8.29 (s, 1H) 8.26-8.23 (m, 1H) 8.17 (d, 1H) 8.12-8.10 (m, 2H) 8.04-8.00 (m, 2H) 7.89 (d, 1H) 7.61-7.57 (m, 2H) 7.45-7.25 (m, 9H).

Synthesis Example 5

Synthesis of Compound 31

Compound 31 was synthesized through Reaction Scheme 5 Below

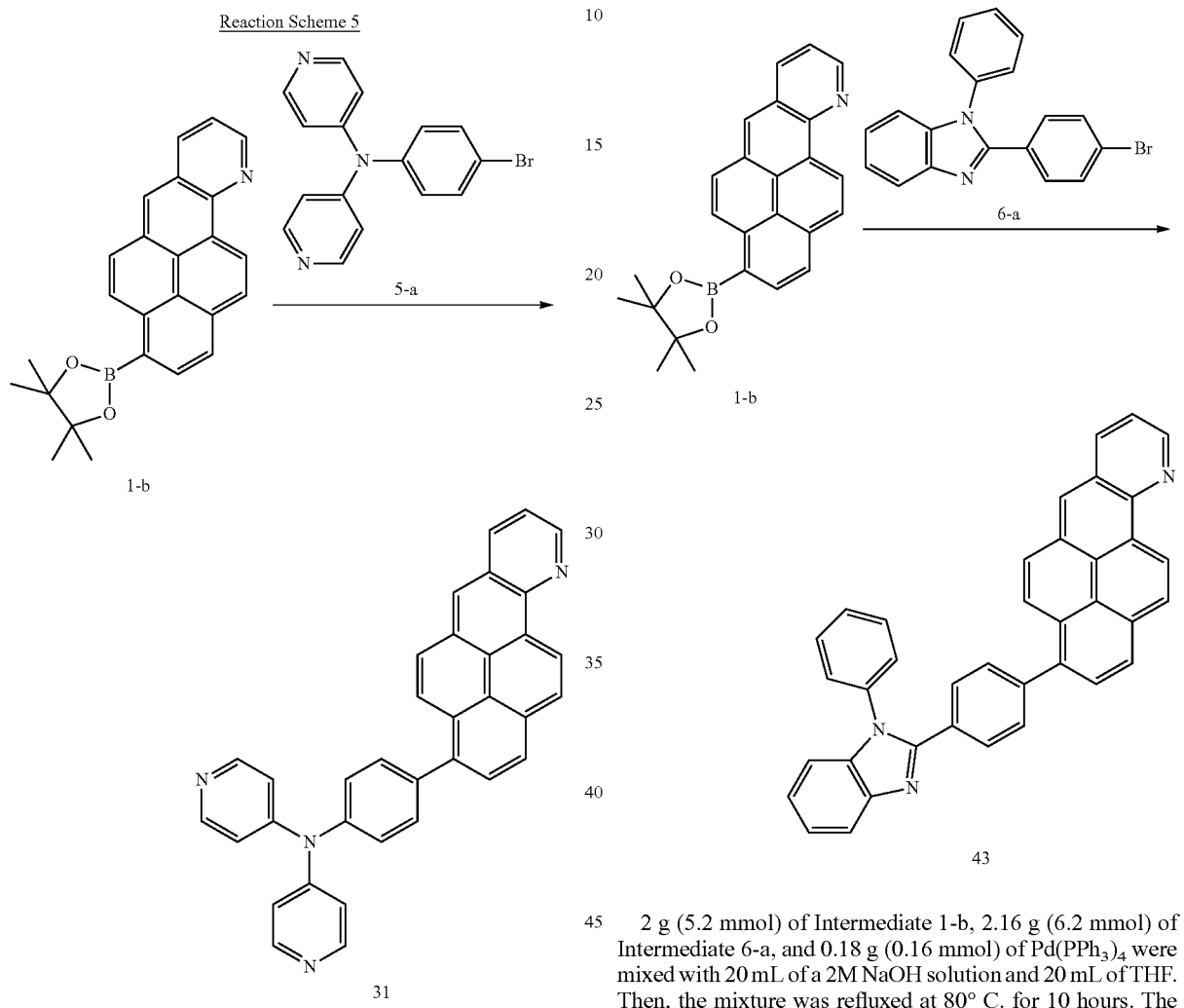

2 g (5.2 mmol) of Intermediate 1-b, 2.02 g (6.2 mmol) of Intermediate 5-a, and 0.18 g (0.16 mmol) of Pd(PPh$_3$)$_4$ were mixed with 20 mL of a 2M NaOH solution and 20 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 2.1 g of Compound 31 (Yield: 81%). The produced compound was identified using LC-MS and NMR.

$C_{36}H_{23}N_3$: M+498.19

$^1$H NMR (CDCl$_3$, 400 MHz) δ (ppm) 9.07 (d, 1H) 8.91 (m, 1H) 8.46 (m, 4H) 8.42 (d, 1H) 8.29 (s, 1H) 8.25 (m, 1H) 8.16 (d, 1H) 8.04-8.00 (m, 2H) 7.89 (d, 1H) 7.52-7.49 (m, 2H) 7.45-7.41 (m, 1H) 7.25-7.21 (m, 2H) 7.11 (m, 4H).

Synthesis Example 6

Synthesis of Compound 43

Compound 43 was synthesized through Reaction Scheme 6 below:

Reaction Scheme 6

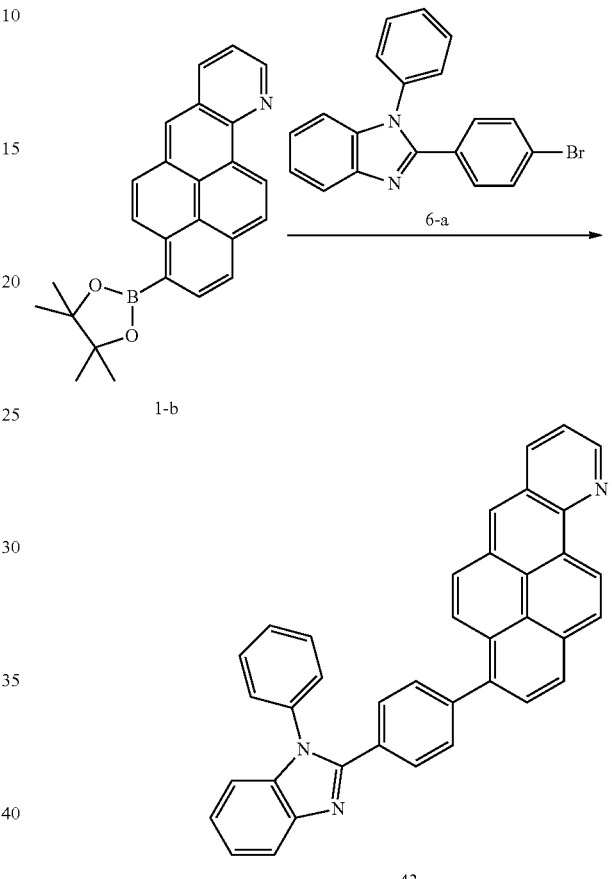

2 g (5.2 mmol) of Intermediate 1-b, 2.16 g (6.2 mmol) of Intermediate 6-a, and 0.18 g (0.16 mmol) of Pd(PPh$_3$)$_4$ were mixed with 20 mL of a 2M NaOH solution and 20 mL of THF. Then, the mixture was refluxed at 80° C. for 10 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.84 g of Compound 43 (Yield: 68%). The produced compound was identified using LC-MS and NMR.

$C_{38}H_{23}N_3$: M+521.19

$^1$H NMR (CDCl$_3$, 400 MHz) δ (ppm) 9.07 (d, 1H) 8.90 (m, 1H) 8.42 (d, 1H) 8.29 (s, 1H) 8.26-8.22 (m, 1H) 8.20-8.18 (m, 2H) 8.11 (d, 1H) 8.03 (m, 2H) 7.89 (d, 1H) 7.81-7.78 (m, 3H) 7.66-7.64 (m, 1H) 7.58-7.56 (m, 2H) 7.45-7.20 (m, 6H).

Example 1

A Corning 15 Ω/cm$^2$ (1200 Å) ITO glass substrate was cut to a size of 50 mm×50 mm×0.7 mm, sonicated using isopropyl alcohol and pure water for five minutes each, and then cleaned by irradiation of UV rays for 30 minutes and exposure to ozone. Then, resulting glass substrate was disposed in a vacuum deposition apparatus.

2-TNATA was deposited on the ITO electrode (anode) of the glass substrate to form a HIL having a thickness of 600 Å, and then 4,4'-bis[N-(1-naphthyl)-N-phenylamino]biphenyl (NPB) was deposited on the HIL to form a HTL having a thickness of 300 Å.

Then, Compound 14 and 1,4-bis-(2,2-diphenylvinyl)biphenyl (DPVBi) were co-deposited on the HTL in a weight ratio of 98:2 to form an EML having a thickness of 300 Å.

Then, Alq3 was deposited on the EML to form an ETL having a thickness of 300 Å, and LiF was deposited on the ETL to form an EIL having a thickness of 10 Å. Then, Al was deposited on the EIL to a thickness of 3000 Å, thereby forming a second electrode (cathode). As a result an organic light-emitting diode was prepared.

Example 2

An organic light-emitting diode was manufactured in the same manner as in Example 1, except that Compound 30 was used instead of Compound 14 when the EML is formed.

Example 3

An organic light-emitting diode was manufactured in the same manner as in Example 1, except that ADN was used instead of Compound 14 and Compound 20 was used instead of DPVBi when the EML is formed.

Example 4

An organic light-emitting diode was manufactured in the same manner as in Example 3, except that Compound 22 was used instead of Compound 20 when the EML is formed.

Example 5

An organic light-emitting diode was manufactured in the same manner as in Example 1, except that ADN was used instead of Compound 14 when the EML is formed and Compound 31 was used instead of Alq3 when the ETL is formed.

Example 6

An organic light-emitting diode was manufactured in the same manner as in Example 5, except that Compound 43 was used instead of Compound 31 when the ETL is formed.

Example 7

An organic light-emitting diode was manufactured in the same manner as in Example 1, except that Compound 20 was used instead of DPVBi when the EML is formed.

Example 8

An organic light-emitting diode was manufactured in the same manner as in Example 1, except that Compound 30 was used instead of Compound 14 and Compound 33 was used instead of DPVBi when the EML is formed, and Compound 31 was used instead of Alq3 when the ETL was formed.

Comparative Example 1

An organic light-emitting diode was manufactured in the same manner as in Example 1, except that a known blue fluorescent host ADN was used instead of Compound 14 when the EML is formed.

Evaluations

Driving voltage, current density, brightness, efficiency, and color of emitted light, half lifespan (at 100 mA/cm$^2$) of the organic light emitting diodes manufactured according to Examples 1 to 8 and Comparative Example 1 were evaluated using PR650 Spectroscan Source Measurement Unit. (PhotoReaserch). The results are shown in Table 1 below.

TABLE 1

| | EML | | | Driving voltage (V) | Current density (mA/cm$^2$) | Brightness (cd/m$^2$) | Efficiency (cd/A) | Color | Half-life span (hr) |
|---|---|---|---|---|---|---|---|---|---|
| | Host | Dopant | ETL | | | | | | |
| Example 1 | Compound 14 | DPVBi | Alq3 | 6.27 | 50 | 2,155 | 4.31 | blue | 181 |
| Example 2 | Compound 30 | DPVBi | Alq3 | 6.34 | 50 | 2,059 | 4.12 | blue | 201 |
| Example 3 | ADN | Compound 20 | Alq3 | 6.07 | 50 | 2,225 | 4.45 | blue | 193 |
| Example 4 | ADN | Compound 22 | Alq3 | 6.11 | 50 | 2,311 | 4.62 | blue | 176 |
| Example 5 | ADN | DPVBi | Compound 31 | 5.83 | 50 | 2,250 | 4.50 | blue | 172 |
| Example 6 | ADN | DPVBi | Compound 43 | 6.18 | 50 | 2,380 | 4.76 | blue | 198 |
| Example 7 | Compound 14 | Compound 20 | Alq3 | 5.65 | 50 | 2,145 | 4.29 | blue | 243 |
| Example 8 | Compound 30 | Compound 22 | Compound 31 | 5.48 | 50 | 2,405 | 4.81 | blue | 227 |
| Comparative Example 1 | ADN | DPVBi | Alq3 | 7.35 | 50 | 1,490 | 2.98 | blue | 120 |

Referring to Table 1, it was identified that the organic light-emitting diodes manufactured according to Examples 1 to 8 had lower driving voltage, higher brightness, higher efficiency, and longer lifespan than the organic light-emitting diode manufactured according to Comparative Example 1.

Synthesis Example 11

Synthesis of Compound 101

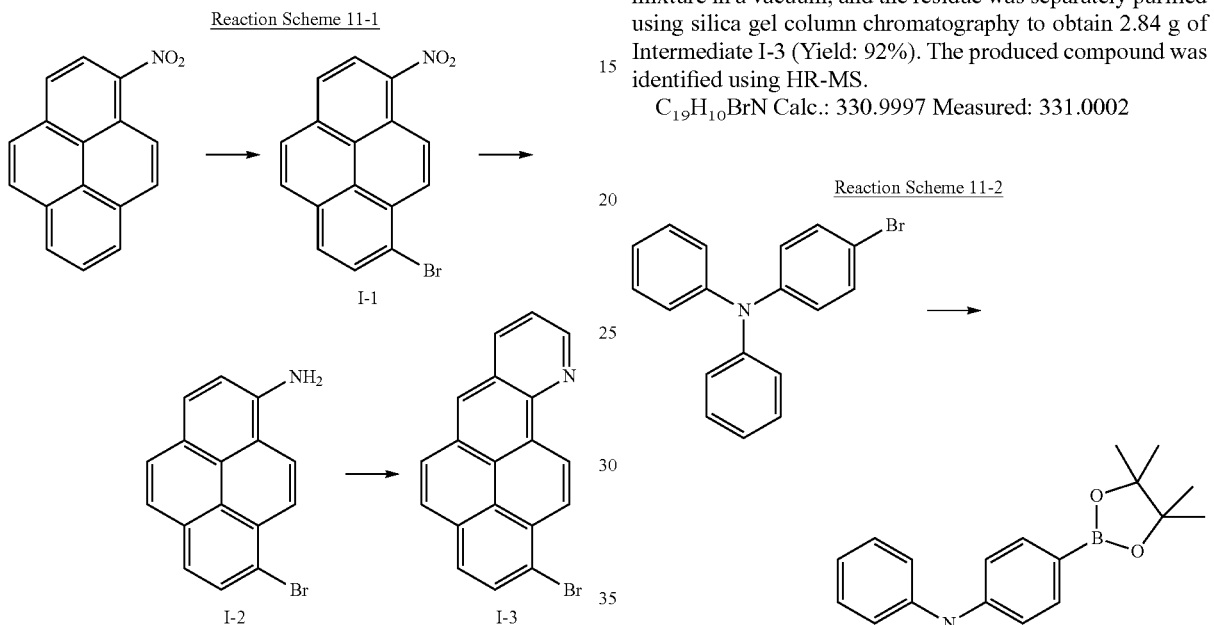

Synthesis of Intermediate I-1

4.94 g (20.0 mmol) of 1-nitropyrene was dissolved in 100 mL of dichloromethane, and 2.50 ml (20.0 mmol) of bromine ($Br_2$) were gradually added thereto at 0° C. The mixture was stirred at room temperature for 12 hours. 60 mL of water and 30 mL of a 20% sodium thiosulfate solution were added thereto. Then, the mixture was subjected to extraction three times with 80 mL of dichloromethane. An organic layer was collected and dried using magnesium sulfate to evaporate the solvent. The residue was separately purified using silica gel column chromatography and recrystallized using a dichloromethane/hexane solution to obtain 4.04 g of Intermediate I-1 (Yield: 62%) The produced compound was identified using HR-MS.

$C_{16}H_8BrNO_2$ Calc.: 324.9738 Measured: 324.9740

Synthesis of Intermediate I-2

4.04 g (12.4 mmol) of Intermediate I-1 was dissolved in 50 mL of ethanol, and 2.80 g (50 mmol) of Fe and 10 mL of a 0.1 M HCl were added thereto. The mixture was stirred at 95° C. for 3 hours. The mixture was cooled to room temperature and subjected to extraction three times with 100 mL of water and 100 mL of diethyl ether. An organic layer was collected and dried using magnesium sulfate to evaporate the solvent. The residue was separately purified using silica gel column chromatography to obtain 2.75 g of Intermediate I-2 (Yield: 75%) The produced compound was identified using HR-MS.

$C_{16}H_{10}BrN$ Calc.: 294.9997; Measured: 295.0012

Synthesis of Intermediate I-3

2.75 g (9.30 mmol) of Intermediate I-2 and 353 mg (4.65 mmol) of 1,3-propane diol were dissolved in 10 mL of mesitylene. 70 mg (0.19 mmol) of $IrCl_3H_2O$, 186 mg (0.28 mmol) of 2,2'-bis(diphenylphosphino)-1,1'-binaphthyl (BINAP), and 34 mg (0.30 mmol) of $Na_2CO_3$ were added thereto in the air. The mixture was stirred at 169° C. for 15 hours and cooled to room temperature. Then, the solvent was removed from the mixture in a vacuum, and the residue was separately purified using silica gel column chromatography to obtain 2.84 g of Intermediate I-3 (Yield: 92%). The produced compound was identified using HR-MS.

$C_{19}H_{10}BrN$ Calc.: 330.9997 Measured: 331.0002

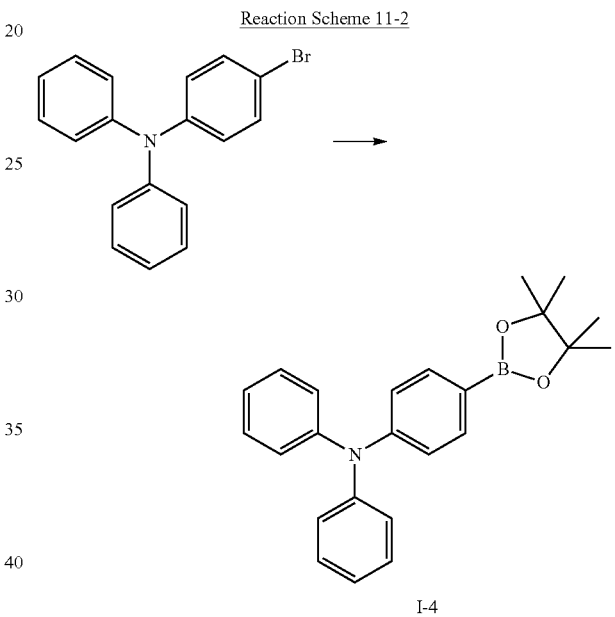

Synthesis of Intermediate I-4

3.24 g (10.0 mmol) of 4-bromotriphenylamine, 2.54 g (10.0 mmol) of bis(pinacolato)diborone, 0.36 g (0.5 mmol) of 1,1'-bis(diphenylphosphino)ferrocene]dichloro palladium (II) ($PdCl_2(dppf)_2$), and 2.94 g (30.0 mmol) of KOAc were dissolved in 40 mL of dimethyl sulfoxide (DMSO), and the mixture stirred at 80° C. for 6 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 2.57 g of Intermediate I-4 (Yield: 89%) The produced compound was identified using HR-MS.

$C_{24}H_{26}BNO_2$ Calc.: 371.2057; Measured: 371.2051

Synthesis of Compound 101

1.66 g (5.0 mmol) of Intermediate I-3, 1.86 g (5.0 mmol) of Intermediate I-4, 0.29 g (0.25 mmol) of $Pd(PPh_3)_4$, and 2.07 g (15.0 mmol) of $K_2CO_3$ were dissolved in 30 mL of a THF/$H_2O$ (2/1) solution, and the mixture was stirred at 70° C. for 5 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.86 g of Compound 101 (Yield: 75%). The produced compound was identified using HR-MS and NMR.

$C_{37}H_{24}N_2$ Calc.: 496.1939; Measured [M+1] 497.1922

$^1$H NMR (CDCl$_3$, 400 MHz) δ (ppm) 8.92-8.90 (m, 1H), 8.70-8.67 (m, 1H), 8.29-8.22 (m, 3H), 8.17-8.14 (m, 2H), 8.03 (d, 1H), 7.68 (d, 1H), 7.53-7.48 (m, 2H), 7.45-7.42 (m, 1H), 7.08-7.04 (m, 4H), 6.98-6.93 (m, 2H), 6.67-6.63 (m, 2H), 6.17-6.13 (m, 4H).

Synthesis Example 12

Synthesis of Compound 104

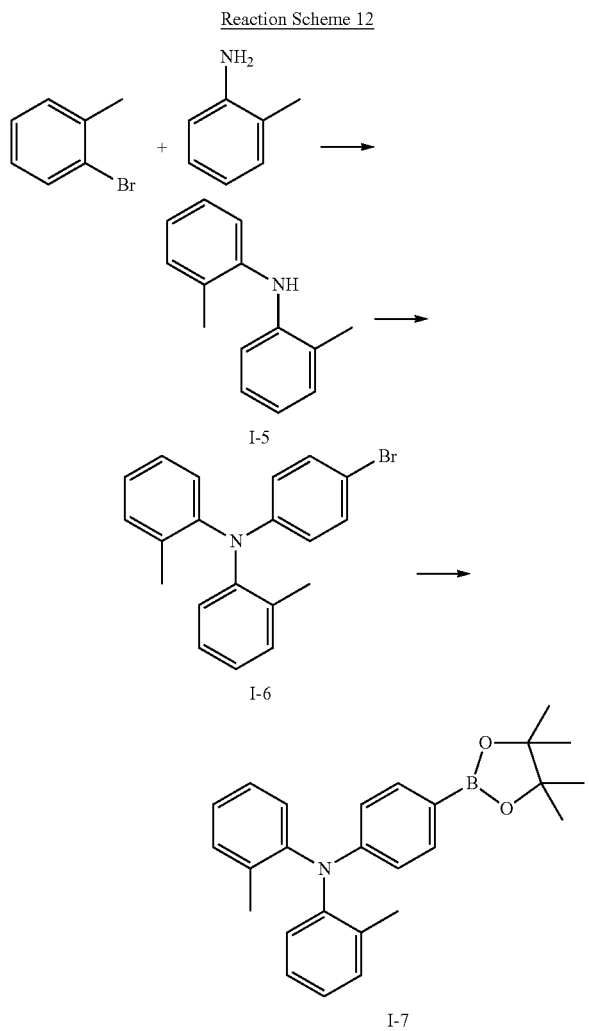

Synthesis of Intermediate I-5

3.42 g (20.0 mmol) of 1-bromo-2-methylbenzene, 2.79 g (30.0 mmol) of o-toluidine, 0.37 g (0.4 mmol) of Pd$_2$(dba)$_3$, 0.08 g (0.4 mmol) of tri-tert-burylphosphine (P(t-Bu)$_3$), and 2.88 g (30.0 mmol) of KOtBu were dissolved in 60 mL of toluene, and the mixture was stirred at 85° C. for 4 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.47 g of Intermediate I-5 (Yield: 88%) The produced compound was identified using HR-MS.

$C_{14}H_{15}N$ Calc.: 197.2204; Measured: 197.2253

Synthesis of Intermediate I-6

1.97 g (10.0 mmol) of Intermediate I-5, 2.83 g (10.0 mmol) of 4-bromoiodobenzene, 0.18 g (0.2 mmol) of Pd$_2$(dba)$_3$, 0.04 g (0.4 mmol) of P(t-Bu)$_3$, and 1.44 g (15.0 mmol) of KOtBu were dissolved in 40 mL of toluene, and the mixture was stirred at 85° C. for 4 hours. The mixture was cooled to room temperature and subjected to extraction three times with 30 mL of water and 30 mL of diethyl ether. An organic layer was collected and dried using magnesium sulfate to evaporate the solvent. The residue was separately purified using silica gel column chromatography to obtain 3.14 g of Intermediate I-6 (Yield: 89%) The produced compound was identified using HR-MS.

$C_{20}H_{18}BrN$ Calc.: 351.0623; Measured: 351.0653

Synthesis of Intermediate I-7

Intermediate I-7 was synthesized in the same manner as in the synthesis of Intermediate I-4, except that N-(4-bromophenyl)-2-methyl-N-o-tolylbenzeneamine was used instead of 4-bromotriphenylamine. The produced compound was identified using HR-MS.

$C_{26}H_{30}BNO_2$ Calc.: 399.2370; Measured: 399.2381

Synthesis of Compound 104

2.15 g of Compound 104 was synthesized with a yield of 75% in the same manner as in the synthesis of Compound 101, except that Intermediate I-7 was used instead of Intermediate I-4. The produced compound was identified using HR-MS and NMR.

$C_{39}H_{28}N_2$ Calc.: 524.2252; Measured [M+1] 525.2056

$^1$H NMR (CDCl$_3$, 400 MHz) δ (ppm) 8.92-8.90 (dd, 1H), 8.69-8.67 (d, 1H), 8.29 (s, 1H), 8.27-8.23 (m, 2H), 8.17-8.14 (m, 2H), 8.04-8.02 (d, 1H), 7.69-7.67 (d, 1H), 7.49-7.41 (m, 3H), 7.06-7.03 (m, 2H), 6.98-6.89 (m, 4H), 6.83-6.78 (m, 2H), 6.63-6.60 (m, 2H), 1.82 (s, 6H).

Synthesis Example 13

Synthesis of Compound 110

Reaction Scheme 13

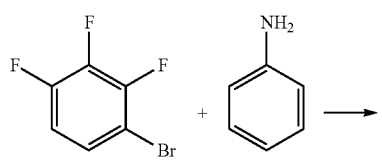

-continued

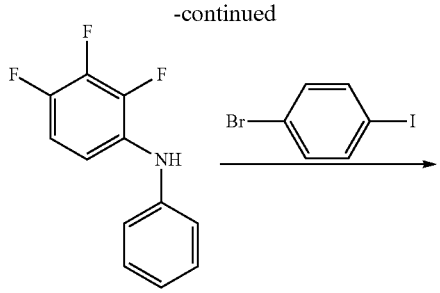

I-8

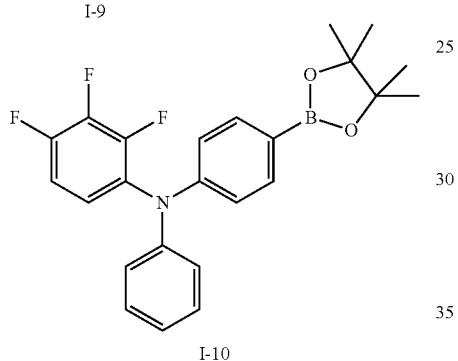

I-9

I-10

Synthesis of Intermediate I-8

5.2 g of Intermediate I-8 was synthesized with a yield of 65% in the same manner as in the synthesis of Intermediate I-5, except that 1-bromo-2,3,4-trifluorobenzene was used instead of 1-bromo-2-methylbenzene and aniline was used instead of o-toluidine. The produced compound was identified using HR-MS.

$C_{12}H_8F_3N$ Calc.: 223.0609; Measured 223.0901

Synthesis of Intermediate I-9

7.1 g of Intermediate I-9 was synthesized with a yield of 81% in the same manner as in the synthesis of Intermediate I-6, except that Intermediate I-8 was used instead of Intermediate I-5. The produced compound was identified using HR-MS.

$C_{18}H_{11}BrF_3N$ Calc.: 377.0027; Measured: 377.0023

Synthesis of Intermediate I-10

6.00 g of Intermediate I-10 was synthesized with a yield of 75% in the same manner as in the synthesis of Intermediate I-4, except that Intermediate I-9 was used instead of 4-bromotriphenylamine. The produced compound was identified using HR-MS.

$C_{24}H_{23}BF_3NO_2$ Calc.: 425.1774; Measured 425.1769

Synthesis of Compound 110

1.23 g of Compound 110 was synthesized with a yield of 63% in the same manner as in the synthesis of Compound 101, except that Intermediate I-10 was used instead of Intermediate I-4. The produced compound was identified using HR-MS and NMR. $C_{37}H_{21}F_3N_2$ Calc.: 550.1657; Measured [M+1] 551.5897

$^1$H NMR (CDCl$_3$, 400 MHz) δ (ppm) 8.92-8.90 (m, 1H), 8.69-8.67 (d, 1H), 8.29 (s, 1H), 8.26-8.22 (m, 2H), 8.17-8.14 (m, 2H), 8.04-8.02 (d, 1H), 7.69-7.67 (d, 1H), 7.54-7.50 (m, 2H), 7.45-7.41 (m, 1H), 7.10-7.05 (m, 2H), 6.81-6.70 (m, 2H), 6.66-6.56 (m, 3H), 6.37-6.34 (m, 2H).

Synthesis Example 14

Synthesis of Compound 120

Reaction Scheme 14

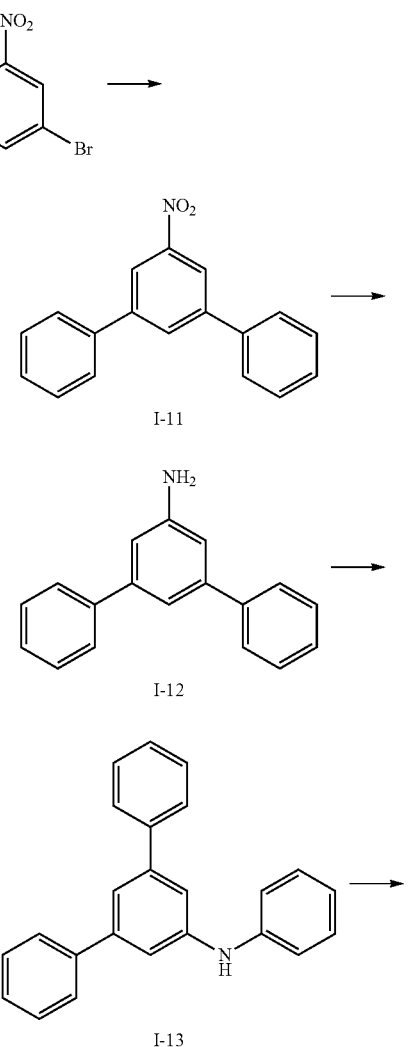

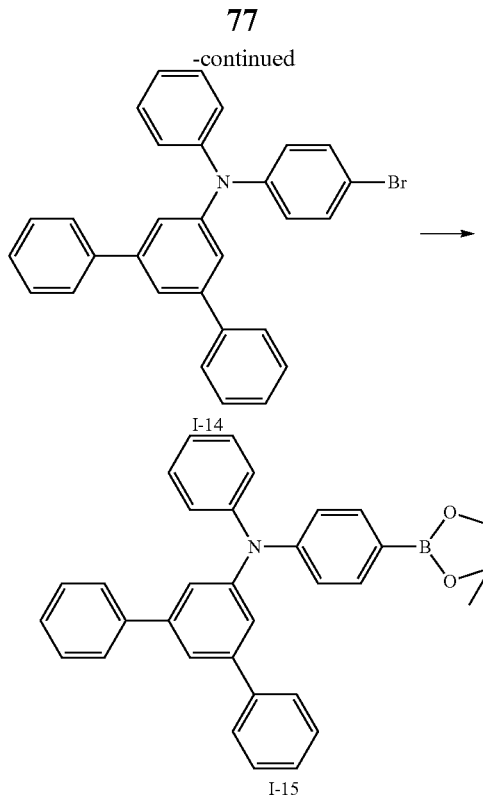

Synthesis of Intermediate I-11

5.62 g (20.0 mmol) of 1,3-dibromo-5-nitrobenzene, 1.22 g (10.0 mmol) of phenylboronic acid, 0.58 g (0.5 mmol) of PdPPh$_3$, and 4.14 g (30.0 mmol) of K$_2$CO$_3$ were dissolved in 40 mL of a THF/H$_2$O (2/1) solution, and the mixture was stirred at 80° C. for 5 hours. Then, the mixture was subjected to extraction three times with 50 mL of water and 50 mL of diethyl ether. An organic layer was collected and dried using magnesium sulfate to evaporate the solvent. The residue was separately purified using silica gel column chromatography to obtain 3.57 g of Intermediate I-11 (Yield: 65%) The produced compound was identified using HR-MS.

$C_{18}H_{13}NO_2$ Calc.: 275.0948; Measured 275.9732

Synthesis of Intermediate I-12

2.64 g of Intermediate I-12 was synthesized with a yield of 83% in the same manner as in the synthesis of Intermediate I-2, except that Intermediate I-11 was used instead of Intermediate I-1. The produced compound was identified using HR-MS.

$C_{18}H_{15}N$ Calc.: 245.1204; Measured: 245.5256

Synthesis of Intermediate I-13

2.38 g of Intermediate I-13 was synthesized with a yield of 69% in the same manner as in the synthesis of Intermediate I-5, except that 4-bromobenzene was used instead of 1-bromo-2-methylbenzene and Intermediate I-12 was used instead of o-toluidine. The produced compound was identified using HR-MS.

$C_{24}H_{19}N$ Calc.: 321.1517; Measured: 321.6245

Synthesis of Intermediate I-14

2.51 g of Intermediate I-14 was synthesized with a yield of 71% in the same manner as in the synthesis of Intermediate I-6, except that Intermediate I-13 was used instead of Intermediate I-5. The produced compound was identified using HR-MS.

$C_{30}H_{22}BrN$ Calc.: 476.0936; Measured: 476.4158

Synthesis of Intermediate I-15

2.29 g of Intermediate I-15 was synthesized with a yield of 83% in the same manner as in the synthesis of Intermediate I-1, except that Intermediate I-14 was used instead of 4-bromotriphenylamine. The produced compound was identified using HR-MS.

$C_{36}H_{34}BNO_2$ Calc.: 523.2683; Measured: 523.5641

Synthesis of Compound 120

1.65 g of Compound 120 was synthesized with a yield of 69% in the same manner as in the synthesis of Compound 101, except that Intermediate I-15 was used instead of Intermediate I-14. The produced compound was identified using HR-MS and NMR.

$C_{49}H_{32}N_2$ Calc.: 648.2565; Measured [M+1] 649.3520

$^1$H NMR (CDCl$_3$, 400 MHz) δ (ppm) 8.92-8.90 (m, 1H), 8.69-8.67 (d, 1H), 8.39 (s, 1H), 8.27-8.22 (d, 2H), 8.17-8.14 (m, 2H), 8.04-8.02 (d, 1H), 7.69-7.64 (m, 5H), 7.54-7.50 (m, 3H), 7.46-7.40 (m, 7H), 7.10-7.05 (m, 2H), 6.93-6.89 (m, 2H), 6.87-6.86 (d, 2H), 6.68-6.63 (m, 1H), 6.29-6.26 (m, 2H).

Synthesis Example 15

Synthesis of Compound 123

Synthesis of Intermediate I-16

2.3 g of Intermediate I-16 was synthesized with a yield of 51% in the same manner as in the syntheses of Intermediates I-8, I-9, and I-10, except that 2-bromopyridine was used instead of 1-bromo-2,3,4-trifluorobenzene and 2-aminopyridine was used instead of aniline. The produced compound was identified using HR-MS.

$C_{22}H_{24})_3N_3O_2$ Calc.: 373.1962; Measured: 373.1956

Synthesis of Compound 123

1.34 g of Compound 123 was synthesized with a yield of 73% in the same manner as in the synthesis of Compound 101, except that Intermediate I-16 was used instead of Intermediate I-4. The produced compound was identified using HR-MS and NMR.

$C_{35}H_{22}N_4$ Calc.: 498.1844; Measured [M-F1] 499.1925

$^1$H NMR (CDCl$_3$, 400 MHz) δ (ppm) 8.92-8.90 (m, 1H), 8.69-8.67 (d, 1H), 8.29 (s, 1H), 8.27-8.21 (m, 4H), 8.17-8.13 (m, 2H), 8.04-8.02 (s, 1H), 7.73-7.67 (m, 3H), 7.55-7.51 (m, 2H), 7.45-7.42 (dd, 1H), 7.37-7.35 (m, 2H), 6.92-6.88 (m, 2H), 6.80-6.76 (m, 2H).

Synthesis Example 16

Synthesis of Compound 133

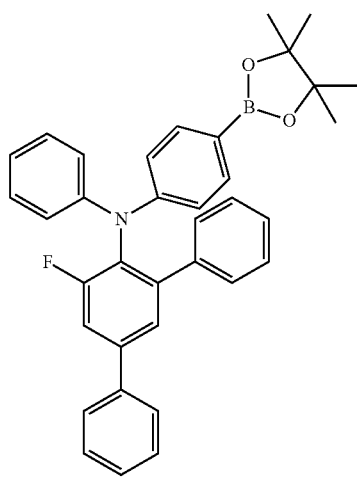

I-17

Synthesis of Intermediate I-17

2.61 g of Intermediate I-17 was synthesized with a yield of 45% in the same manner as in the syntheses of Intermediates I-11, I-12, I-13, I-14, and I-15, except that 1,3-diboromo-5-fluoro-6-nitrobenzene was used instead of 1,3-dibromo-5-nitrobenzene. The produced compound was identified using HR-MS.

$C_{38}H_{33}BFNO_2$ Calc.: 541.2588; Measured: 541.3512

Synthesis of Compound 133

1.78 g of Compound 133 was synthesized with a yield of 66% in the same manner as in the synthesis of Compound 101, except that Intermediate I-17 was used instead of Intermediate I-4. The produced compound was identified using HR-MS and NMR.

$C_{49}H_{31}FN_2$ Calc.: 666.2471; Measured: [M+1] 667.3125

$^1$H NMR (CDCl$_3$, 400 MHz) δ (ppm) 8.92-8.90 (m, 1H), 8.69-8.67 (d, 1H), 8.29 (s, 1H), 8.27-8.23 (m, 2H), 8.17-8.13 (m, 2H), 8.04-8.02 (d, 1H), 7.72-7.60 (m; 6H), 7.55-7.47 (m, 7H), 7.44-7.40 (m, 2H), 7.13-7.10 (d, 1H), 7.08-7.03 (m, 2H), 7.00-6.96 (m, 2H), 6.63-6.60 (m, 1H), 6.15-6.12 (m, 2H).

Synthesis Example 17

Synthesis of Compound 139

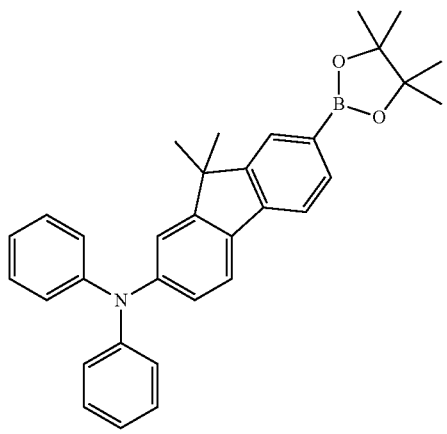

I-18

Synthesis of Intermediate I-18

Diphenylamine was synthesized in the same manner as in the synthesis of Intermediate I-5, except that bromobenzene was used instead of 1-bromo-2-methylbenzene and aniline was used instead of o-toluidine. Then, 7-bromo-9,9-dimethyl-N,N-diphenyl-9H-fluorene-2-amine was synthesized in the same manner as the synthesis of Intermediate I-6, except that diphenyl amine was used instead of Intermediate I-5 and 2-bromo-7-iodo-9,9-dimethyl-9H-fluorene was used instead of 4-bromoiodobenzene. Then, 2.59 g of Intermediate I-18 was synthesized with a yield of 46% in the same manner as in the synthesis of Intermediate I-7, except that 7-bromo-9,9-dimethyl-N,N-diphenyl-9H-fluorene-2-amine was used instead of Intermediate I-6. The produced compound was identified using HR-MS.

$C_{33}H_{34}BNO_2$ Calc.: 487.2683; Measured: 487.3541

Synthesis of Compound 139

1.99 g of Compound 139 was synthesized with a yield of 82% in the same manner as in the synthesis of Compound 101, except that Intermediate I-18 was used instead of Intermediate I-4. The produced compound was identified using HR-MS and NMR.

$C_{49}H_{32}N_2$ Calc.: 612.2565; Measured [M+1] 613.3546

$^1$H NMR (CDCl$_3$, 400 MHz) δ (ppm) 8.92-8.90 (m, 1H), 8.70-8.67 (m, 1H), 8.29 (s, 1H), 8.26-8.22 (m, 2H), 8.16-8.14 (m, 1H), 7.99-7.92 (dd, 2H), 7.80-7.76 (m, 2H), 7.68-7.66 (m, 2H), 7.54-7.52 (d, 2H), 7.50-7.48 (d, 1H), 7.45-7.41 (m, 1H), 7.08-7.04 (m, 4H), 6.67-6.63 (m, 3H), 6.40-6.38 (m, 1H), 6.16-6.13 (m, 3H), 1.82 (s, 6H).

Synthesis Example 18

Synthesis of Compound 149

1.28 g of Compound 149 was synthesized with a yield of 74% in the same manner as in the synthesis of Compound 101, except that phenyl boronic acid was used instead of Intermediate I-4. The produced compound was identified using HR-MS and NMR.

$C_{25}H_{15}N$ Calc.: 329.1204; Measured: [M+1] 330.2132

$^1$H NMR (CDCl$_3$, 400 MHz) δ (ppm) 8.92-8.90 (dd, 1H), 8.69-8.67 (d, 1H), 8.29 (s, 1H), 8.26-8.23 (m, 2H), 8.16-8.14 (d, 1H), 8.06-8.02 (m, 3H), 7.99-7.97 (d, 1H), 7.68-7.66 (d, 1H), 7.51-7.48 (m, 2H), 7.45-7.38 (m, 2H).

Synthesis Example 19

Synthesis of Compound 154

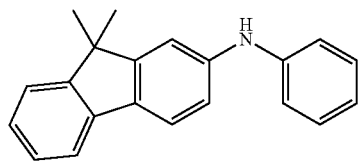

I-19

Synthesis of Intermediate I-19

4.56 g of Intermediate I-19 was synthesized with a yield of 72% in the same manner as in the synthesis of Intermediate I-5, except that 2-bromofluorene was used instead of 1-bromo-2-methylbenzene and aniline was used instead of o-toluidine. The produced compound was identified using HR-MS.

$C_{21}H_{18}N$ Calc.: 284.1439; Measured: 284.1398

Synthesis of Compound 154

1.05 g of Compound 154 was synthesized with a yield of 53% in the same manner as in the synthesis of Compound 101, except that Intermediate I-19 was used instead of Intermediate I-4. The produced compound was identified using HR-MS and NMR.

$C_{40}H_{28}N_2$ Calc.: 536.2252; Measured: [M+1] 537.2412

$^1$H NMR (CDCl$_3$, 400 MHz) δ (ppm) 8.92-8.90 (m, 1H), 8.61-8.59 (d, 1H), 8.27-8.23 (m, 2H), 8.17-8.08 (dd, 2H), 7.96-7.93 (d, 1H), 7.78-7.72 (m, 2H), 7.51-7.48 (d, 1H), 7.44-7.41 (m, 2H), 7.35-7.30 (m, 1H), 7.14-7.11 (m, 2H), 7.06-7.01 (m, 2H), 6.65-6.61 (m, 2H), 6.41-6.40 (d, 1H), 6.17-6.13 (m, 2H), 1.62 (s, 6H).

Synthesis Example 20

Synthesis of Compound 157

Reaction Scheme 20

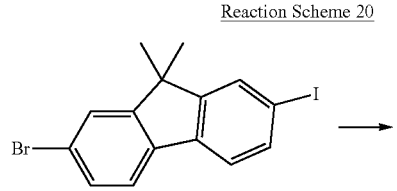

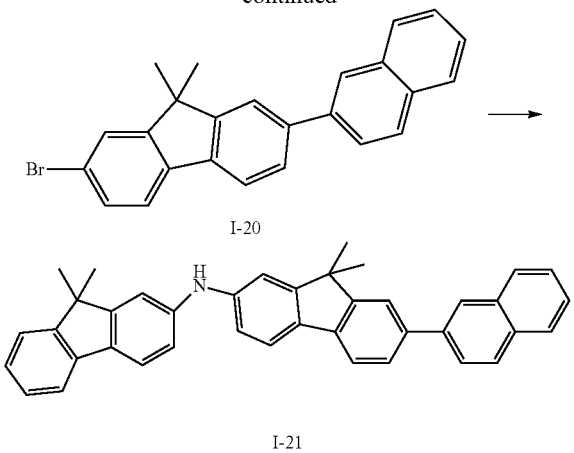

Synthesis of Intermediate I-20

3.56 g of Intermediate I-20 was synthesized with a yield of 85% in the same manner as in the synthesis of Intermediate I-11, except that 2-bromo-7-iodo-9,9-dimethyl-9H-fluorene was used instead of 1,3-diboromo-5-nitrobenzene and 2-naphthyl boronic acid was used instead of phenyl boronic acid. The produced compound was identified using HR-MS.

$C_{25}H_{19}Br$ Calc.: 398.0670; Measured: 398.0750

Synthesis of Intermediate I-21

3.81 g of Intermediate I-21 was synthesized with a yield of 81% in the same manner as in the synthesis of Intermediate I-5, except that Intermediate I-20 was used instead of 1-bromo-2-methylbenzene and 2-aminofluorene was used instead of o-toluidine. The produced compound was identified using HR-MS.

$C_{40}H_{32}N$ Calc.: 527.2613; Measured: 527.3145

Synthesis of Compound 157

1.71 g of Compound 157 was synthesized with a yield of 72% in the same manner as in the synthesis of Compound 101, except that Intermediate I-21 was used instead of Intermediate I-4. The produced compound was identified using HR-MS and NMR.

$C_{59}H_{42}N_2$ Calc.: 778.3348; Measured: [M+1] 779.4982

$^1$H NMR (CDCl$_3$, 400 MHz) δ (ppm) 8.92-8.90 (m, 1H), 8.61-8.59 (d, 1H), 8.27-8.23 (m, 2H), 8.18-8.08 (dd, 2H), 8.04 (s, 1H), 7.99-7.97 (d, 1H), 7.94-7.84 (m, 3H), 7.78-7.74 (m, 2H), 7.72-7.41 (m, 10H), 7.36-7.30 (m, 1H), 7.14-7.08 (m, 2H), 6.70-6.66 (m, 2H), 6.45-6.42 (m, 2H), 1.64-1.62 (d, 12H).

Example 11

A Corning 15 Ω/cm$^2$ (1200 Å) ITO glass substrate was cut to a size of 50 mm×50 mm×0.7 mm, sonicated using isopropyl alcohol and pure water for five minutes each, and then cleaned by irradiation of UV rays for 30 minutes and exposure to ozone. Then, resulting glass substrate was disposed in a vacuum deposition apparatus.

2-TNATA was deposited on the ITO electrode (anode) of the glass substrate to form a HIL having a thickness of 600 Å, and then 4,4'-bis[N-(1-naphthyl)-N-phenylamino]biphenyl (NPB) was deposited on the HIL to form a HTL having a thickness of 300 Å.

Then, ADN and Compound 101 were co-deposited on the HTL in a weight ratio of 98:2 to form an EML with a thickness of 300 Å.

Then, Alq3 was deposited on the EML to form an ETL having a thickness of 300 Å, and LiF was deposited on the ETL to form an EIL having a thickness of 10 Å. Then, Al was deposited on the EIL to a thickness of 3000 Å, thereby forming a second electrode (cathode). As a result, an organic light-emitting diode was prepared.

Example 12

An organic light-emitting diode was manufactured in the same manner as in Example 1, except that Compound 104 was used instead of Compound 101 when the EML is formed.

Example 13

An organic light-emitting diode was manufactured in the same manner as in Example 1, except that Compound 110 was used instead of Compound 101 when the EML is formed.

Example 14

An organic light-emitting diode was manufactured in the same manner as in Example 1, except that Compound 120 was used instead of Compound 101 when the EML is formed.

Example 15

An organic light-emitting diode was manufactured in the same manner as in Example 1, except that Compound 123 was used instead of Compound 101 when the EML is formed.

Example 16

An organic light-emitting diode was manufactured in the same manner as in Example 1, except that Compound 133 was used instead of Compound 101 when the EML is formed.

Example 17

An organic light-emitting diode was manufactured in the same manner as in Example 1, except that Compound 139 was used instead of Compound 101 when the EML is formed.

Example 18

An organic light-emitting diode was manufactured in the same manner as in Example 1, except that Compound 149 was used instead of Compound 101 when the EML is formed.

Example 19

An organic light-emitting diode was manufactured in the same manner as in Example 1, except that Compound 154 was used instead of Compound 101 when the EML is formed.

Example 20

An organic light-emitting diode was manufactured in the same manner as in Example 1, except that Compound 157 was used instead of Compound 101 when the EML is formed.

Comparative Example 2

An organic light-emitting diode was manufactured in the same manner as in Example 1, except that DPVBi was used instead of Compound 101 when the EML is formed.

Evaluations

Driving voltage, current density, brightness, color of emitted light, efficiency, and half lifespan (@100 mA/cm') of the organic light emitting diodes manufactured according to Examples 11 to 20 and Comparative Example 2 were evaluated in the same manner as in the Evaluations of Examples 1 to 8 using PR650 Spectroscan Source Measurement Unit. (PhotoReaserch). The results are shown in Table 2 below.

TABLE 2

| | Host | Dopant | Driving voltage (V) | Current density (mA/cm$^2$) | Brightness (cd/m$^2$) | Efficiency (cd/A) | Color | Half-life span. |
|---|---|---|---|---|---|---|---|---|
| Example 11 | ADN | Compound 101 | 6.25 | 50 | 2,975 | 5.95 | blue | 255 |
| Example 12 | ADN | Compound 104 | 6.49 | 50 | 2,920 | 5.84 | blue | 185 |
| Example 13 | ADN | Compound 110 | 6.51 | 50 | 2,975 | 5.95 | blue | 189 |
| Example 14 | ADN | Compound 120 | 6.53 | 50 | 2,875 | 5.75 | blue | 214 |
| Example 15 | ADN | Compound 123 | 6.38 | 50 | 2,572 | 5.14 | blue | 193 |
| Example 16 | ADN | Compound 133 | 6.31 | 50 | 2,991 | 5.98 | blue | 258 |
| Example 17 | ADN | Compound 139 | 6.49 | 50 | 2,765 | 5.53 | blue | 227 |
| Example 18 | ADN | Compound 149 | 6.47 | 50 | 2,847 | 5.69 | blue | 231 |
| Example 19 | ADN | Compound 154 | 6.51 | 50 | 2,751 | 5.50 | blue | 231 |
| Example 20 | ADN | Compound 157 | 6.58 | 50 | 2,762 | 5.52 | blue | 229 |
| Comparative Example 2 | ADN | DPVBi | 7.85 | 50 | 1,560 | 3.12 | blue | 113 |

Referring to Table 2, it was identified that the organic light-emitting diodes manufactured according to Examples 11 to 20 had lower driving voltage, higher brightness, higher efficiency, and longer lifespan than the organic light-emitting diode manufactured according to Comparative Example 2.

The organic light-emitting diode including the condensed-cyclic compound may have low driving voltage, high brightness, high efficiency, and long lifespan.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A condensed-cyclic compound represented by Formula 1 below:

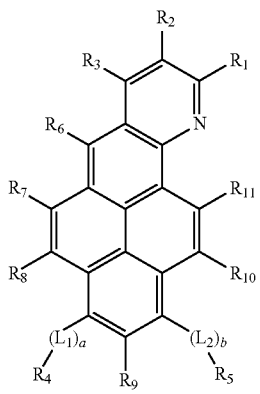

Formula 1 wherein $R_1$ to $R_{11}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($R_{21}$)($R_{22}$), or —Si($R_{23}$)($R_{24}$)($R_{25}$), and $R_4$ and $R_5$ are not a hydrogen atom at same time;

$L_1$ to $L_2$ are each independently a substituted or unsubstituted $C_6$-$C_{60}$ arylene group or a substituted or unsubstituted $C_2$-$C_{60}$ heteroarylene group;

a and b are each independently an integer from 0 to 5; and $R_{21}$ to $R_{25}$ are each independently a hydrogen atom, a heavy hydrogen atom, a halogen atom, a hydroxyl group, a cyano group, a nitro group, a carboxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

2. The condensed-cyclic compound of claim 1, wherein $R_1$ to $R_{11}$ are each independently a hydrogen atom, a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, a pentoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, or —N($R_{21}$)($R_{22}$).

3. The condensed-cyclic compound of claim 1, wherein $R_1$ to $R_{11}$ are each independently a hydrogen atom, a heavy hydrogen atom, a halogen atom, a hydroxyl group, a cyano group, a nitro group, a carboxyl group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, or a substituted or unsubstituted $C_1$-$C_{10}$ alkoxy group, or one of Formulae 2A to 2Q below:

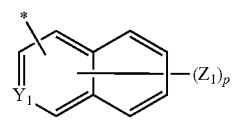

Formula 2B

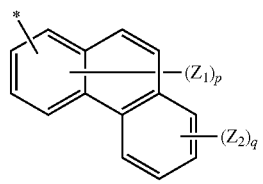

Formula 2C

-continued
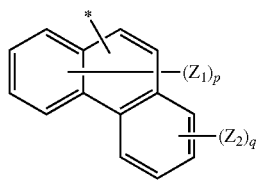
Formula 2D
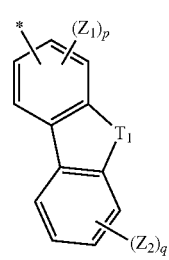
Formula 2E
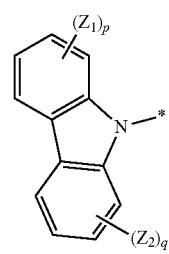
Formula 2F
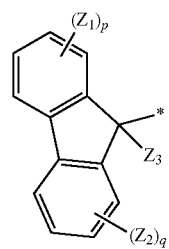
Formula 2G
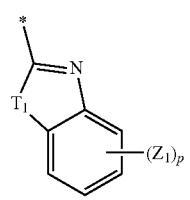
Formula 2I
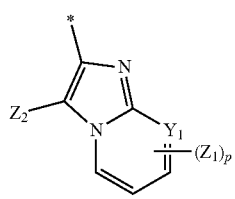
Formula 2J
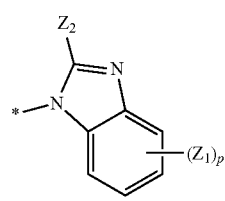
Formula 2K
-continued
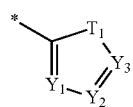
Formula 2L
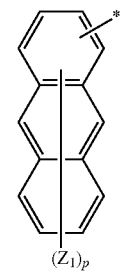
Formula 2N
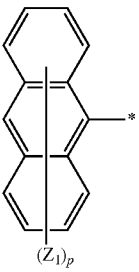
Formula 2O
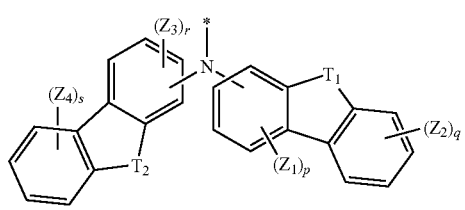
Formula 2Q
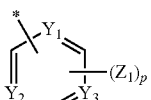
Formula 2A
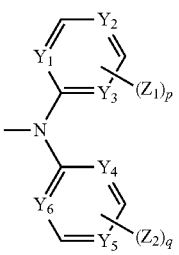
Formula 2H
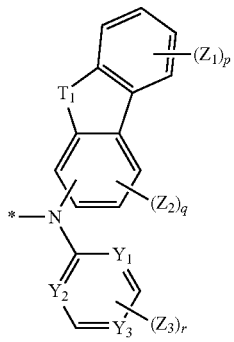
Formula 2M Formula 2P

[structure]

wherein $Y_1$ to $Y_6$ are each independently =N— or =C($Z_{11}$)—;

$T_1$ and $T_2$ are each independently —S—, —O—, —N($Z_{12}$)— or —C($Z_{13}$)($Z_{14}$)—;

$Z_1$ to $Z_4$ and $Z_{11}$ to $Z_{14}$ are each independently a hydrogen atom; a heavy hydrogen atom; a halogen atom; a hydroxyl group; a cyano group; a nitro group; a carboxyl group; a $C_1$-$C_{60}$ alkyl group; a $C_1$-$C_{60}$ alkyl group substituted with at least one of a heavy hydrogen atom, a halogen atom, a hydroxyl group, a cyano group, a nitro group, and a carboxyl group; a $C_2$-$C_{60}$ alkenyl group; a $C_2$-$C_{60}$ alkenyl group substituted with at least one of selected from the group consisting of a heavy hydrogen atom, a halogen atom, a hydroxyl group, a cyano group, a nitro group, and a carboxyl group; a $C_2$-$C_{60}$ alkynyl group; a $C_2$-$C_{60}$ alkynyl group substituted with at least one of a heavy hydrogen atom, a halogen atom, a hydroxyl group, a cyano group, a nitro group, and a carboxyl group; a $C_1$-$C_{60}$ alkoxy group; a $C_1$-$C_{60}$ alkoxy group substituted with at least one of a heavy hydrogen atom, a halogen atom, a hydroxyl group, a cyano group, a nitro group, and a carboxyl group; a $C_3$-$C_{60}$ cycloalkyl group; a $C_3$-$C_{60}$ cycloalkyl group substituted with at least one of a heavy hydrogen atom, a halogen atom, a hydroxyl group, a cyano group, a nitro group, and a carboxyl group; a $C_6$-$C_{60}$ aryl group; a $C_6$-$C_{60}$ aryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_6$-$C_{60}$ aryloxy group; a $C_6$-$C_{60}$ aryloxy group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_6$-$C_{60}$ arylthio group; a $C_6$-$C_{60}$ arylthio group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_2$-$C_{60}$ heteroaryl group; or a $C_2$-$C_{60}$ heteroaryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group;

p is an integer from 1 to 3;
q is an integer from 1 to 3;
r is an integer from 1 to 3;
s is an integer from 1 to 3; and
v, v1, and v2 are each independently an integer of 1 or 2.

4. The condensed-cyclic compound of claim 3, wherein $Z_1$ to $Z_4$ and $Z_{11}$ to $Z_{14}$ are each independently a hydrogen atom; a heavy hydrogen atom; a halogen atom; a hydroxyl group; a cyano group; a methyl group; an ethyl group; a propyl group; a butyl group; a pentyl group; an ethenyl group; a propenyl group; a butenyl group; a pentenyl group; an acetyl group; a methoxy group; an ethoxy group; a propoxy group; a butoxy group; a pentoxy group; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group or a chrysenyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; or a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group.

5. The condensed-cyclic compound of claim 1, wherein $R_1$ to $R_{11}$ are each independently a hydrogen atom, a heavy hydrogen atom, a halogen atom, a hydroxyl group, a cyano group, a nitro group, a carboxyl group, a $C_1$-$C_{10}$ alkyl group, a $C_1$-$C_{10}$ alkoxy group or one of Formulae 3A to 3T below:

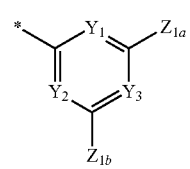

Formula 3A

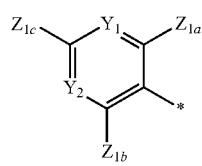

Formula 3B

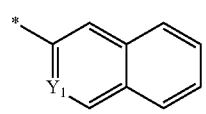

Formula 3C

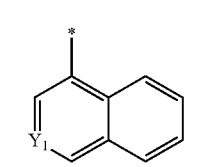

Formula 3D

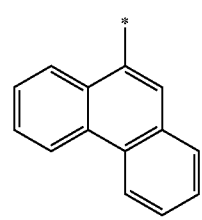

Formula 3E

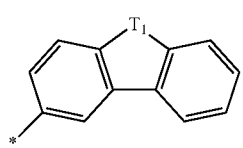
Formula 3F
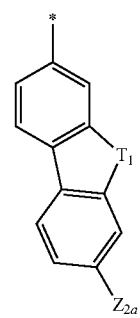
Formula 3G
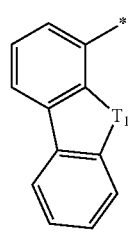
Formula 3H
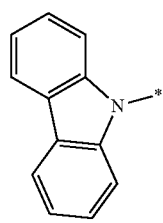
Formula 3I
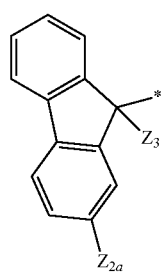
Formula 3J
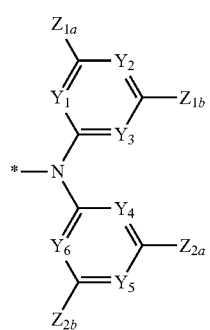
Formula 3K
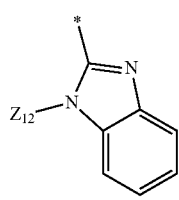
Formula 3L
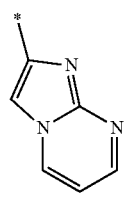
Formula 3M
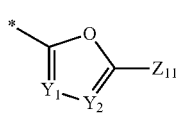
Formula 3N
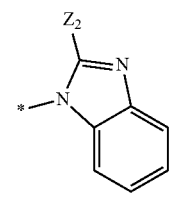
Formula 3O
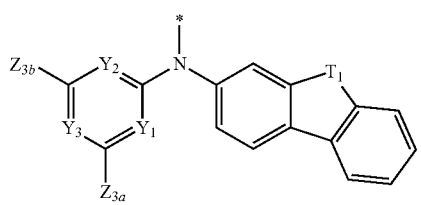
Formula 3P
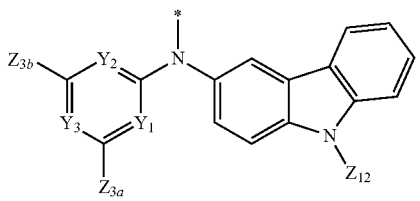
Formula 3Q
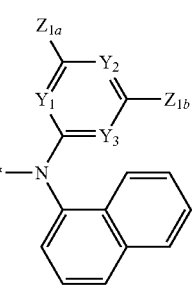
Formula 3R

93

-continued

Formula 3S

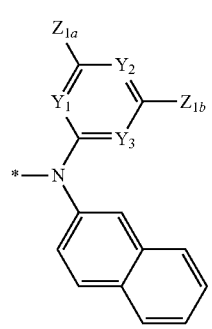

Formula 3T

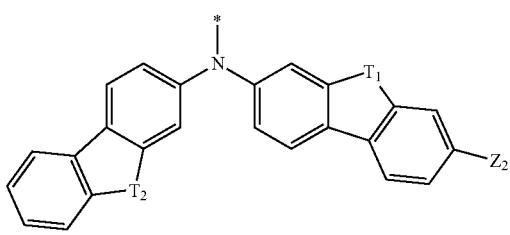

wherein $Y_1$ to $Y_6$ are each independently =N— or =C($Z_{11}$)—;

$T_1$ and $T_2$ are each independently —S—, —O—, —N($Z_{12}$)— or —C($Z_{13}$)($Z_{14}$)—; and $Z_{1a}$, $Z_{1b}$, $Z_{1c}$, $Z_2$, $Z_{2a}$, $Z_{2b}$, $Z_3$, $Z_{3a}$, $Z_{3b}$, $Z_{11}$, $Z_{12}$, $Z_{13}$, and $Z_{14}$ are each independently a hydrogen atom; a heavy hydrogen atom; a halogen atom; a hydroxyl group; a cyano group; a methyl group; an ethyl group; a propyl group; a butyl group; a pentyl group; an ethenyl group; a propenyl group; a butenyl group; a pentenyl group; an acetyl group; a methoxy group; an ethoxy group; a propoxy group; a butoxy group; a pentoxy group; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group or a chrysenyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; or a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a heavy hydrogen atom, a halogen atom, a hydroxyl group, a cyano group, a methyl group, an ethyl group, a propyl group, a butyl group, a pentyl group, an ethenyl group, a propenyl group, a butenyl group, a pentenyl group, an acetyl group, a methoxy group, an ethoxy group, a propoxy group, a butoxy group, and a pentoxy group.

6. The condensed-cyclic compound of claim 1, wherein a and b are each independently 0, 1, or 2.

7. The condensed-cyclic compound of claim 1, wherein $L_1$ and $L_2$ are each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentacenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanyl group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group.

8. The condensed-cyclic compound of claim 1, wherein $L_1$ and $L_2$ are represented by one of Formulae 4A to 4O below:

Formula 4A

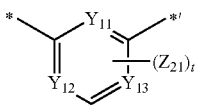

Formula 4B

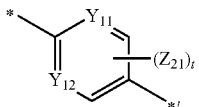

-continued

Formula 4C

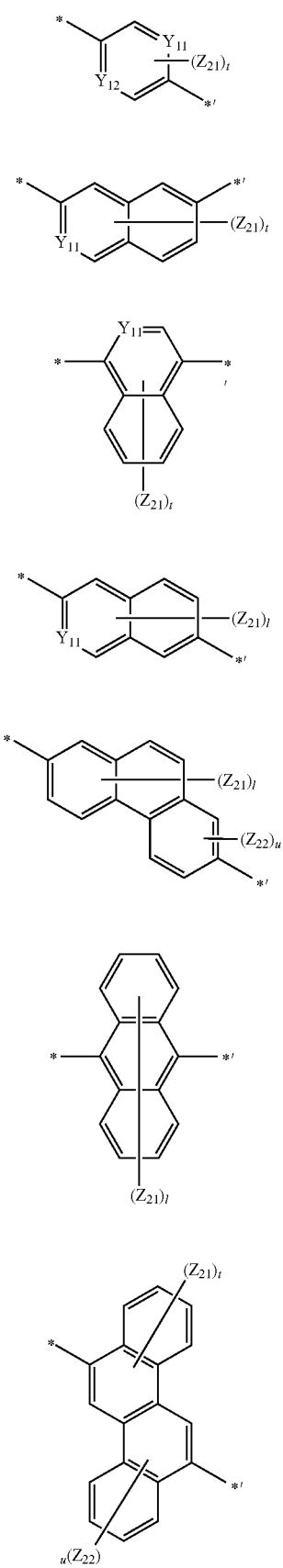

Formula 4D

Formula 4E

Formula 4F

Formula 4G

Formula 4H

Formula 4I

Formula 4J

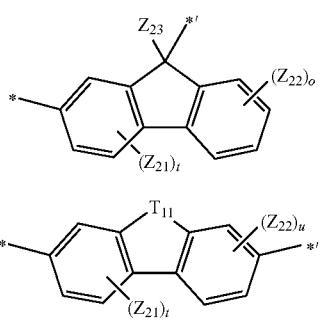

Formula 4K

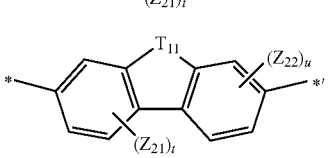

Formula 4L

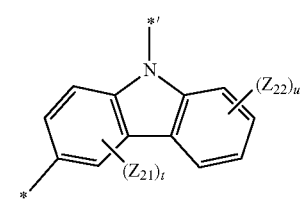

Formula 4M

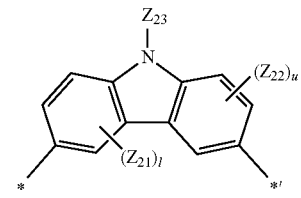

Formula 4N

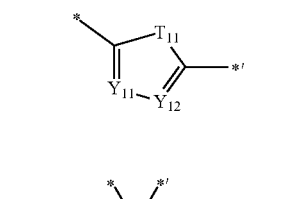

Formula 4O

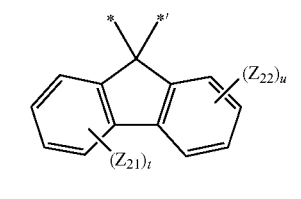

wherein $Y_{11}$ to $Y_{13}$ are each independently =N— or =C($Z_{31}$)—;

$T_{11}$ is —S—, —O—, —N($Z_{32}$)—, or —C($Z_{33}$)($Z_{34}$)—;

$Z_{21}$ to $Z_{23}$ and $Z_{31}$ to $Z_{34}$ are each independently a hydrogen atom; a heavy hydrogen atom; a halogen atom; a hydroxyl group; a cyano group; a nitro group; a carboxyl group; a $C_1$-$C_{60}$ alkyl group; a $C_1$-$C_{60}$ alkyl group substituted with at least one of a heavy hydrogen atom, a halogen atom, a hydroxyl group, a cyano group, a nitro group, and a carboxyl group; a $C_2$-$C_{60}$ alkenyl group; a $C_2$-$C_{60}$ alkenyl group substituted with at least one of a heavy hydrogen atom, a halogen atom, a hydroxyl group, a cyano group, a nitro group, and a carboxyl group; a $C_2$-$C_{60}$ alkynyl group; a $C_2$-$C_{60}$ alkynyl group substituted with at least one of a heavy hydrogen atom, a halogen atom, a hydroxyl group, a cyano group, a nitro group, and a carboxyl group; a $C_1$-$C_{60}$ alkoxy group; a $C_1$-$C_{60}$ alkoxy group substituted with at least one of a heavy hydrogen atom, a halogen atom, a hydroxyl group, a cyano group, a nitro group, and a carboxyl group; a $C_3$-$C_{60}$ cycloalkyl group; a $C_3$-$C_{60}$ cycloalkyl group substituted with at least one of a heavy hydrogen atom, a halogen atom, a hydroxyl group, a cyano group, a nitro group, and a carboxyl group; a $C_6$-$C_{60}$ aryl group; a $C_6$-$C_{60}$ aryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_6$-$C_{60}$ aryloxy group; a $C_6$-$C_{60}$ aryloxy group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_6$-$C_{60}$ arylthio group; a $C_6$-$C_{60}$ arylthio group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group; a $C_2$-$C_{60}$ heteroaryl group; or a $C_2$-$C_{60}$ heteroaryl group substituted with at least one of a heavy hydrogen atom, a halogen atom, a hydroxyl group, a cyano group, a nitro group, a carboxyl group, a $C_1$-$C_{60}$ alkyl group, and a $C_1$-$C_{60}$ alkoxy group;

t is an integer from 1 to 3;

u is an integer from 1 to 3; and w is an integer of 1 or 2.

9. The condensed-cyclic compound of claim 1, wherein the condensed-cyclic compound is represented by Formula 1A or 1B below:

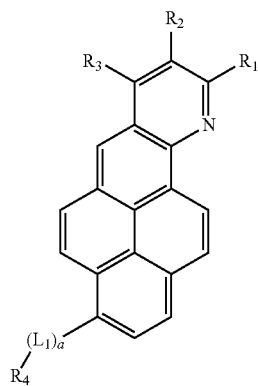

Formula 1A

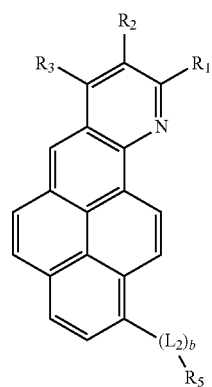

Formula 1B wherein $R_1$ to $R_5$, $L_1$, $L_2$, a, and b are defined in claim 1.

10. A condensed-cyclic compound comprises Compounds 14, 20, 22, 30, 31, 43, 101, 104, 110, 120, 123, 133, 139, 149, 154, or 157 below:

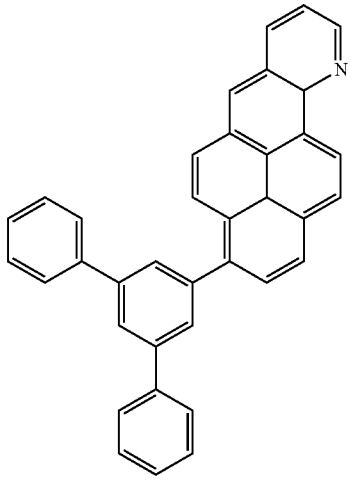

14

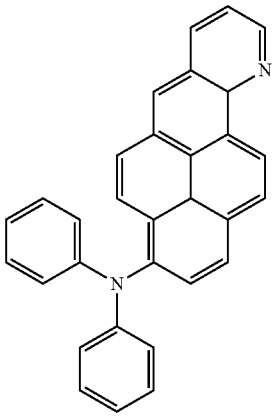

20

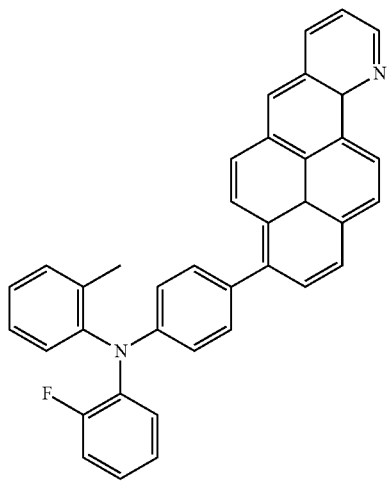

22

99
-continued
30
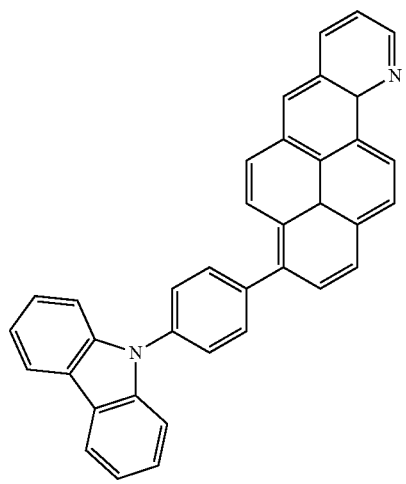
31
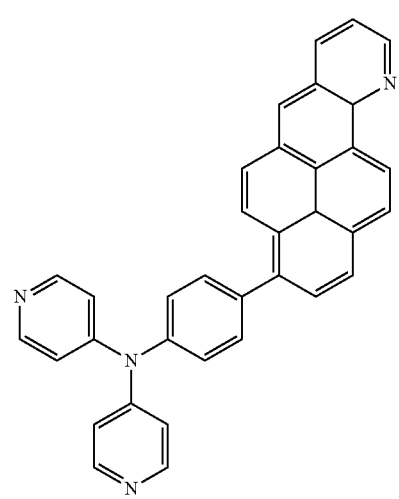
43
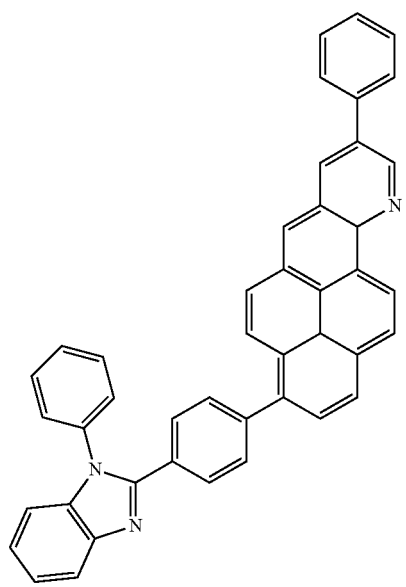
100
-continued
101
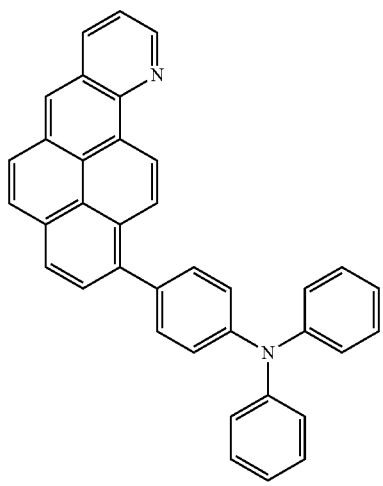
104
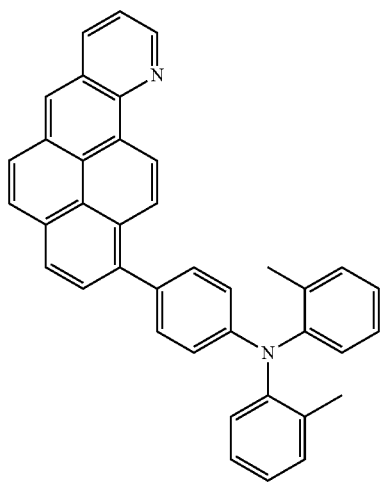
110
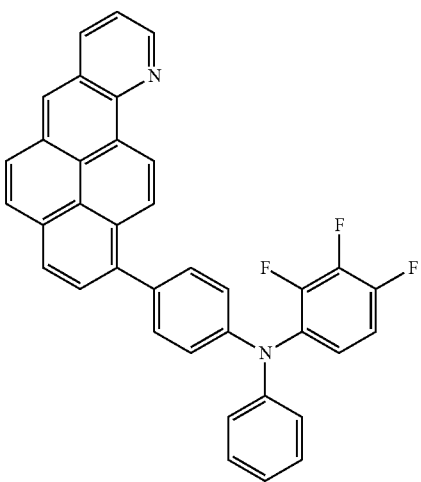

-continued
120
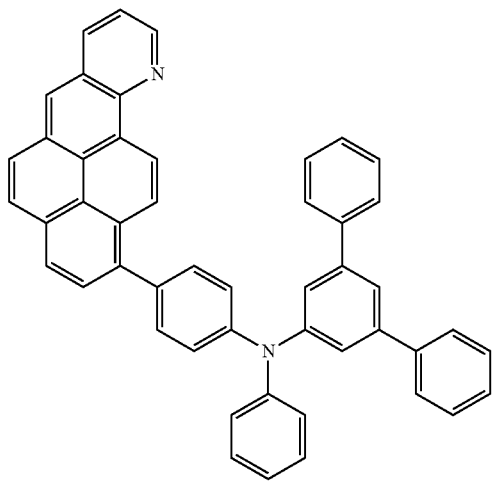
123
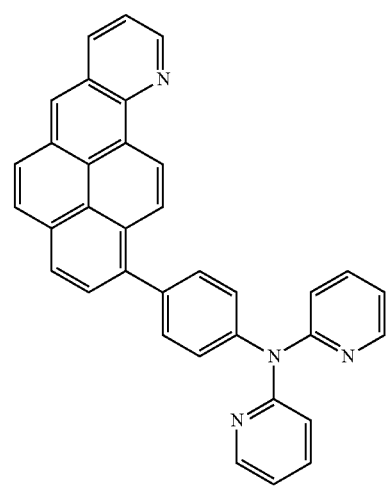
133
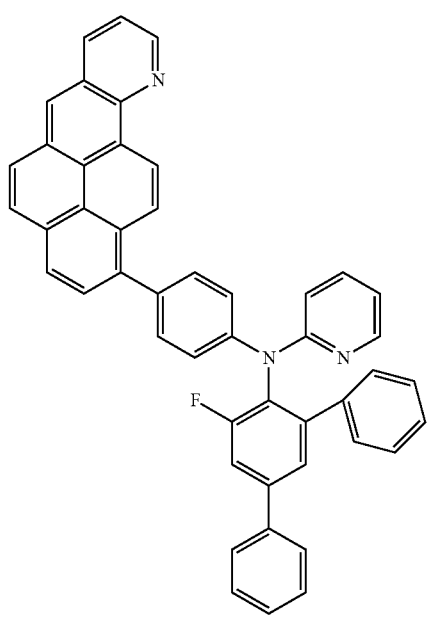
-continued
139
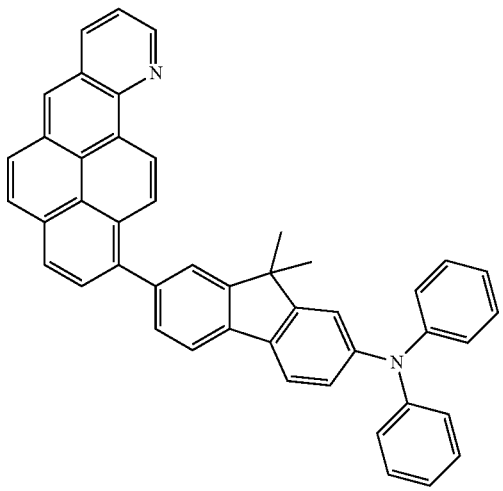
149
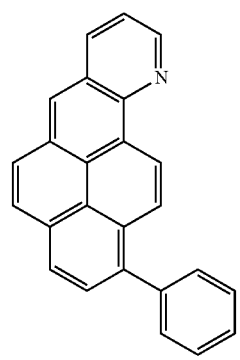
154
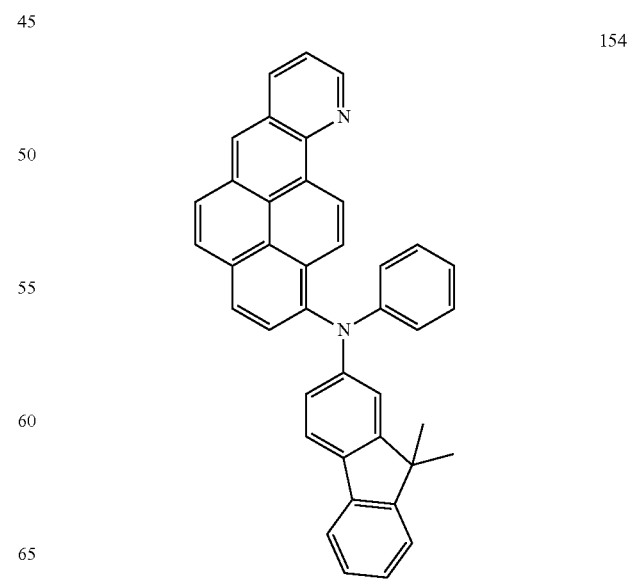

-continued

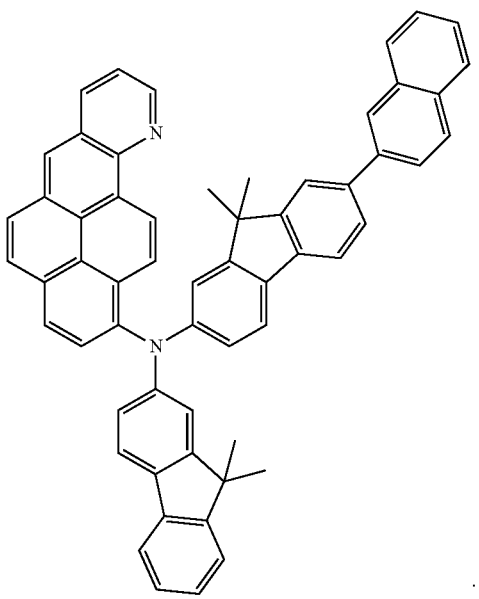

157

11. An organic light-emitting diode comprising:
a first electrode;
a second electrode disposed opposite to the first electrode; and
a first layer interposed between the first electrode and the second electrode,
wherein the first layer comprises at least one of the condensed-cyclic compounds according to claim 1.

12. The organic light-emitting diode of claim 11, wherein the first layer comprises at least one layer selected from the group consisting of a hole injection layer, a hole transport layer, a functional layer having both hole injecting and hole transporting capabilities, an electron blocking layer, an emission layer, a hole blocking layer, an electron transport layer, an electron injection layer, and a functional layer having both electron transporting and electron injecting capabilities.

13. The organic light-emitting diode of claim 12, wherein the first layer comprises an emission layer, wherein the emission layer comprises at least one of the condensed-cyclic compounds.

14. The organic light-emitting diode of claim 13, wherein the condensed-cyclic compound comprised in the emission layer functions as a host or a dopant.

15. The organic light-emitting diode of claim 13, wherein the emission layer comprises two of the condensed-cyclic compounds which are different from each other, one of the two of the condensed-cyclic compounds functions as a host and the other of the two of the condensed-cyclic compounds functions as a dopant.

16. The organic light-emitting diode of claim 13, wherein the first layer further comprises an electron transport layer, wherein the electron transport layer comprises at least one of the condensed-cyclic compounds.

17. The organic light-emitting diode of claim 16, wherein the electron transport layer further comprises a metal-containing compound.

18. The organic light-emitting diode of claim 13, wherein the first layer further comprises the electron transport layer, wherein the electron transport layer comprises at least one of the condensed-cyclic compounds which is different from the condensed-cyclic compound comprised in the emission layer.

19. The organic light-emitting diode of claim 15, wherein the first layer further comprises the electron transport layer, wherein the electron transport layer comprises at least one of the condensed-cyclic compounds which is different from the condensed-cyclic compound comprised in the emission layer.

20. The organic light-emitting diode of claim 12, wherein the first layer comprises at least one of a hole injection layer, a hole transport layer, and a functional layer having both hole injecting and hole transporting capabilities, wherein at least one selected from the group consisting of the hole injection layer, the hole transport layer, and the functional layer having both hole injecting and hole transporting capabilities comprises a charge-generating material.

21. An organic light-emitting diode comprising:
a first electrode;
a second electrode disposed opposite to the first electrode; and
a first layer interposed between the first electrode and the second electrode,
wherein the first layer comprises at least one of the condensed-cyclic compounds according to claim 10.

* * * * *